(12) United States Patent
Scott et al.

(10) Patent No.: US 11,278,526 B2
(45) Date of Patent: Mar. 22, 2022

(54) COMPOUNDS AND METHODS FOR TREATING LUPUS

(71) Applicant: RECEPTOS LLC, New York, NY (US)

(72) Inventors: Fiona Lorraine Scott, San Diego, CA (US); Kristen R. Taylor Meadows, San Diego, CA (US); Robert Peach, San Diego, CA (US)

(73) Assignee: RECEPTOS LLC, New York, NY (US)

( * ) Notice: Subject to any disclaimer, the term of this patent is extended or adjusted under 35 U.S.C. 154(b) by 0 days.

(21) Appl. No.: 16/337,292

(22) PCT Filed: Sep. 28, 2017

(86) PCT No.: PCT/US2017/054053
§ 371 (c)(1),
(2) Date: Mar. 27, 2019

(87) PCT Pub. No.: WO2018/064356
PCT Pub. Date: Apr. 5, 2018

(65) Prior Publication Data
US 2019/0224172 A1   Jul. 25, 2019

Related U.S. Application Data

(60) Provisional application No. 62/401,762, filed on Sep. 29, 2016.

(51) Int. Cl.
*A61K 31/4245*  (2006.01)
*A61P 37/02*  (2006.01)

(52) U.S. Cl.
CPC .......... *A61K 31/4245* (2013.01); *A61P 37/02* (2018.01)

(58) Field of Classification Search
CPC ............................ A61K 31/4245; A61P 37/02
See application file for complete search history.

(56) References Cited

U.S. PATENT DOCUMENTS

2013/0231326 A1 * 9/2013 Martinborough .. A61K 31/5377
514/210.18

FOREIGN PATENT DOCUMENTS

| WO | 2008/074821 | | 6/2008 |
| WO | WO2011060392 | * | 5/2011 |
| WO | 2015/066515 | | 5/2015 |
| WO | WO 2015/066515 | * | 5/2015 |

OTHER PUBLICATIONS

Gonzalez-Cabrera et al. (F1000Prime Reports, 2014, 6:109). (Year: 2014).*
Scott, (B J of Pharmacology, 2016, 173, 1778-92). (Year: 2016).*
Guerrero et al. (Expert Opinion on Therapeutic Patents, 2016, vol. 26, 4, 455-470). (Year: 2016).*
Beebe et al., Cytokine & Growth Factor Reviews, 13 2002, 403-412). (Year: 2002).*
Scott et al. (British J of Pharmacology, 2016, 173, 1778-92) (Year: 2016).*
Gonzalez-Cabrera et al. (F1000 Prime Reports, Dec. 2014, p. 1-7). (Year: 2014).*
Kegel et al. (https://lupusnewstoday.com/ 2016/01/26/s1pr1-key-to-control-autoimmune-responses-without-altering-normal-immune-reactions/) (Year: 2016).*
Armstrong (https://www.evaluate.com/vantage/articles/news/celgene-strikes-again-receptos-acquisition, 2015) (Year: 2015).*
Alkaff et al., "Transmembrane Activator and Calcium-Modulating Cyclophtilin Ligand Interactor As a Promising Novel Targeted Therapy for Systemic Lupus Erythematosus", 2017, LUPUS, vol. 4, pp. A33.
Gonzalez-Cabrera et al., "SIP signaling: new therapies and opportunities", Dec. 1, 2014, F1000Prime Reports, vol. 6, No. 109, pp. 1-7.
Scott et al., "Ozanimod (RPC1063) is apotent sphingosine-1-phosphate receptor-1 ($SIP_1$) and receptor-5($SIP_5$) agonist with autoimmune disease-modifying activity", 2016, British Journal of Pharmacology, vol. 173, pp. 1778-1792.
Tran et al., "Cardiac Safety of Ozanimod, a Novel Sphingosine-I-Phosphate Receptor Modulator: Results of a Thorough QT/QTc Study", 2017, Clinical Pharmacology in Drug Development, pp. 1-14.
Novartis Clinical Trial Results Database, "A multi-center, double-blind, placebo controlled, proof of concept study to evaluate the efficacy and tolerability of KRP203 in patients with active subacute cutaneous lupus erythematosus.", Sep. 19, 2013, pp. 1-15.

* cited by examiner

*Primary Examiner* — Umamaheswari Ramachandran
(74) *Attorney, Agent, or Firm* — Seed IP Law Group LLP

(57) ABSTRACT

Methods for treatment of systemic lupus erythematosus (SLE" or "Lupus") by administration of a modulator of sphingosine-1-phosphate receptor subtype 1 (S1P1), as well as compositions and methods related to the same, wherein such S1P1 modulators have the following general structure and wherein X and Y are as defined herein.

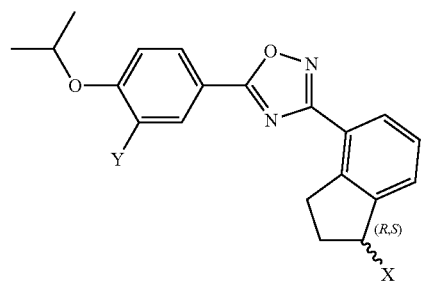

3 Claims, 47 Drawing Sheets

COMPOUNDS AND METHODS FOR TREATING LUPUS

BACKGROUND

Technical Field

Modulators of sphingosine-1-phosphate receptor subtype 1 (S1P1) are provided for treatment of systemic lupus erythematosus, as well as compositions and methods related to the same.

Description of the Related Art

Systemic Lupus Erythematosus (hereinafter "SLE" or "Lupus") is a chronic autoimmune disease in which healthy "self" tissue is mistaken as antigenic. SLE manifests most severely in periodic bouts of pronounced inflammation, known as "flares", which may manifest as joint pain, joint swelling, chest pain, fever, mouth ulcers, swollen lymph nodes, fatigue, and/or a scarlet skin rash most commonly appearing on the face. Indicators of SLE pathogenesis include the deposition of immune complexes in the kidneys, skin, brain, heart, and lungs, causing inflammation in those tissues. The kidneys are most often affected, and human SLE patients typically develop glomerulonephritis. Other indicia of SLE include the presence of anti-double-stranded DNA IgG autoantibodies (although the pathogenic role of these autoantibodies in SLE, if any, remains a subject of investigation (see Isenberg et al., *Rheumatology* 46:1052-1056, 2007)), and, in certain subpopulations of SLE patients, increases in interferon-alpha (IFNα) signature and expression of interferon response gene (see, e.g., Yung et al., *J. Am. Soc. Nehprol.* 11:1912-27, 2010; Niewold et al., *J. Biomed Biotechnol.* Epub 2010:948364).

SLE often escapes successful diagnosis because many of the related symptoms are also indicators of other diseases, such as rheumatoid arthritis. Moreover, patient subpopulations show varied expression of markers such as IFNα, and the activity and expression of such markers may further vary between quiescent and "flare" periods within a single patient. Further complicating the picture for those afflicted with SLE, although a variety of risk factors have been identified, the underlying cause of the disease remains unclear. No cure currently exists, and managing SLE is a complex, long-term endeavor that frequently requires assistance from a variety of medical and personal care specialists.

Current treatments include NSAIDs, immunosuppressants, methotrexate, azathioprine, cyclophosphamide, hydroxychloroquinine, and corticosteroids. However, current SLE therapies frequently involve prolonged use of one or more of these drugs, which may have varying degrees of efficacy and which may be accompanied by serious side effects. Thus, there is a significant need in the art for new treatment modalities for SLE.

BRIEF SUMMARY

The present disclosure is directed to methods of treating Systemic Lupus Erythematosus (also hereinafter "SLE" or "Lupus") using S1P1 modulators, as well as to methods of decreasing the expression level of a gene, the expression of which is associated with SLE, and to related kits for the diagnosis and/or treatment of SLE.

In one aspect, methods are provided from treating SLE in a subject, the methods comprising administering to the subject in need thereof an effective amount of a compound having the structure of Formula I-R or I-S or a pharmaceutically acceptable salt, homolog, hydrate or solvate thereof:

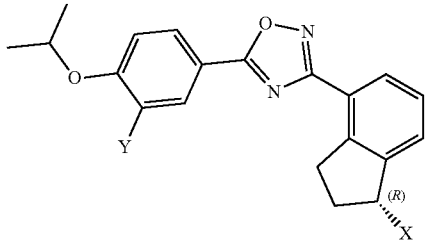

I-R

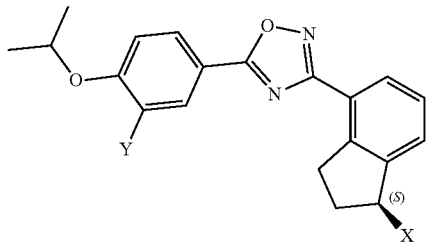

I-S wherein

X is —NR'R" or —OR'" and Y is —CN, —Cl, or —CF$_3$;

R' is H, C$_{1-4}$ alkyl, n-hydroxy C$_{1-4}$ alkyl, —SO$_2$—R$^1$, or —CO—R$^1$;

R" is H, —SO$_2$—R$^3$, C$_{1-4}$ alkyl optionally substituted with 1 or more R$^2$, or a ring moiety optionally substituted with R$^4$ wherein such ring moiety is piperidinyl, cyclohexyl, morpholinyl, pyrrolidinyl, imidazolyl, or phenyl;

R'" is H, C$_{1-4}$ alkyl, or —CO—R$^1$;

or R' and R" taken together with the nitrogen atom to which they are bound form a 4, 5, or 6 membered saturated heterocyclic ring containing 0 or 1 additional heteroatoms where such additional heteroatom is O or N wherein such heterocycle is optionally singly or multiply substituted with substituents independently selected from —OH, oxo, —NH$_2$, n-hydroxy-C$_{1-4}$ alkyl, —COOH, —(CH$_2$)m-COOH, —(CH$_2$)m-COOR$^1$, —N(R$^1$R$^1$), and —(CH$_2$)m-CO—N(R$^5$R$^5$);

R$^1$ is, at each occurrence, C$_{1-4}$ alkyl or H;

R$^2$ is, at each occurrence, H, halo, OH, oxo, =NH, NH$_2$, —COOH, F, —NHR$^1$, —N(R$^5$R$^5$), —SO$_2$—R$^1$, —SO$_2$—N(R$^5$R$^5$), —N(R$^1$)—SO$_2$—R$^1$, COOR$^1$, —OCO—R$^1$, —CO—N(R$^5$R$^5$), —N(R$^1$)—COR$^1$, C$_{1-3}$ alkyl, C$_{1-3}$ alkoxy, and a ring moiety optionally substituted with R$^4$ wherein such ring moiety is piperazinyl, piperidinyl, morpholinyl, pyrrolidinyl, pyrazolyl, imidazolyl, benzimidazolyl, azetidinyl, cyclobutinyl, or phenyl;

R$^3$ is, at each occurrence, R$^2$, C$_{1-4}$ alkyl, C$_{3-6}$ cycloalkyl, or C$_{1-4}$ alkyl optionally substituted with 1 or more R$^2$;

R$^4$ is, at each occurrence, halo, OH, —NH$_2$, —NHR$^1$, —N(R$^1$R$^1$), COOH, —COOR$^1$, —NHCO—R$^1$;

R$^5$ is, at each occurrence, C$_{1-4}$ alkyl or H, or alternatively two R$^5$ taken together with the nitrogen atom to which they are bound can form a 4, 5, or 6 membered saturated heterocyclic ring containing 0 or 1 additional heteroatoms where such additional heteroatom is O or N wherein such heterocycle is optionally substituted with —OH, NH$_2$, —N(R$^1$R$^1$), n-hydroxy C$_{1-4}$ alkyl, —(CH$_2$)m-COOH, —(CH$_2$)m-COOR$^1$; and m is, at each occurrence, 0, 1, 2, or 3.

In another aspect, methods are provided for modulating (e.g., increasing or decreasing) an expression level of a gene associated with SLE (e.g., an immune response gene, a fibrosis-related gene, or another gene associated with SLE) in a subject having or suspected of having systemic lupus erythematosus, the methods comprising administering to the subject an effective amount of a compound having Formula I-R or I-S or a pharmaceutically acceptable salt, homolog, hydrate or solvate thereof:

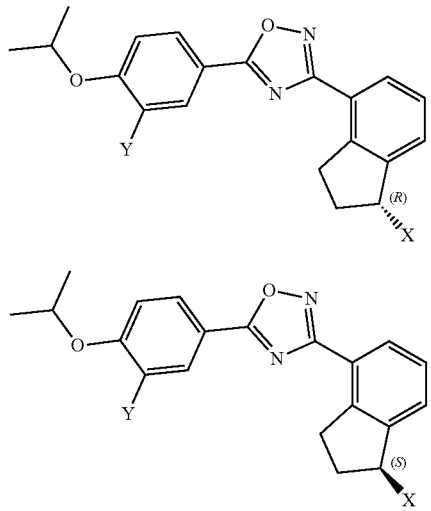

wherein
X is —NR'R" or —OR'" and Y is —CN, —Cl, or —CF$_3$;
R' is H, C$_{1-4}$ alkyl, n-hydroxy C$_{1-4}$ alkyl, —SO$_2$—R$^1$, or —CO—R$^1$;
R" is H, —SO$_2$—R$^3$, C$_{1-4}$ alkyl optionally substituted with 1 or more R$^2$, or a ring moiety optionally substituted with R$^4$ wherein such ring moiety is piperidinyl, cyclohexyl, morpholinyl, pyrrolidinyl, imidazolyl, or phenyl;
R'" is H, C$_{1-4}$ alkyl, or —CO—R$^1$;
or R' and R" taken together with the nitrogen atom to which they are bound form a 4, 5, or 6 membered saturated heterocyclic ring containing 0 or 1 additional heteroatoms where such additional heteroatom is O or N wherein such heterocycle is optionally singly or multiply substituted with substituents independently selected from —OH, oxo, —NH$_2$, n-hydroxy-C$_{1-4}$ alkyl, —COOH, —(CH$_2$)m-COOH, —(CH$_2$)m-COOR$^1$, —N(R$^1$R$^1$), and —(CH$_2$)m-CO—N(R$^5$R$^5$);
R$^1$ is, at each occurrence, C$_{1-4}$ alkyl or H;
R$^2$ is, at each occurrence, H, halo, OH, oxo, =NH, NH$_2$, —COOH, F, —NHR$^1$, —N(R$^5$R$^5$), —SO$_2$—R$^1$, —SO$_2$—N(R$^5$R$^5$), —N(R$^1$)—SO$_2$—R$^1$, COOR$^1$, —OCO—R$^1$, —CO—N(R$^5$R$^5$), —N(R$^1$)—COR$^1$, C$_{1-3}$ alkyl, C$_{1-3}$ alkoxy, and a ring moiety optionally substituted with R$^4$ wherein such ring moiety is piperazinyl, piperidinyl, morpholinyl, pyrrolidinyl, pyrazolyl, imidazolyl, benzimidazolyl, azetidinyl, cyclobutinyl, or phenyl;
R$^3$ is, at each occurrence, R$^2$, C$_{1-4}$ alkyl, C$_{3-6}$ cycloalkyl, or C$_{1-4}$ alkyl optionally substituted with 1 or more R$^2$;
R$^4$ is, at each occurrence, halo, OH, —NH$_2$, —NHR$^1$, —N(R$^1$R$^1$), COOH, —COOR$^1$, —NHCO—R$^1$;
R$^5$ is, at each occurrence, C$_{1-4}$ alkyl or H, or alternatively two R$^5$ taken together with the nitrogen atom to which they are bound can form a 4, 5, or 6 membered saturated heterocyclic ring containing 0 or 1 additional heteroatoms where such additional heteroatom is O or N wherein such heterocycle is optionally substituted with —OH, NH$_2$, —N(R$^1$R$^1$), n-hydroxy C$_{1-4}$ alkyl, —(CH$_2$)m-COOH, —(CH$_2$)m-COOR$^1$; and
m is, at each occurrence, 0, 1, 2, or 3.

In various embodiments, the gene is IL-10, IL-13, CCL5, TNFSF13b/BAFF, CXCL9, CXCL10, TGF32, LCN2/Lipocalin 2, TAGLN/Transgelin, Timp1, LOXL1, or CD88a/Girdin.

In various embodiments, the compounds used in the disclosed methods have the structure of Formula II-R or II-S, or a pharmaceutically acceptable salt, homolog, hydrate or solvate thereof:

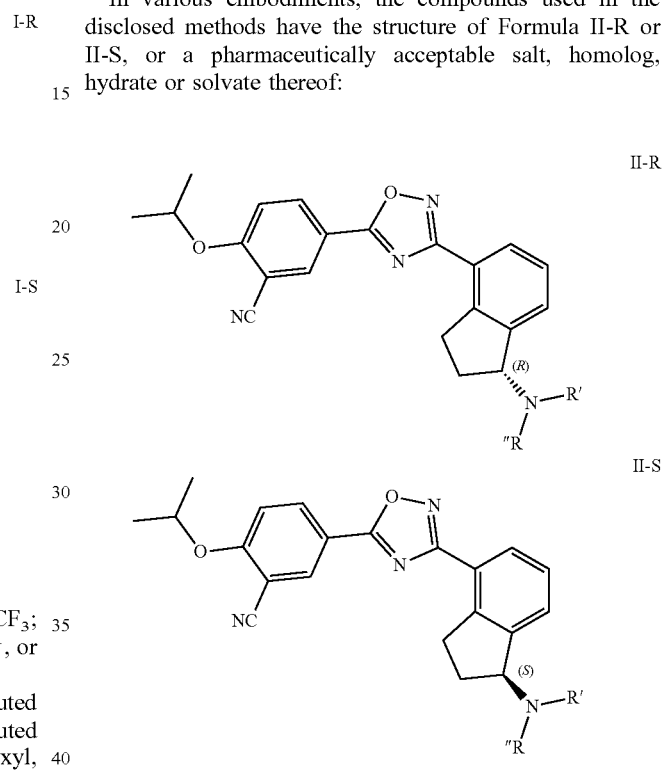

wherein
R' is H, C$_{1-4}$ alkyl, n-hydroxy C$_{1-4}$ alkyl, —SO$_2$—R$^1$, or —CO—R$^1$;
R" is H, —(CR$^a$R$^b$)n-R$^2$, or —SO$_2$—R$^3$;
or R' and R" taken together with the nitrogen atom to which they are bound form a 4, 5, or 6 membered saturated heterocyclic ring containing 0 or 1 additional heteroatom where such additional heteroatom is O or N wherein such heterocycle is optionally singly or multiply substituted with —OH, —NH$_2$, n-hydroxy-C$_{1-4}$ alkyl, —COOH, —(CH$_2$)m-COOH, —(CH$_2$)m-COOR$_1$, N(R$^1$R$^1$), —CO—N((R$^1$R$^1$);
each of R$^a$ and R$^b$ is, at each occurrence, H, hydroxyl or methyl;
or R$^a$ and R$^b$ bound to the same carbon are oxo;
R$^1$ is, at each occurrence, C1-3 alkyl or H;
R$^2$ is, at each occurrence, H, OH, oxo, NH$_2$, —COOH, F, NHR$^1$, —N(R$^1$R$^1$), —SO$_2$—R$^1$, —SO$_2$—N(R$^1$R$^1$), —COOR$^1$, —OCO—R$^1$, —CO—N(R$^1$R$^1$), C$_{1-3}$ alkyl, C$_{1-3}$ alkoxy, piperazinyl, piperidinyl, morpholinyl, pyrrolidinyl, imidazolyl, or phenyl optionally substituted with R$^4$;
R$^3$ is, at each occurrence, —(CR$^a$R$^b$)p-R$^2$ or C$_{1-4}$ alkyl;
R$^4$ is, at each occurrence, halo, OH, NH$_2$, —NHR$_1$, —N(R$^1$R$^1$), —COOH, —COOR$^1$, or —NHCO—R$^1$;
n is, at each occurrence, 1, 2, or 3;
m is, at each occurrence, 0, 1, 2, or 3; and
p is, at each occurrence, 0, 1, 2, or 3.

In more specific embodiments, the compound for use in the disclosed methods is one or more of the compounds set forth in Table 1 hereinbelow.

In various embodiments, the pharmaceutically acceptable salt is a hydrochloric salt, is a maleic acid salt, tartartic acid salt, citric acid salt, glycolic acid salt, fumaric acid salt, or methanesulfonic acid salt.

In various embodiments, the compound is in the form of a racemic mixture.

In various embodiments, the compound is in the form of an isolated optical isomer.

In various embodiments, the isolated optical isomer is at least about 90% by weight pure relative to its corresponding optical isomer.

In various embodiments, the isolated optical isomer is at least about 99% by weight pure relative to its corresponding optical isomer.

In another aspect, the present disclosure provides kits for use in treating systemic lupus erythematosus in a subject, comprising an effective amount of one or more compound as described herein for administration to the subject and, optionally, instructions for administering the compound to the subject in order to treat the systemic lupus erythematosus.

BRIEF DESCRIPTION OF THE DRAWINGS

FIG. 2A: CD4$^+$ T cells. FIG. 2B: CD8$^+$ T cells. FIG. 2C: CD19$^+$ B cells.

FIG. 41A shows mean proteinuria scores over the course of the study, while

FIG. 44A shows change in severity of glomerular lesions for the various treatment groups, while FIG. 44B shows decrease in tubular and interstitial lesions for the same.

FIG. 47A shows S1P1R expressions on activated CD4+ T cells, while FIG. 47B shows S1P1R expressions on naïve CD4+ T cells, for the various treatment groups.

DETAILED DESCRIPTION OF THE DISCLOSURE

Figure 1B:
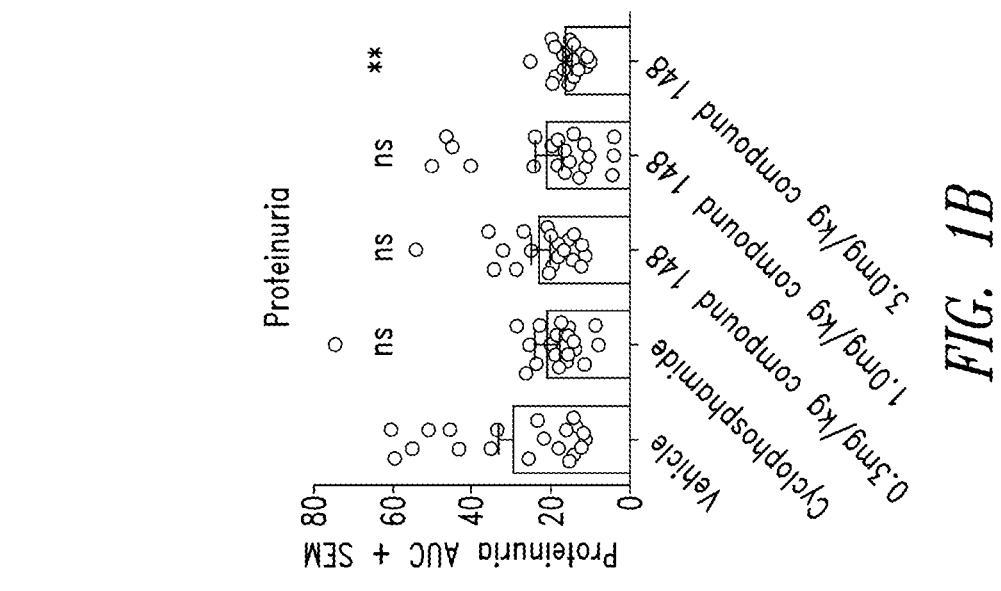
FIG. 1B shows area-under-curve (AUC) scores from the mean scores shown in FIG. 1A.

The present disclosure is prefaced upon the recognition that certain heterocyclic compounds adapted to act as modulators of sphingosine-1-phosphate (S1P) receptor subtype 1 (S1P1) are effective in treating SLE. Sphingosine-1-phosphate (S1P), the structure of which is shown below, is a phospholipid with a wide range of biological activities, including cellular signaling.

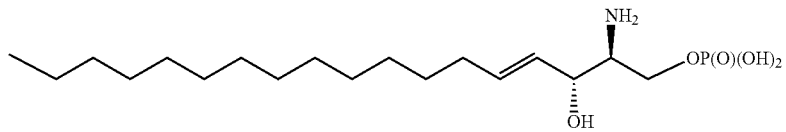

For example, S1P modulates cellular proliferation, such as of epidermal cells. The bioactivity of S1P is mediated by multiple receptor subtypes. Receptors subtypes 1 and 3, (S1P1 and S1P3 respectively) are both expressed in endothelial cells, and play a role in lung and lymphoid endothelial functions. Agonist stimulation of the S1P1 receptor is modulated by receptor degradation. Ligand stimulation induces receptor phosphorylation, internalization, polyubiquination and degradation. Oxadiazoles and oxazoles have been described for use as sphingosine-1-phosphate receptor ligands (see, e.g., WO2006/131336, WO2008/037476 and WO2008/074821). Other compounds effective for modulating S1P1 activity are disclosed in U.S. Pat. Nos. 8,481,573, 8,796,318, and 8,362,048.

As used in the specification and the appended claims, the singular forms "a," "an" and "the" include plural referents unless the context clearly dictates otherwise.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

As used herein, "subject" (as in the subject of the treatment) means both mammals and non-mammals. Mammals include, for example, humans; nonhuman primates, e.g. apes and monkeys; cattle; horses; sheep; and goats. Non mammals include, for example, fish and birds. "Subject" and "patient" are used interchangeably herein.

The term "S1P1" as used herein refers to subtype 1 of a sphingosine-1-phosphate receptor, while other sphingosine-1-phosphate receptor subtypes are referred to in a corresponding manner, for example, sphingosine-1-phosphate receptor subtype 3 is referred to as "S1P3".

A "receptor", as is well known in the art, is a biomolecular entity usually comprising a protein that specifically binds a structural class of ligands or a single native ligand in a living organism, the binding of which causes the receptor to transduce the binding signal into another kind of biological action, such as signaling a cell that a binding event has occurred, which causes the cell to alter its function in some manner. An example of transduction is receptor binding of a ligand causing alteration of the activity of a "G-protein" in the cytoplasm of a living cell. Any molecule, naturally occurring or not, that binds to a receptor and activates it for signal transduction, is referred to as an "agonist" or "activator." Any molecule, naturally occurring or not, that binds to a receptor, but does not cause signal transduction to occur, and which can block the binding of an agonist and its consequent signal transduction, is referred to as an "antagonist."

An "S1P1 compound" or "S1P1 agonist" or "S1P1 activator" or "S1P1 inhibitor" or "S1P1 antagonist" as the terms are used herein refer to compounds that interact in some way with the S1P receptor subtype 1. They can be agonist or activators, or they can be antagonists or inhibitors. An "S1P1 compound" of the disclosure can be selective for action on subtype 1 of the S1P receptor family; for example a compound of the disclosure can act at a lower concentration on subtype 1 of the S1P receptor family than on other subtypes of the S1P receptor family; more specifically, an "S1P1 compound" of the disclosure can selectively act on subtype 1 receptors compared to its action on subtype 3, or "S1P3" receptors.

As used herein, the term "about" means±20% of the indicated range, value, or structure, unless otherwise indicated.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present.

Substantially enantiomerically pure means a level of enantiomeric enrichment of one enantiomer with respect to the other enantiomer of at least 90%, 95%, 98%, 99%, 99.5% or 99.9%.

"Treating" or "treatment" within the meaning herein refers to an alleviation of symptoms associated with a disorder or disease, or inhibition of further progression or worsening of those symptoms, or prevention or prophylaxis of the disease or disorder.

The expression "effective amount", when used to describe use of a compound of the disclosure in providing therapy to a subject suffering from a disorder or malcondition mediated by a sphingosine-1-phospate receptor of subtype 1 refers to the amount of a compound of the disclosure that is effective to bind to as an agonist or as an antagonist a S1P1 receptor in the individual's tissues, wherein the S1P1 is implicated in the disorder, wherein such binding occurs to an extent sufficient to produce a beneficial therapeutic effect on the subject. Similarly, as used herein, an "effective amount" or a "therapeutically effective amount" of a compound of the disclosure refers to an amount of the compound that alleviates, in whole or in part, symptoms associated with the disorder or condition, or halts or slows further progression or worsening of those symptoms, or prevents or provides prophylaxis for the disorder or condition. In particular, a "therapeutically effective amount" refers to an amount effective, at dosages and for periods of time necessary, to achieve the desired therapeutic result by acting as an agonist of sphingosine-1-phosphate receptor subtype 1 (S1P1) activity. A therapeutically effective amount is also one in which any toxic or detrimental effects of compounds of the disclosure are outweighed by the therapeutically beneficial effects. For example, in the context of treating a malcondition mediated by activation of S1P1, a therapeutically effective amount of an S1P1 modulator of the disclosure is an amount sufficient to control the malcondition, to mitigate the progress of the malcondition, or to relieve the symptoms of the malcondition. Examples of malconditions that can be so treated include, for example, SLE.

All chiral, diastereomeric, racemic forms of a structure are intended, unless a particular stereochemistry or isomeric form is specifically indicated. Compounds used in the present disclosure can include enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the disclosure.

"Isolated optical isomer" means a compound which has been substantially purified from the corresponding optical isomer(s) of the same formula. Preferably, the isolated isomer is at least about 80%, more preferably at least 90% pure, even more preferably at least 98% pure, most preferably at least about 99% pure, by weight.

In general, "substituted" refers to an organic group as defined herein in which one or more bonds to a hydrogen atom contained therein are replaced by one or more bonds to a non-hydrogen atom such as, but not limited to, a halogen (i.e., F, Cl, Br, and I); an oxygen atom in groups such as hydroxyl groups, alkoxy groups, aryloxy groups, aralkyloxy groups, oxo(carbonyl) groups, carboxyl groups including carboxylic acids, carboxylates, and carboyxlate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R')$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)0—$_2$NHC(O)R', (CH$_2$)0-2N(R')N(R')$_2$, N(R')N(R')C(O)R', N(R')N(R')C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R')$_2$, C(O)N(OR')R', or C(=NOR')R' wherein R' can be hydrogen or a carbon-based moiety, and wherein the carbon-based moiety can itself be further substituted.

Substituted alkyl, alkenyl, alkynyl, cycloalkyl, and cycloalkenyl groups as well as other substituted groups also include groups in which one or more bonds to a hydrogen atom are replaced by one or more bonds, including double or triple bonds, to a carbon atom, or to a heteroatom such as, but not limited to, oxygen in carbonyl (oxo), carboxyl, ester, amide, imide, urethane, and urea groups; and nitrogen in imines, hydroxyimines, oximes, hydrazones, amidines, guanidines, and nitriles. The substituents of the substituted groups can further be substituted with alkyl, alkenyl, cycloalkyl, aryl, heteroaryl, and alkynyl groups as defined herein, which can themselves be further substituted. For example, an C$_{1-4}$ alkyl group can be substituted with an amide, and the amide can further be substituted with another C$_{1-4}$ alkyl, which can further be substituted.

Substituted ring groups such as substituted aryl, heterocyclyl and heteroaryl groups also include rings and fused ring systems in which a bond to a hydrogen atom is replaced with a bond to a carbon atom. Therefore, substituted aryl, heterocyclyl and heteroaryl groups can also be substituted with alkyl, alkenyl, cycloalkyl, aryl, heteroaryl, and alkynyl groups as defined herein, which can themselves be further substituted.

The term "heteroatoms" as used herein refers to non-carbon and non-hydrogen atoms, capable of forming covalent bonds with carbon, and is not otherwise limited. Typical heteroatoms are N, O, and S. When sulfur (S) is referred to, it is understood that the sulfur can be in any of the oxidation states in which it is found, thus including sulfoxides (R—S(O)—R') and sulfones (R—S(O)$_2$—R'), unless the oxidation state is specified; thus, the term "sulfone" encompasses only the sulfone form of sulfur; the term "sulfide" encompasses only the sulfide (R—S—R') form of sulfur. When the phrases such as "heteroatoms selected from the group consisting of O, NH, NR' and S," or "[variable] is O, S . . . " are used, they are understood to encompass all of the sulfide, sulfoxide and sulfone oxidation states of sulfur.

Alkyl groups include straight chain and branched alkyl groups and cycloalkyl groups having from 1 to about 20 carbon atoms (C$_{1-20}$ alkyl), and typically from 1 to 12 carbons (C$_{1-12}$ alkyl) or, in some embodiments, from 1 to 8 carbon atoms (C$_{1-8}$ alkyl) or, in some embodiments, from 1 to 4 carbon atoms (C$_{1-4}$ alkyl) or, in some embodiments, from 1 to 3 carbon atoms (C$_{1-3}$ alkyl). Examples of straight chain alkyl groups include, but are not limited to methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Representative substituted alkyl groups can be substituted one or more times with any of the groups listed above, for example, amino, hydroxy, cyano, carboxy, nitro, thio, alkoxy, and halogen groups. The group "n-hydroxy C$_{1-4}$ alkyl" represents an C$_{1-4}$ alkyl substituted with a terminal hydroxy group.

Cycloalkyl groups are alkyl groups forming a ring structure, which can be substituted or unsubstituted. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like. Cycloalkyl groups also include rings that are substituted with straight or branched chain alkyl groups as defined above. Representative substituted cycloalkyl groups can be mono-substituted or substituted more than once, such as, but not limited to, 2,2-, 2,3-, 2,4-2,5- or 2,6-disubstituted cyclohexyl groups or mono-, di- or tri-substituted norbornyl or cycloheptyl groups, which can be substituted with, for example, amino, hydroxy, cyano, carboxy, nitro, thio, alkoxy, and halogen groups.

The terms "carbocyclic" and "carbocycle" denote a ring structure wherein the atoms of the ring are carbon. In some embodiments, the carbocycle has 3 to 8 ring members, whereas in other embodiments the number of ring carbon atoms is 4, 5, 6, or 7. Unless specifically indicated to the contrary, the carbocyclic ring can be substituted with as many as N substituents wherein N is the size of the carbocyclic ring with for example, amino, hydroxy, cyano, carboxy, nitro, thio, alkoxy, and halogen groups.

(Cycloalkyl)alkyl groups, also denoted cycloalkylalkyl, are alkyl groups as defined above in which a hydrogen or carbon bond of the alkyl group is replaced with a bond to a cycloalkyl group as defined above.

Alkenyl groups include straight and branched chain and cyclic alkyl groups as defined above, except that at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to CH=CH(CH$_3$), CH=C(CH$_3$)$_2$, C(CH$_3$)=CH$_2$, C(CH$_3$)=CH(CH$_3$), C(CH$_2$CH$_3$)=CH$_2$, vinyl, cyclohexenyl, cyclopentenyl, cyclohexadienyl, butadienyl, pentadienyl, and hexadienyl among others.

The term "cycloalkenyl" alone or in combination denotes a cyclic alkenyl group wherein at least one double bond is present in the ring structure. Cycloalkenyl groups include cycloalkyl groups having at least one double bond between two adjacent carbon atoms. Thus for example, cycloalkenyl groups include but are not limited to cyclohexenyl, cyclopentenyl, and cyclohexadienyl groups.

(Cycloalkenyl)alkyl groups are alkyl groups as defined above in which a hydrogen or carbon bond of the alkyl group is replaced with a bond to a cycloalkenyl group as defined above.

Alkynyl groups include straight and branched chain alkyl groups, except that at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), CH$_2$C≡CH, CH$_2$C≡C(CH$_3$), and CH$_2$C≡C(CH$_2$CH$_3$), among others.

Aryl groups are cyclic aromatic hydrocarbons that do not contain heteroatoms. Thus aryl groups include, but are not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. The phrase "aryl groups" includes groups containing fused rings, such as fused aromatic-aliphatic ring systems (e.g., indanyl, tetrahydronaphthyl, and the like), and also includes substituted aryl groups that have other groups, including but not limited to alkyl, halo, amino, hydroxy, cyano, carboxy, nitro, thio, or alkoxy groups, bonded to one of the ring atoms. Representative substituted aryl groups can be mono-substituted or substituted more than once, such as, but not limited to, 2-, 3-, 4-, 5-, or 6-substituted phenyl or naphthyl groups, which can be substituted with groups including but not limited to those listed above.

Aralkyl groups are alkyl groups as defined above in which a hydrogen or carbon bond of an alkyl group is replaced with a bond to an aryl group as defined above. Representative aralkyl groups include benzyl and phenylethyl groups and fused (cycloalkylaryl)alkyl groups such as 4-ethyl-indanyl. The aryl moiety or the alkyl moiety or both are optionally substituted with other groups, including but not limited to alkyl, halo, amino, hydroxy, cyano, carboxy, nitro, thio, or alkoxy groups. Aralkenyl group are alkenyl groups as defined above in which a hydrogen or carbon bond of an alkyl group is replaced with a bond to an aryl group as defined above.

Heterocyclyl groups include aromatic and non-aromatic ring compounds (heterocyclic rings) containing 3 or more ring members, of which one or more is a heteroatom such as, but not limited to, N, O, S, or P. In some embodiments, heterocyclyl groups include 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a C2-heterocyclyl can be a 5-membered ring with two carbon atoms and three heteroatoms, a 6-membered ring with two carbon atoms and four heteroatoms and so forth. Likewise a C4-heterocyclyl can be a 5-membered ring with one heteroatom, a 6-membered ring with two heteroatoms, and so forth. The number of carbon atoms plus the number of heteroatoms sums up to equal the total number of ring atoms. A saturated heterocyclic ring refers to a heterocyclic ring containing no unsaturated carbon atoms.

The phrase "heterocyclyl group" includes fused ring species including those having fused aromatic and non-aromatic groups. The phrase also includes polycyclic ring systems containing a heteroatom such as, but not limited to, quinuclidyl and also includes heterocyclyl groups that have substituents, including but not limited to alkyl, halo, amino, hydroxy, cyano, carboxy, nitro, thio, or alkoxy groups, bonded to one of the ring members. A heterocyclyl group as defined herein can be a heteroaryl group or a partially or completely saturated cyclic group including at least one ring heteroatom. Heterocyclyl groups include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups. Heterocyclyl groups can be substituted. Representative substituted heterocyclyl groups can be mono-substituted or substituted more than once, including but not limited to, rings containing at least one heteroatom which are mono, di, tri, tetra, penta, hexa, or higher-substituted with substituents such as those listed above, including but not limited to alkyl, halo, amino, hydroxy, cyano, carboxy, nitro, thio, and alkoxy groups.

Heteroaryl groups are aromatic ring compounds containing 5 or more ring members, of which, one or more is a heteroatom such as, but not limited to, N, O, and S. A heteroaryl group designated as a C2-heteroaryl can be a 5-membered ring with two carbon atoms and three heteroatoms, a 6-membered ring with two carbon atoms and four heteroatoms and so forth. Likewise a C4-heteroaryl can be a 5-membered ring with one heteroatom, a 6-membered ring with two heteroatoms, and so forth. The number of carbon atoms plus the number of heteroatoms sums up to equal the total number of ring atoms. Heteroaryl groups include, but are not limited to, groups such as pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. The terms "heteroaryl" and "heteroaryl groups" include fused ring compounds such as wherein at least one ring, but not necessarily all rings, are aromatic, including tetrahydroquinolinyl, tetrahydroisoquinolinyl, indolyl and 2,3-dihydro indolyl. The term also includes heteroaryl groups that have other groups bonded to one of the ring members, including but not limited to alkyl, halo, amino, hydroxy, cyano, carboxy, nitro, thio, or alkoxy groups. Representative substituted heteroaryl groups can be substituted one or more times with groups such as those listed above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N hydroxyimidazolyl, anthracenyl (1-anthracenyl, 2-anthracenyl, 3-anthracenyl), thiophenyl (2 thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4 imidazolyl, 5-imidazolyl), triazolyl (1,2,3-triazol-1-yl, 1,2,3-triazol-2-yl 1,2,3-triazol-4-yl, 1,2,4-triazol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3 pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3 quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6 benzo[b]furanyl, 7-benzo[b]furanyl), 2,3-dihydro-benzo[b]furanyl (2-(2,3-dihydro-benzo[b]furanyl), 3-(2,3-dihydro-benzo[b]furanyl), 4-(2,3-dihydro-benzo[b]furanyl), 5 (2,3 dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4 benzo[b]thiophenyl, 5 benzo[b]thiophenyl, 6-benzo[b]thiophenyl, 7-benzo[b]thiophenyl), 2,3 dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2 indolyl, 3 indolyl, 4-indolyl, 5-indolyl, 6-indolyl, 7-indolyl), indazole (1-indazolyl, 3 indazolyl, 4 indazolyl, 5-indazolyl, 6-indazolyl, 7-indazolyl), benzimidazolyl (1 benzimidazolyl, 2 benzimidazolyl, 4-benzimidazolyl, 5-benzimidazolyl, 6-benzimidazolyl, 7 benzimidazolyl, 8 benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6 benzothiazolyl, 7 benzothiazolyl), carbazolyl (1-carbazolyl, 2-carbazolyl, 3-carbazolyl, 4 carbazolyl), 5H dibenz[b,f]azepine (5H-dibenz[b,f]azepin-1-yl, 5H-dibenz[b,f]azepine-2-yl, 5H dibenz[b,f]azepine-3-yl, 5H-dibenz[b,f]azepine-4-yl, 5H-dibenz[b,f]azepine-5-yl), 10,11 dihydro-5H-dibenz[b,f]azepine (10,11-dihydro-5H-dibenz[b,f]azepine-1-yl, 10,11 dihydro-5H-dibenz[b,f]azepine-2-yl, 10,11-dihydro-5H-dibenz[b,f]azepine-3-yl, 10,11 dihydro-5H-dibenz[b,f]azepine-4-yl, 10,11-dihydro-5H-dibenz[b,f]azepine-5-yl), and the like.

Heterocyclylalkyl groups are alkyl groups as defined above in which a hydrogen or carbon bond of an alkyl group is replaced with a bond to a heterocyclyl group as defined above. Representative heterocyclyl alkyl groups include, but are not limited to, furan-2-yl methyl, furan-3-yl methyl, pyridine-2-yl methyl (α-picolyl), pyridine-3-yl methyl (β-picolyl), pyridine-4-yl methyl (γ-picolyl), tetrahydrofuran-2-yl ethyl, and indol-2-yl propyl. Heterocyclylalkyl groups can be substituted on the heterocyclyl moiety, the alkyl moiety, or both.

Heteroarylalkyl groups are alkyl groups as defined above in which a hydrogen or carbon bond of an alkyl group is replaced with a bond to a heteroaryl group as defined above. Heteroarylalkyl groups can be substituted on the heteroaryl moiety, the alkyl moiety, or both.

By a "ring system" as the term is used herein is meant a moiety comprising one, two, three or more rings, which can be substituted with non-ring groups or with other ring systems, or both, which can be fully saturated, partially unsaturated, fully unsaturated, or aromatic, and when the ring system includes more than a single ring, the rings can be fused, bridging, or spirocyclic.

The term "amine" includes primary, secondary, and tertiary amines having, e.g., the formula N(group)3 wherein each group can independently be H or non-H, such as alkyl, aryl, and the like. Amines include but are not limited to $RNH_2$, for example, alkylamines, arylamines, alkylarylamines; $R^2NH$ wherein each R is independently selected, such as dialkylamines, diarylamines, aralkylamines, heterocyclylamines and the like; and $R^3N$ wherein each R is independently selected, such as trialkylamines, dialkylarylamines, alkyldiarylamines, triarylamines, and the like. The term "amine" also includes ammonium ions as used herein.

An "amino" group is a substituent of the form —$NH_2$, —NHR, —$NR^2$, —$NR^{3+}$, wherein each R is independently selected, and protonated forms of each. Accordingly, any compound substituted with an amino group can be viewed as an amine.

An "ammonium" ion includes the unsubstituted ammonium ion $NH_4^+$, but unless otherwise specified, it also includes any protonated or quaternarized forms of amines. Thus, trimethylammonium hydrochloride and tetramethylammonium chloride are both ammonium ions, and amines, within the meaning herein.

The term "amide" (or "amido") includes C- and N-amide groups, i.e., C(O)NR'R", and —NR'C(O)R" groups, respectively. The R' and R" of the C-amide may join together to form a heterocyclic ring with the nitrogen atom. Amide groups therefore include but are not limited to carbamoyl groups (—C(O)$NH_2$) and formamide groups (—NHC(O)H). A "carboxamido" group is a group of the formula C(O)$NR^2$, wherein R can be H, alkyl, aryl, etc.

"Halo," "halogen," and "halide" include fluorine, chlorine, bromine and iodine.

A "salt" as is well known in the art includes an organic compound such as a carboxylic acid, a sulfonic acid, or an amine, in ionic form, in combination with a counterion. For example, acids in their anionic form can form salts with cations such as metal cations, for example sodium, potassium, and the like; with ammonium salts such as $NH_4^+$ or the cations of various amines, including tetraalkyl ammonium salts such as tetramethylammonium and alkyl ammonium salts such as tromethamine salts, or other cations such as trimethylsulfonium, and the like. A "pharmaceutically acceptable" or "pharmacologically acceptable" salt is a salt formed from an ion that has been approved for human consumption and is generally non-toxic, such as a chloride salt or a sodium salt. A "zwitterion" is an internal salt such as can be formed in a molecule that has at least two ionizable groups, one forming an anion and the other a cation, which serve to balance each other. For example, amino acids such as glycine can exist in a zwitterionic form. A "zwitterion" is a salt within the meaning herein. The compounds of the present disclosure may take the form of salts. The term "salts" embraces addition salts of free acids or free bases which are compounds of the disclosure. Salts can be "pharmaceutically-acceptable salts." The term "pharmaceutically acceptable salt" refers to salts which possess toxicity profiles within a range that affords utility in pharmaceutical applications. Pharmaceutically unacceptable salts may nonetheless possess properties such as high crystallinity, which have utility in the practice of the present disclosure, such as for example utility in process of synthesis, purification or formulation of compounds of the disclosure.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4 hydroxybenzoic, phenylacetic, mandelic, embonic (pamoic), methanesulfonic, ethanesulfonic, benzenesulfonic, pantothenic, trifluoromethanesulfonic, 2 hydroxyethanesulfonic, p toluenesulfonic, sulfanilic, cyclohexylaminosulfonic, stearic, alginic, β hydroxybutyric, salicylic, galactaric and galacturonic acid. Examples of pharmaceutically unacceptable acid addition salts include, for example, perchlorates and tetrafluoroborates.

Suitable pharmaceutically acceptable base addition salts of compounds of the disclosure include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N' dibenzylethylenediamine, chloroprocaine, choline, diethanolamine, ethylenediamine, meglumine (N-methylglucamine) and procaine. Examples of pharmaceutically unacceptable base addition salts include lithium salts and cyanate salts. Although pharmaceutically unacceptable salts are not generally useful as medicaments, such salts may be useful, for example as intermediates in the synthesis of compounds, for example in their purification by recrystallization. All of these salts may be prepared by conventional means from the corresponding compound by reacting, for example, the appropriate acid or base with the compound. The term "pharmaceutically acceptable salts" refers to nontoxic inorganic or organic acid and/or base addition salts, see, for example, Gould et al., Salt Selection for Basic Drugs (1986), *Int J. Pharm.,* 33, 201-217, incorporated by reference herein.

Non-limiting examples of potential salts of this disclosure include but are not limited to hydrochloride, citrate, glycolate, fumarate, malate, tartrate, mesylate, esylate, cinnamate, isethionate, sulfate, phosphate, diphosphate, nitrate, hydrobromide, hydroiodide, succinate, formate, acetate, dichloroacetate, lactate, p-toluenesulfonate, pamitate, pidolate, pamoate, salicylate, 4-aminosalicylate, benzoate, 4-acetamido benzoate, glutamate, aspartate, glycolate, adipate, alginate, ascorbate, besylate, camphorate, camphorsulfonate, camsylate, caprate, caproate, cyclamate, laurylsulfate, edisylate, gentisate, galactarate, gluceptate, gluconate, glucuronate, oxoglutarate, hippurate, lactobionate, malonate, maleate, mandalate, napsylate, napadisylate, oxalate, oleate, sebacate, stearate, succinate, thiocyanate, undecylenate, and xinafoate.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form, i.e., a compound in water solution, while it may be hydrated, is not a hydrate as the term is used herein.

A "homolog" of a compound of the disclosure is a compound having one or more atoms of the compound replaced by an isotope of such atom. For example, homologs include compounds with deuterium in place of one or more hydrogen atoms of the compound such as compounds of the disclosure in which the methyl groups of the isopropoxy moiety of Formulas I-R and I-S are fully or partially deuterated (e.g., (D$_3$C)$_2$CHO—). Isotopic substitutions which may be made in the formation of homologs of the disclosure include non-radioactive (stable) atoms such as deuterium and carbon 13, as well as radioactive (unstable) atoms such as tritium, carbon 14, iodine 123, iodine 125, and the like.

A "solvate" is a similar composition except that a solvent other that water replaces the water. For example, methanol or ethanol can form an "alcoholate", which can again be stoichiometric or non-stoichiometric. As the term is used herein a "solvate" refers to a solid form, i.e., a compound in solution in a solvent, while it may be solvated, is not a solvate as the term is used herein.

In various embodiments, a compound for use in the disclosed methods has the structure of Formula I-R or I-S or is a pharmaceutically acceptable salt, homolog, hydrate or solvate thereof:

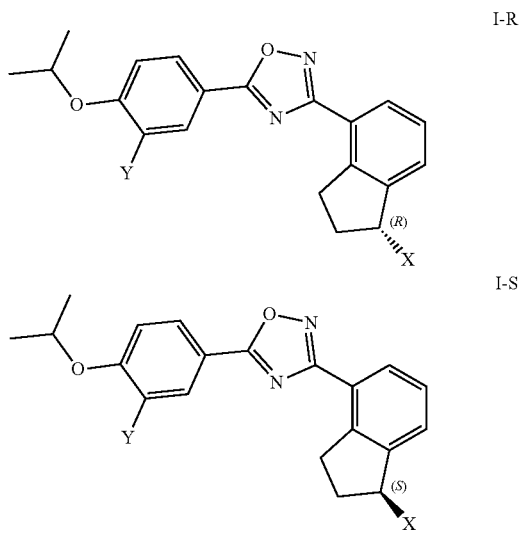

wherein
X is —NR'R" or —OR''' and Y is —CN, —Cl, or —CF$_3$;
R' is H, C$_{1-4}$ alkyl, n-hydroxy C$_{1-4}$ alkyl, —SO$_2$—R$^1$, or —CO—R$^1$;
R" is H, —SO$_2$—R$^3$, C$_{1-4}$ alkyl optionally substituted with 1 or more R$^2$, or a ring moiety optionally substituted with R$^4$ wherein such ring moiety is piperidinyl, cyclohexyl, morpholinyl, pyrrolidinyl, imidazolyl, or phenyl;
R''' is H, C$_{1-4}$ alkyl, or —CO—R$^1$;
or R' and R" taken together with the nitrogen atom to which they are bound form a 4, 5, or 6 membered saturated heterocyclic ring containing 0 or 1 additional heteroatoms where such additional heteroatom is O or N wherein such heterocycle is optionally singly or multiply substituted with substituents independently selected from —OH, oxo, —NH$_2$, n-hydroxy-C$_{1-4}$ alkyl, —COOH, —(CH$_2$)m-COOH, —(CH$_2$)m-COOR$^1$, —N(R$^1$R$^1$), and —(CH$_2$)m-CO—N(R$^5$R$^5$);

R$^1$ is, at each occurrence, C$_{1-4}$ alkyl or H;

R$^2$ is, at each occurrence, H, halo, OH, oxo, =NH, NH$_2$, —COOH, F, —NHR$^1$, —N(R$^5$R$^5$), —SO$_2$—R$^1$, —SO$_2$—N(R$^5$R$^5$1), —N(R$^1$)—SO$_2$—R$^1$, COOR$^1$, —OCO—R$^1$, —CO—N(R$^5$R$^5$), —N(R$^1$)—COR1, C$_{1-3}$ alkyl, C$_{1-3}$ alkoxy, and a ring moiety optionally substituted with R$^4$ wherein such ring moiety is piperazinyl, piperidinyl, morpholinyl, pyrrolidinyl, pyrazolyl, imidazolyl, benzimidazolyl, azetidinyl, cyclobutinyl, or phenyl;

R$^3$ is, at each occurrence, R$^2$, C$_{1-4}$ alkyl, C$_{3-6}$ cycloalkyl, or C$_{1-4}$ alkyl optionally substituted with 1 or more R$^2$;

R$^4$ is, at each occurrence, halo, OH, —NH$_2$, —NHR$^1$, —N(R$^1$R$^1$), COOH, —COOR$^1$, —NHCO—R$^1$;

R$^5$ is, at each occurrence, C$_{1-4}$ alkyl or H, or alternatively two R$^5$ taken together with the nitrogen atom to which they are bound can form a 4, 5, or 6 membered saturated heterocyclic ring containing 0 or 1 additional heteroatoms where such additional heteroatom is O or N wherein such heterocycle is optionally substituted with —OH, NH$_2$, —N(R$^1$R$^1$), n-hydroxy C$_{1-4}$ alkyl, —(CH$_2$)m-COOH, —(CH$_2$)m-COOR$^1$; and m is, at each occurrence, 0, 1, 2, or 3.

In more specific embodiments, the compound has the structure Formula II-R or II-S or is a pharmaceutically acceptable salt, homolog, hydrate or solvate thereof:

II-R

II-S wherein

R' is H, C$_{1-4}$ alkyl, n-hydroxy C$_{1-4}$ alkyl, —SO$_2$—R$^1$, or —CO—R$^1$;

R" is H, —(CR$^a$R$^b$)$_n$—R$^2$, Or —SO$_2$—R$^3$;

or R' and R" taken together with the nitrogen atom to which they are bound form a 4, 5, or 6 membered saturated heterocyclic ring containing 0 or 1 additional heteroatom where such additional heteroatom is O or N wherein such heterocycle is optionally singly or multiply substituted with —OH, —NH$_2$, n-hydroxy-C$_{1-4}$ alkyl, —COOH, —(CH$_2$)m-COOH, —(CH$_2$)m-COOR$^1$, —N(R$^1$R$^1$), —CO—N((R$^1$R$^1$);

each of R$^a$ and R$^b$ is, at each occurrence, H, hydroxyl or methyl;

or R$^a$ and R$^b$ bound to the same carbon are oxo;

R$^1$ is, at each occurrence, C$_{1-3}$ alkyl or H;

R$^2$ is, at each occurrence, H, OH, oxo, NH$_2$, —COOH, F, —NHR$^1$, —N(R$^1$R$^1$), —SO$_2$—R$^1$, —SO$_2$—N(R$^1$R$^1$), —COOR$^1$, —OCO—R$^1$, —CO—N(R$^1$R$^1$), C$_{1-3}$ alkyl, C$_{1-3}$ alkoxy, piperazinyl, piperidinyl, morpholinyl, pyrrolidinyl, imidazolyl, or phenyl optionally substituted with R$^4$;

R$^3$ is, at each occurrence, —(CR$^a$R$^b$)—R$^2$ or C$_{1-4}$ alkyl;

R$^4$ is, at each occurrence, halo, OH, —NH$_2$, —NHR$^1$, —N(R$^1$R$^1$), —COOH, —COOR$^1$, or —NHCO—R$^1$;

n is, at each occurrence, 1, 2, or 3;

m is, at each occurrence, 0, 1, 2, or 3; and p is, at each occurrence, 0, 1, 2, or 3.

In various embodiments the disclosure provides compounds where Y is Cl, in other embodiments the disclosure provides compounds where Y is CF$_3$ and in other embodiments the disclosure provides compounds where Y is CN.

In various embodiments the disclosure provides compounds where X is —NR'R", in other embodiments the disclosure provides compounds where X is —OR"'.

In various embodiments the disclosure provides compounds where X is —OR"'.

In various embodiments the disclosure provides compounds where X is —OH and in other embodiments the disclosure provides compounds where X is —OCO—R$^1$.

In various embodiments the disclosure provides compounds where R$^1$ is C$_{1-3}$ alkyl; in other embodiments the disclosure provides compounds where R' is H.

In various embodiments the disclosure provides compounds where R' is —COR; in other embodiments the disclosure provides compounds where R' is SO$_2$—R$^1$.

In various embodiments the disclosure provides compounds where R" is H.

In various embodiments the disclosure provides compounds where R" is —SO$_2$—R$^3$; in other embodiments the disclosure provides compounds where R" is C$_{1-4}$ alkyl where the C$_{1-4}$ alkyl is optionally substituted with 1 or more substituents defined by R$^2$.

In various embodiments the disclosure provides compounds where R" is —(CR$^a$R$^b$)$_n$—R$^2$ and each R$^a$ and each R$^b$ can be independently any of H, hydroxyl and methyl or where R$^a$ and R$^b$ are bound to the same carbon they can be taken together to form oxo (i.e. with the carbon to which they are bound forming a carbonyl moiety). In various such embodiments, n can be 0, 1, 2, or 3 and in various embodiments n is 2. In various such embodiments R$^2$ can be —OH, —NH$_2$, —NHR$^1$, —N(R$^5$R$^5$), or —COOH.

In various embodiments the disclosure provides compounds where R$^3$ is C$_{1-4}$ alkyl optionally substituted with 1 or more R$^2$.

In various embodiments the disclosure provides compounds where R$^2$ is OH; in other embodiments the disclosure provides compounds where R$^2$ is C$_{1-3}$ alkoxy.

In various embodiments the disclosure provides compounds where R$^3$ is (CH$_2$)$_2$—OR.

In various embodiments the disclosure provides compounds where Y is CN and X is —NH—SO$_2$—R$^3$. In various embodiments the disclosure provides compounds where R$^3$ is —C$_2$H$_5$—N((R$^5$R$^5$) or —CH$_2$—CO—N(R$^5$R$^5$). In various embodiments the disclosure provides compounds where Y is CN and X is —NH—CO—N(R$^5$R$^5$).

In various embodiments X is —NH$_2$ and in various of such embodiments Y is CN.

In various embodiments the disclosure provides compounds where Y is Cl, in other embodiments the disclosure provides compounds where Y is $CF_3$ and in other embodiments the disclosure provides compounds where Y is CN.

In various embodiments the disclosure provides compounds where X is —NR'R", in other embodiments the disclosure provides compounds where X is —OR'".

In various embodiments the disclosure provides compounds where X is —OR'".

In various embodiments the disclosure provides compounds where X is —OH and in other embodiments the disclosure provides compounds where X is —OCO—$R^1$.

In various embodiments the disclosure provides compounds where $R^1$ is $C_{1-3}$ alkyl; in other embodiments the disclosure provides compounds where R' is H.

In various embodiments the disclosure provides compounds where R' is —$COR^1$; in other embodiments the disclosure provides compounds where R' is $SO_2$—$R^1$.

In various embodiments the disclosure provides compounds where R" is H.

In various embodiments the disclosure provides compounds where R" is —$SO_2$—$R^3$; in other embodiments the disclosure provides compounds where R" is $C_{1-4}$ alkyl where the $C_{1-4}$ alkyl is optionally substituted with 1 or more substituents defined by $R^2$.

In various embodiments the disclosure provides compounds where R" is —$(CR^aR^b)_n$—$R^2$ and each $R^a$ and each $R^b$ can be independently any of H, hydroxyl and methyl or where $R^a$ and $R^b$ are bound to the same carbon they can be taken together to form oxo (i.e. with the carbon to which they are bound forming a carbonyl moiety). In various such embodiments, n can be 0, 1, 2, or 3 and in various embodiments n is 2. In various such embodiments $R^2$ can be —OH, —$NH_2$, —$NHR^1$, —$N(R^5R^5)$, or —COOH.

In various embodiments the disclosure provides compounds where $R^3$ is $C_{1-4}$ alkyl optionally substituted with 1 or more $R^2$.

In various embodiments the disclosure provides compounds where $R^2$ is OH; in other embodiments the disclosure provides compounds where $R^2$ is $C_{1-3}$ alkoxy.

In various embodiments the disclosure provides compounds where $R^3$ is $(CH_2)_2$—OR.

In various embodiments the disclosure provides compounds where Y is CN and X is —NH—$SO_2$—$R^3$. In various embodiments the disclosure provides compounds where $R^3$ is —$C_2H_5$—$N((R^5R^5)$ or —$CH_2$—CO—$N(R^5R^5)$. In various embodiments the disclosure provides compounds where Y is CN and X is —NH—CO—$N(R^5R^5)$.

In various embodiments X is —$NH_2$ and in various of such embodiments Y is CN.

In more specific embodiments, the compound is one or more compounds listed in Table 1 below, or a pharmaceutically acceptable salt, homolog, hydrate or solvate thereof.

TABLE 1

Representative Compounds

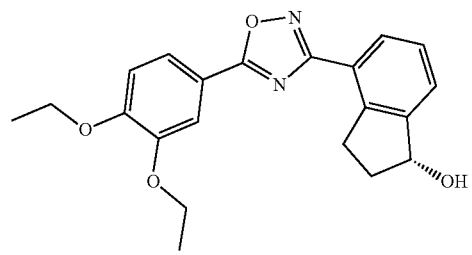 [SMILES: CCOc1ccc(-c2nc(-c3cccc4c3CC[C@H]4O)no2)cc1OCC]

1

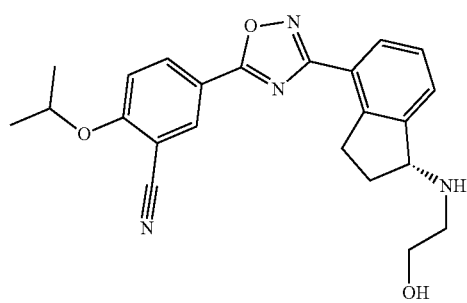 [SMILES: CC(C)Oc1ccc(-c2nc(-c3cccc4c3CC[C@H]4NCCO)no2)cc1C#N]

2

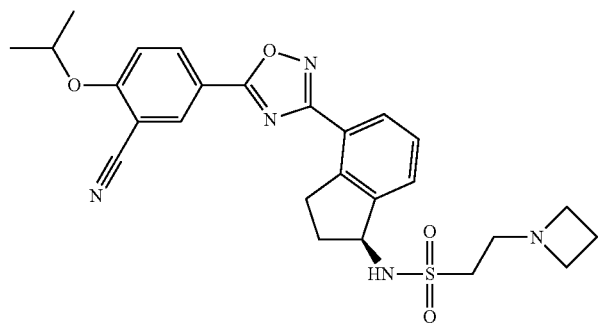 [SMILES: CC(C)Oc1ccc(-c2nc(-c3cccc4c3CC[C@@H]4NS(=O)(=O)CCN3CCC3)no2)cc1C#N]

3

TABLE 1-continued
Representative Compounds
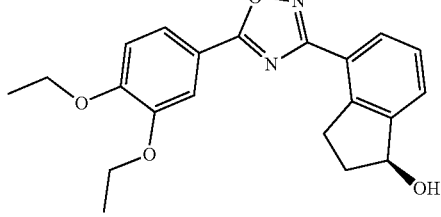
4
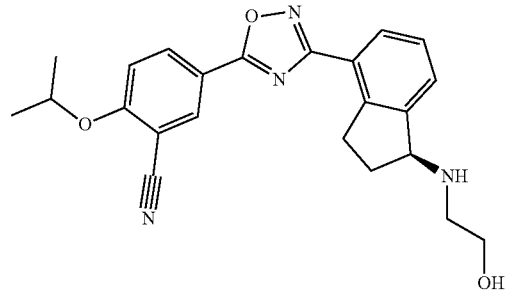 [SMILES: CC(C)Oc1ccc(-c2nc(-c3cccc4c3CC[C@@H]4NCCO)no2)cc1CN]
5
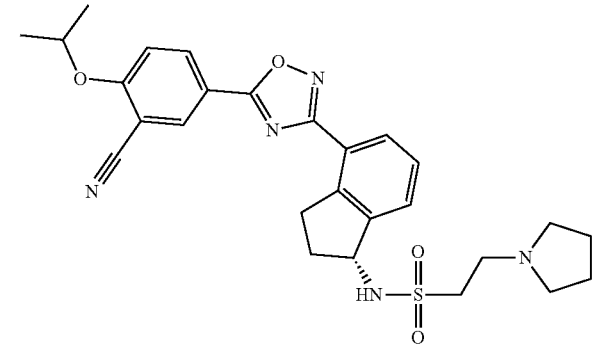 [SMILES: CC(C)Oc1ccc(-c2nc(-c3cccc4c3CC[C@H]4NS(=O)(=O)CCN3CCCC3)no2)cc1C#N]
6
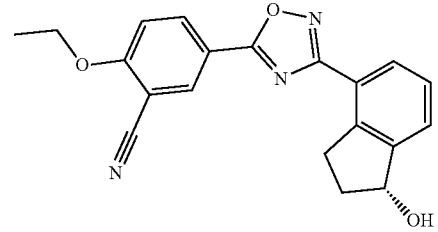 [SMILES: CCOc1ccc(-c2nc(-c3cccc4c3CC[C@H]4O)no2)cc1C#N]
7
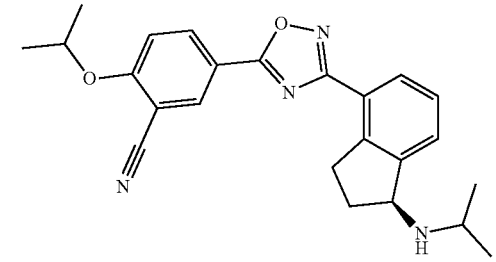 [SMILES: CC(C)N[C@H]1CCc2c(-c3noc(-c4ccc(OC(C)C)c(C#N)c4)n3)cccc21]
8

TABLE 1-continued

Representative Compounds

TABLE 1-continued

Representative Compounds

TABLE 1-continued
Representative Compounds
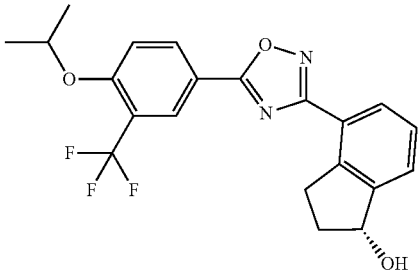 [SMILES: CC(C)Oc1ccc(-c2nc(-c3cccc4c3CC[C@H]4O)no2)cc1C(F)(F)F]
19
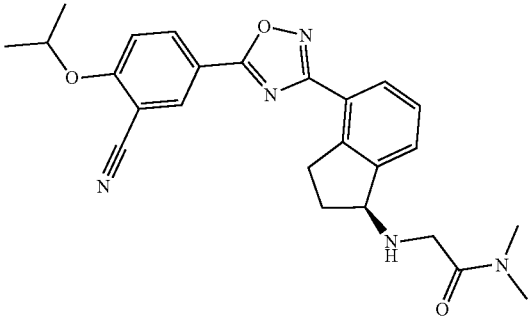 [SMILES: CC(C)Oc1ccc(-c2nc(-c3cccc4c3CC[C@@H]4NCC(=O)N(C)C)no2)cc1C#N]
20
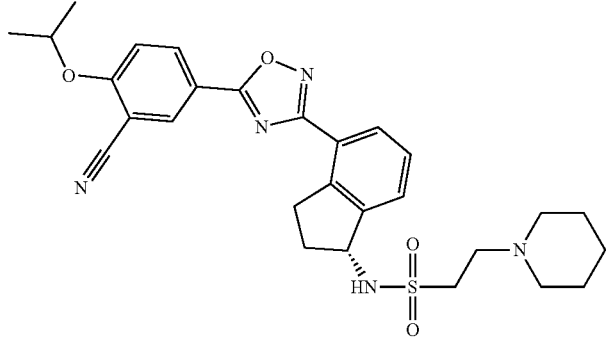 [SMILES: CC(C)Oc1ccc(-c2nc(-c3cccc4c3CC[C@H]4NS(=O)(=O)CCN3CCCCC3)no2)cc1C#N]
21
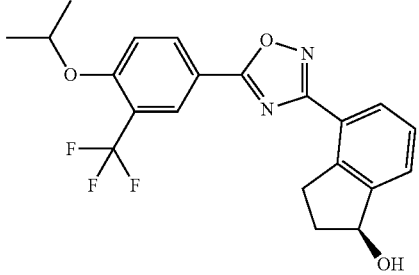 [SMILES: CC(C)Oc1ccc(-c2nc(-c3cccc4c3CC[C@@H]4O)no2)cc1C(F)(F)F]
22
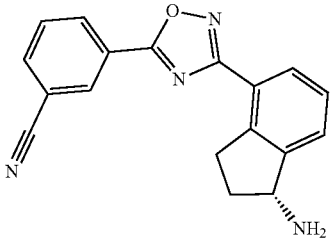 [SMILES: N#Cc1cccc(-c2nc(-c3cccc4c3CC[C@H]4N)no2)c1]
23

TABLE 1-continued
Representative Compounds
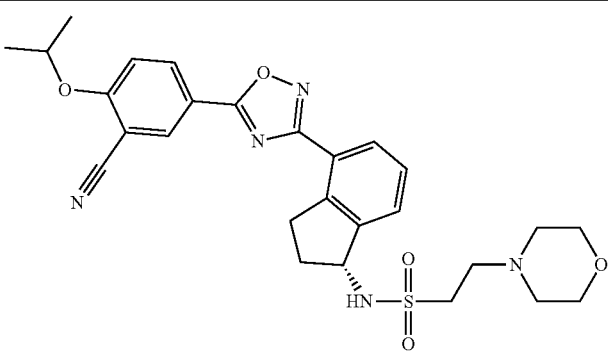
24
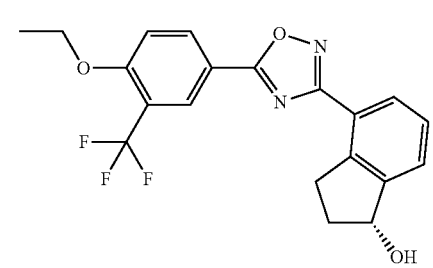 [SMILES: CCOc1ccc(-c2nc(-c3cccc4c3CC[C@H]4O)no2)cc1C(F)(F)F]
25
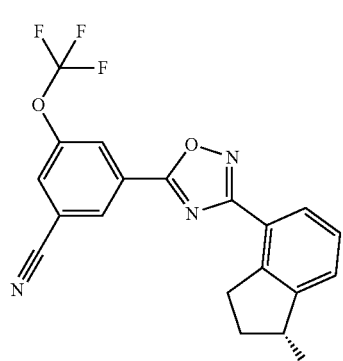
26
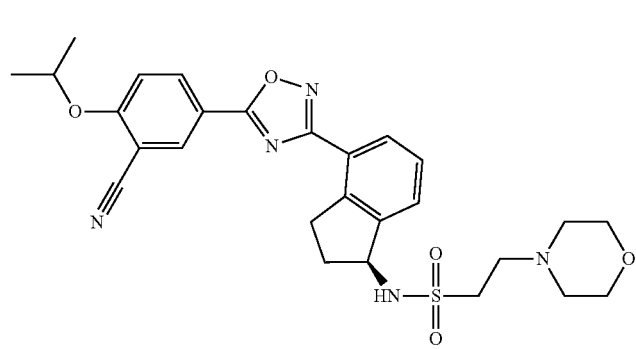 [SMILES: CC(C)Oc1ccc(-c2nc(-c3cccc4c3CC[C@@H]4NS(=O)(=O)CCN3CCOCC3)no2)cc1C#N]
27
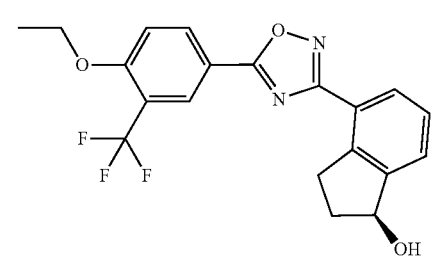 [SMILES: CCOc1ccc(-c2nc(-c3cccc4c3CC[C@@H]4O)no2)cc1C(F)(F)F]
28

TABLE 1-continued
Representative Compounds
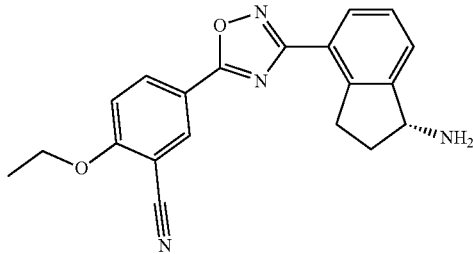 [SMILES: CCOc1ccc(-c2nc(-c3cccc4c3CC[C@H]4N)no2)cc1C#N]
29
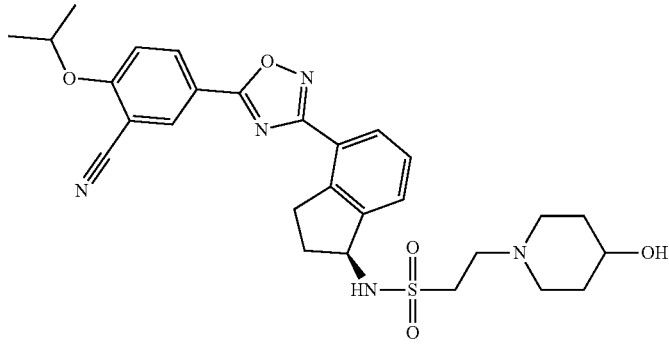 [SMILES: CC(C)Oc1ccc(-c2nc(-c3cccc4c3CC[C@@H]4NS(=O)(=O)CCN3CCC(O)CC3)no2)cc1C#N]
30
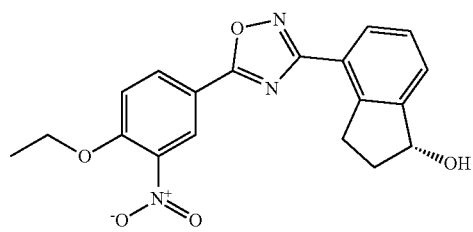
31
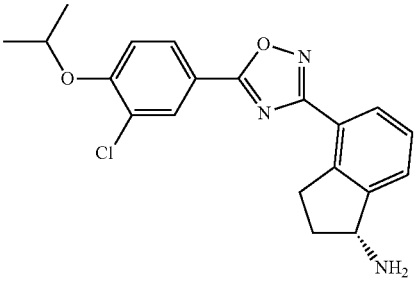 [SMILES: CC(C)Oc1ccc(-c2nc(-c3cccc4c3CC[C@H]4N)no2)cc1Cl]
32
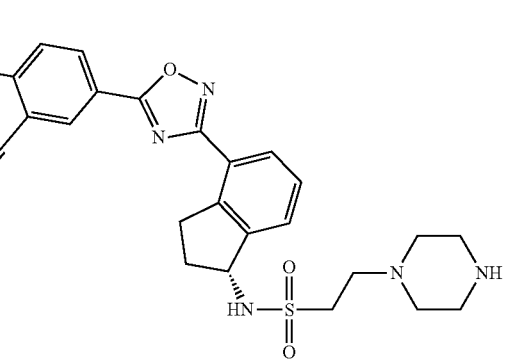
33

TABLE 1-continued

Representative Compounds

| | |
|---|---|
| (structure) | 34 |
| (structure) | 35 |
| (structure) | 36 |
| (structure) | 37 |
| (structure) | 38 |

TABLE 1-continued

Representative Compounds

| | |
|---|---|
| (structure) | 39 |
| (structure) | 40 |
| (structure) | 41 |
| (structure) | 42 |
| (structure) | 43 |

TABLE 1-continued
Representative Compounds
44
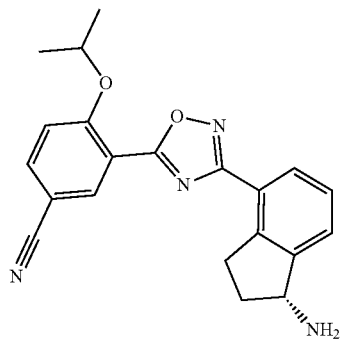 [SMILES: CC(C)Oc1ccc(C#N)cc1-c1nc(-c2cccc3c2CC[C@H]3N)no1]
45
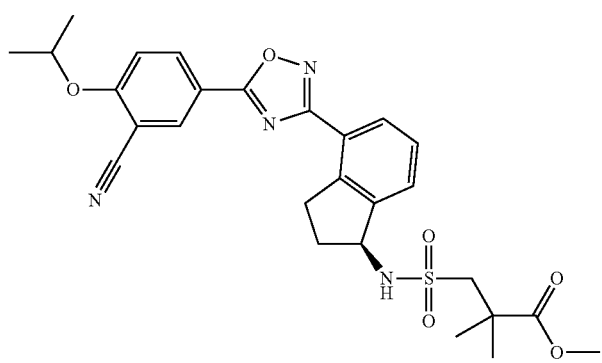 [SMILES: COC(=O)C(C)(C)CS(=O)(=O)N[C@H]1CCc2c(-c3noc(-c4ccc(OC(C)C)c(C#N)c4)n3)cccc21]
46
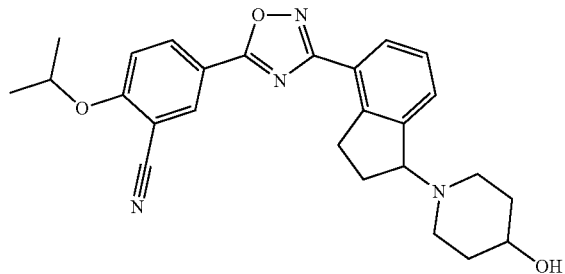 [SMILES: CC(C)Oc1ccc(-c2nc(-c3cccc4c3CCC4N3CCC(O)CC3)no2)cc1C#N]
47
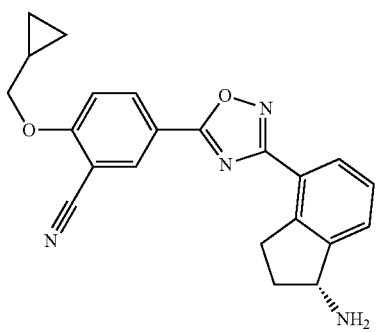 [SMILES: N#Cc1cc(-c2nc(-c3cccc4c3CC[C@H]4N)no2)ccc1OCC1CC1]
48
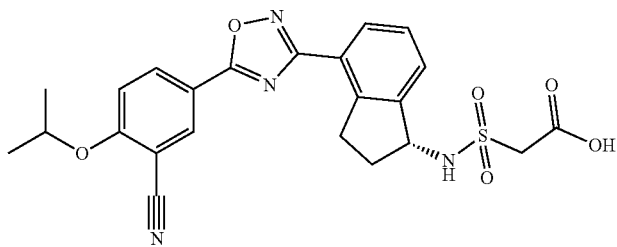 [SMILES: CC(C)Oc1ccc(-c2nc(-c3cccc4c3CC[C@H]4NS(=O)(=O)CC(=O)O)no2)cc1CN]

TABLE 1-continued
Representative Compounds
| | |
|---|---|
| 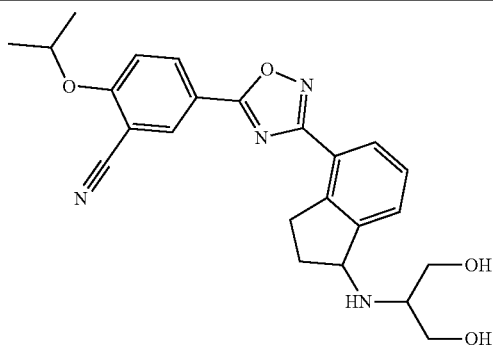 | 49 |
| 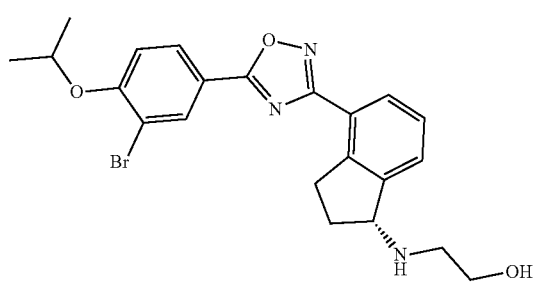 [SMILES: CC(C)Oc1ccc(-c2nc(-c3cccc4c3CC[C@H]4NCCO)no2)cc1Br] | 50 |
| 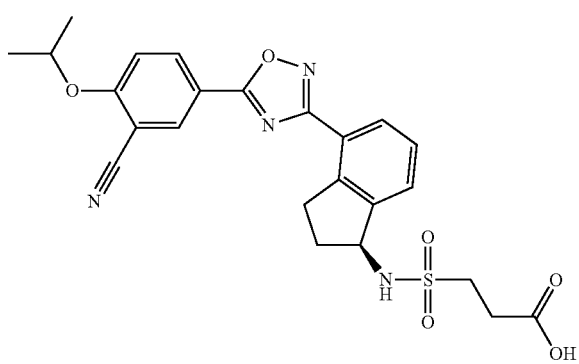 [SMILES: CC(C)Oc1ccc(-c2nc(-c3cccc4c3CC[C@@H]4NS(=O)(=O)CCC(=O)O)no2)cc1C#N] | 51 |
| 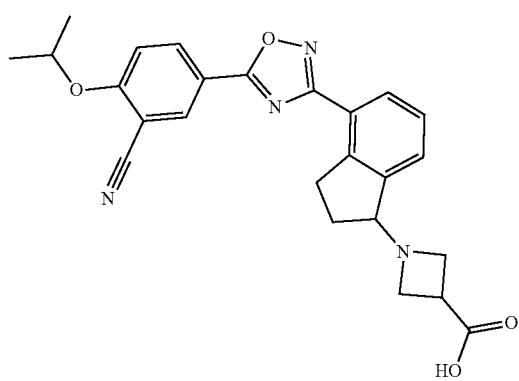 [SMILES: CC(C)Oc1ccc(-c2nc(-c3cccc4c3CCC4N3CC(C(=O)O)C3)no2)cc1C#N] | 52 |
| 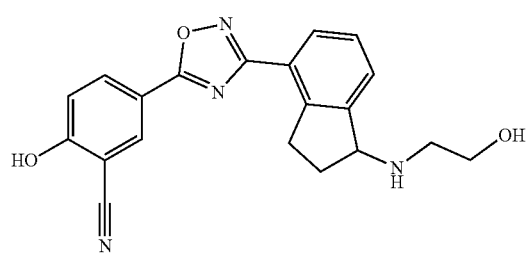 [SMILES: N#Cc1cc(-c2nc(-c3cccc4c3CCC4NCCO)no2)ccc1O] | 53 |

TABLE 1-continued
Representative Compounds
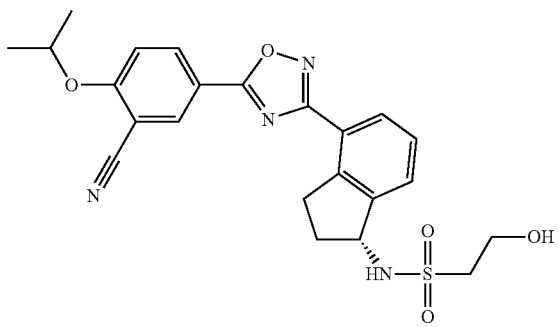 [SMILES: CC(C)Oc1ccc(-c2nc(-c3cccc4c3CC[C@H]4NS(=O)(=O)CCO)no2)cc1C#N]
54
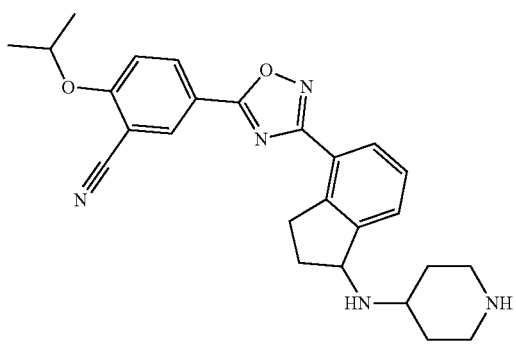 [SMILES: CC(C)Oc1ccc(-c2nc(-c3cccc4c3CCC4NC3CCNCC3)no2)cc1C#N]
55
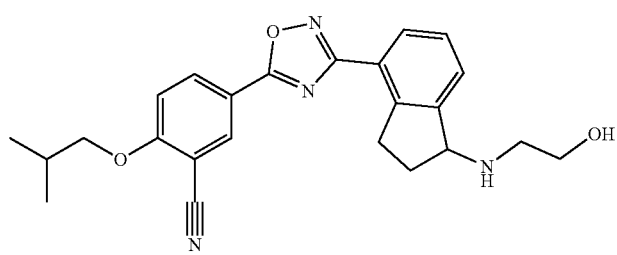 [SMILES: CC(C)COc1ccc(-c2nc(-c3cccc4c3CCC4NCCO)no2)cc1CN]
56
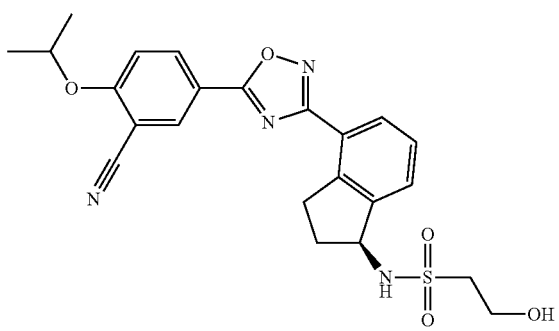 [SMILES: CC(C)Oc1ccc(-c2nc(-c3cccc4c3CC[C@@H]4NS(=O)(=O)CCO)no2)cc1C#N]
57
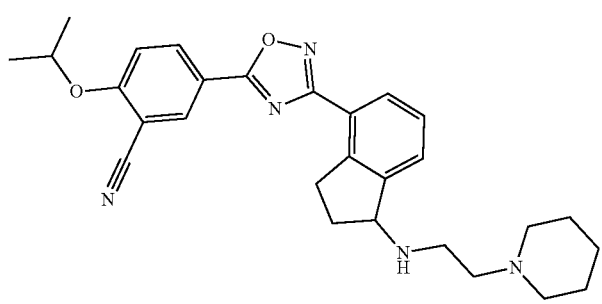 [SMILES: CC(C)Oc1ccc(-c2nc(-c3cccc4c3CCC4NCCN3CCCCC3)no2)cc1C#N]
58

TABLE 1-continued

Representative Compounds

| | |
|---|---|
| (structure) | 59 |
| (structure) | 60 |
| (structure) | 61 |
| (structure) | 62 |
| (structure) | 63 |

TABLE 1-continued

Representative Compounds

| | |
|---|---|
| (structure) | 64 |
| (structure) | 65 |
| (structure) | 66 |
| (structure) | 67 |
| (structure) | 68 |

TABLE 1-continued
Representative Compounds
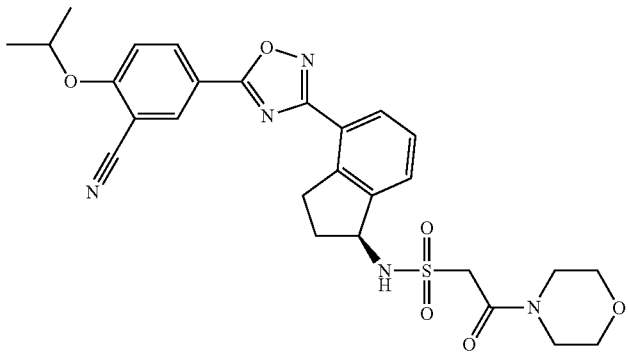 [SMILES: CC(C)Oc1ccc(-c2nc(-c3cccc4c3CC[C@@H]4NS(=O)(=O)CC(=O)N3CCOCC3)no2)cc1C#N]
69
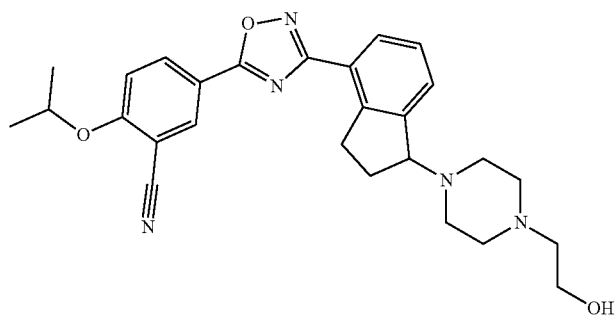 [SMILES: CC(C)Oc1ccc(-c2nc(-c3cccc4c3CCC4N3CCN(CCO)CC3)no2)cc1C#N]
70
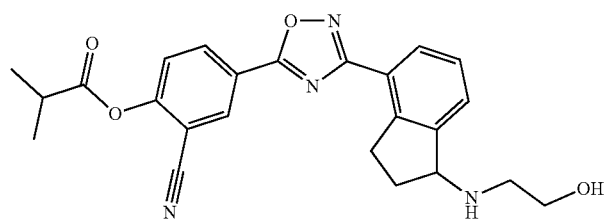 [SMILES: CC(C)C(=O)Oc1ccc(-c2nc(-c3cccc4c3CCC4NCCO)no2)cc1C#N]
71
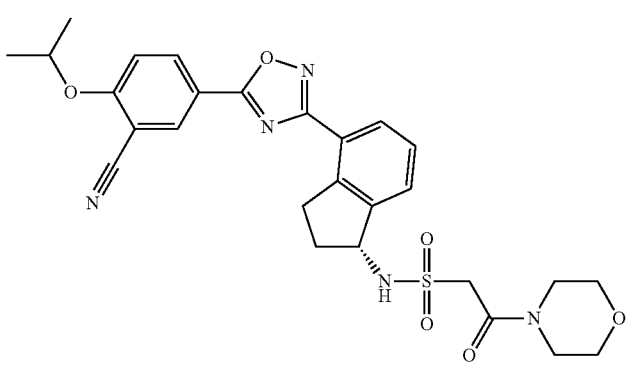 [SMILES: CC(C)Oc1ccc(-c2nc(-c3cccc4c3CC[C@H]4NS(=O)(=O)CC(=O)N3CCOCC3)no2)cc1C#N]
72

TABLE 1-continued
Representative Compounds
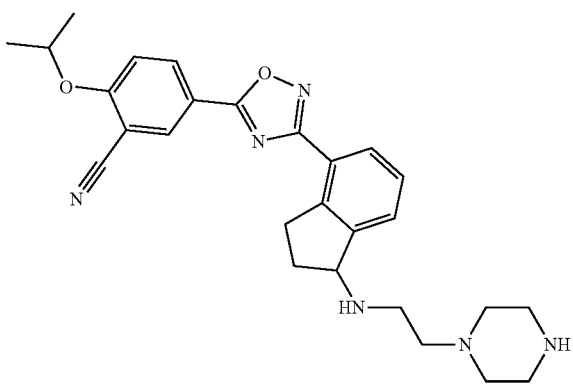 [SMILES: CC(C)Oc1ccc(-c2nc(-c3cccc4c3CCC4NCCN3CCNCC3)no2)cc1C#N]
73
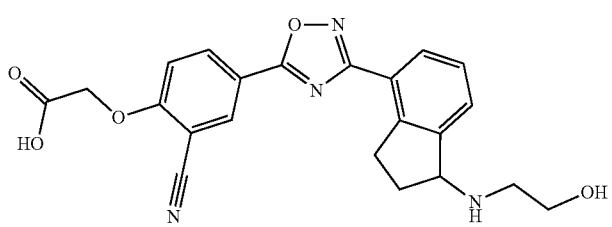 [SMILES: N#Cc1cc(-c2nc(-c3cccc4c3CCC4NCCO)no2)ccc1OCC(=O)O]
74
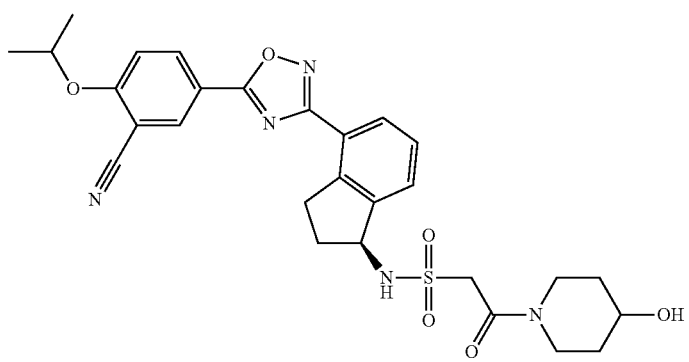 [SMILES: CC(C)Oc1ccc(-c2nc(-c3cccc4c3CC[C@@H]4NS(=O)(=O)CC(=O)N3CCC(O)CC3)no2)cc1C#N]
75
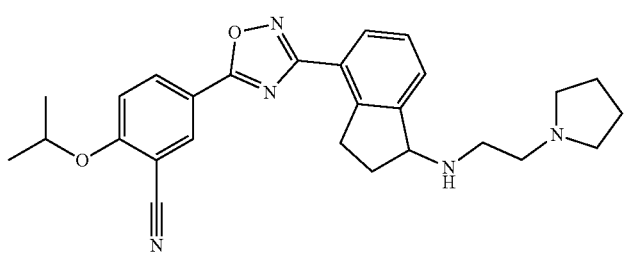 [SMILES: CC(C)Oc1ccc(-c2nc(-c3cccc4c3CCC4NCCN3CCCC3)no2)cc1C#N]
76
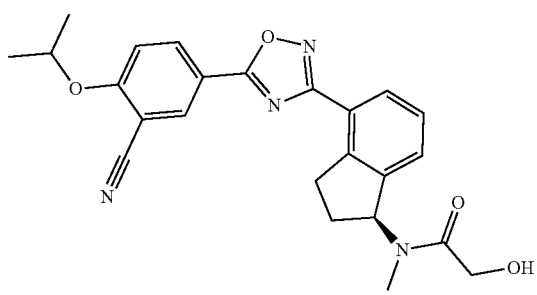 [SMILES: CC(C)Oc1ccc(-c2nc(-c3cccc4c3CC[C@@H]4N(C)C(=O)CO)no2)cc1C#N]
77

TABLE 1-continued

Representative Compounds

| | |
|---|---|
| (structure) | 78 |
| (structure) | 79 |
| (structure) | 80 |
| (structure) | 81 |
| (structure) | 82 |

TABLE 1-continued

Representative Compounds

| | |
|---|---|
| [Structure] | 83 |
| [Structure] | 84 |
| [Structure] | 85 |
| [Structure] | 86 |
| [Structure] | 87 |

TABLE 1-continued

Representative Compounds

| | |
|---|---|
| (structure) | 88 |
| (structure) | 89 |
| (structure) | 90 |
| (structure) | 91 |
| (structure) | 92 |

TABLE 1-continued
Representative Compounds
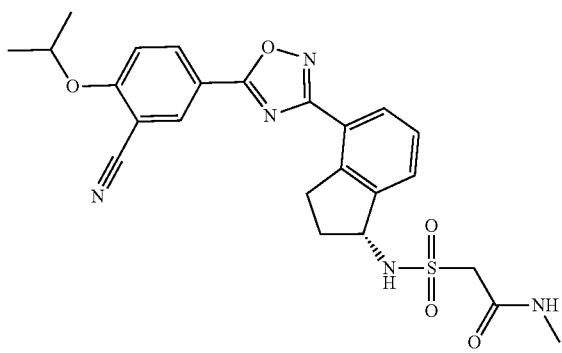 [SMILES: CNC(=O)CS(=O)(=O)N[C@@H]1CCc2c(-c3noc(-c4ccc(OC(C)C)c(C#N)c4)n3)cccc21]
93
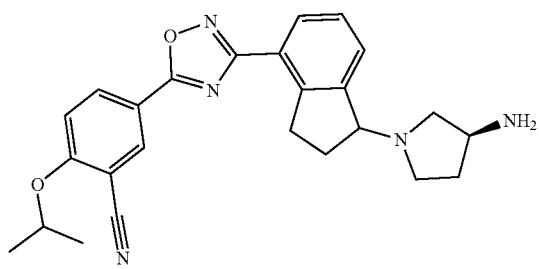 [SMILES: CC(C)Oc1ccc(-c2nc(-c3cccc4c3CCC4N3CC[C@H](N)C3)no2)cc1C#N]
94
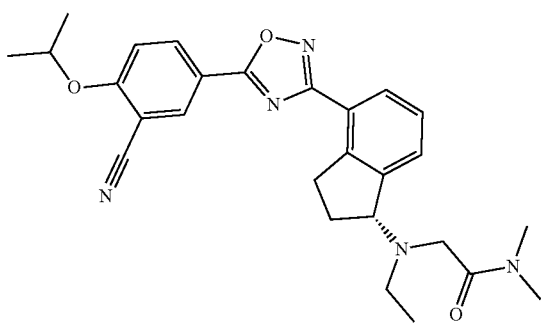 [SMILES: CCN(CC(=O)N(C)C)[C@@H]1CCc2c(-c3noc(-c4ccc(OC(C)C)c(C#N)c4)n3)cccc21]
95
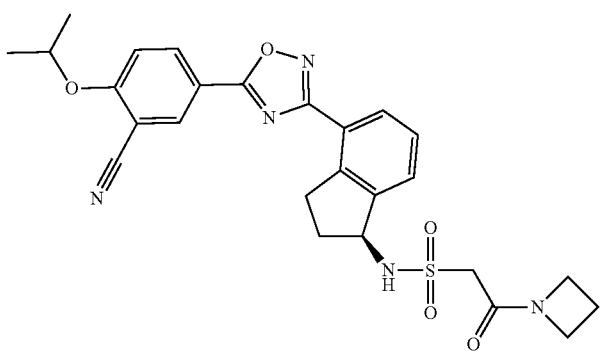 [SMILES: CC(C)Oc1ccc(-c2nc(-c3cccc4c3CC[C@@H]4NS(=O)(=O)CC(=O)N3CCC3)no2)cc1C#N]
96
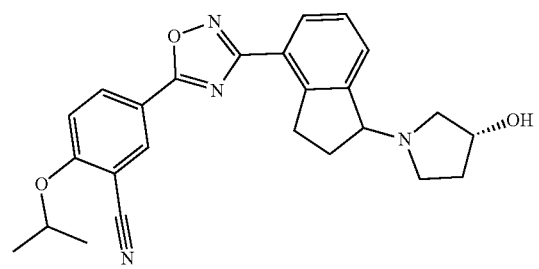 [SMILES: CC(C)Oc1ccc(-c2nc(-c3cccc4c3CCC4N3CC[C@@H](O)C3)no2)cc1C#N]
97

TABLE 1-continued
Representative Compounds
| | |
|---|---|
| 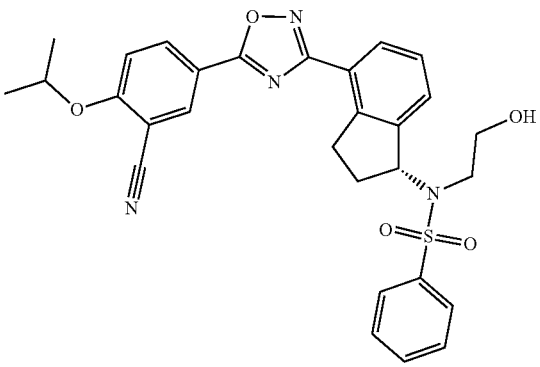 [SMILES: CC(C)Oc1ccc(-c2nc(-c3cccc4c3CC[C@H]4N(CCO)S(=O)(=O)c3ccccc3)no2)cc1C#N] | 98 |
| 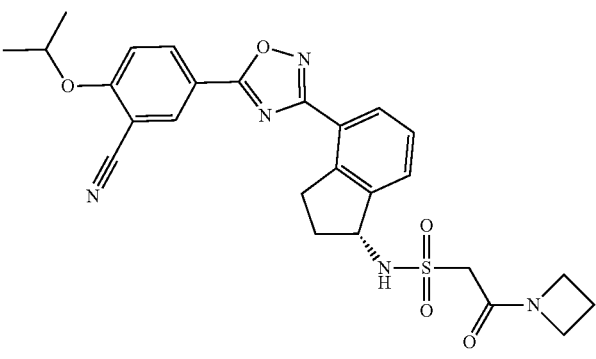 [SMILES: CC(C)Oc1ccc(-c2nc(-c3cccc4c3CC[C@H]4NS(=O)(=O)CC(=O)N3CCC3)no2)cc1C#N] | 99 |
| 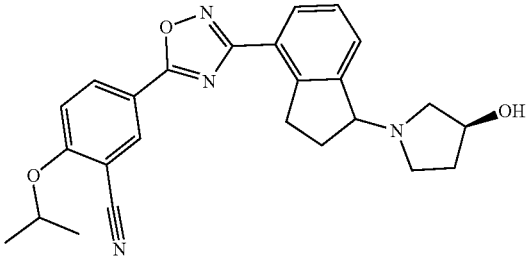 [SMILES: CC(C)Oc1ccc(-c2nc(-c3cccc4c3CCC4N3CC[C@H](O)C3)no2)cc1C#N] | 100 |
| 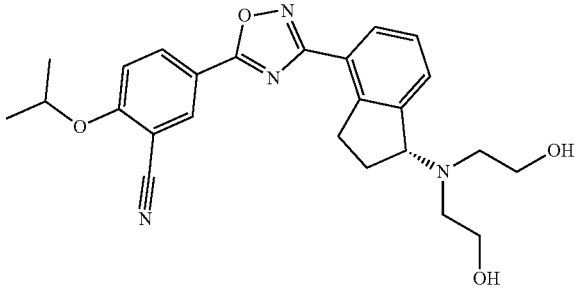 [SMILES: CC(C)Oc1ccc(-c2nc(-c3cccc4c3CC[C@H]4N(CCO)CCO)no2)cc1C#N] | 101 |
| 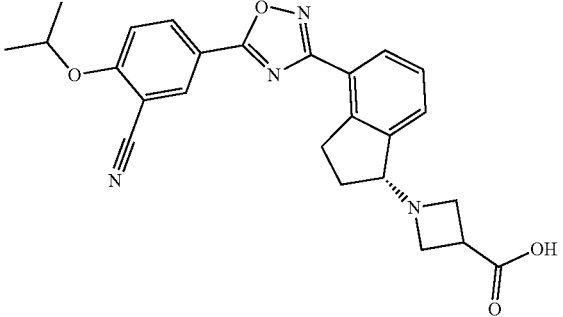 [SMILES: CC(C)Oc1ccc(-c2nc(-c3cccc4c3CC[C@H]4N3CC(C(=O)O)C3)no2)cc1C#N] | 102 |

TABLE 1-continued
Representative Compounds
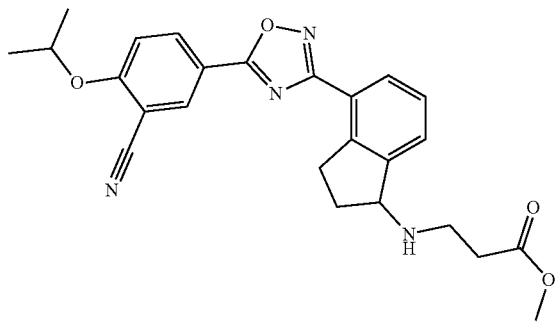 [SMILES: COC(=O)CCNC1CCc2c(-c3noc(-c4ccc(OC(C)C)c(C#N)c4)n3)cccc21]
103
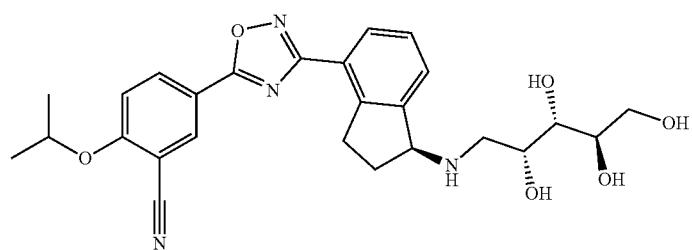 [SMILES: CC(C)Oc1ccc(-c2nc(-c3cccc4c3CC[C@@H]4NC[C@@H](O)[C@H](O)[C@H](O)CO)no2)cc1C#N]
104
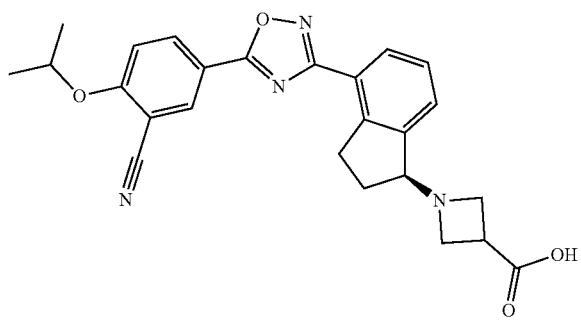 [SMILES: CC(C)Oc1ccc(-c2nc(-c3cccc4c3CC[C@@H]4N3CC(C(=O)O)C3)no2)cc1C#N]
105
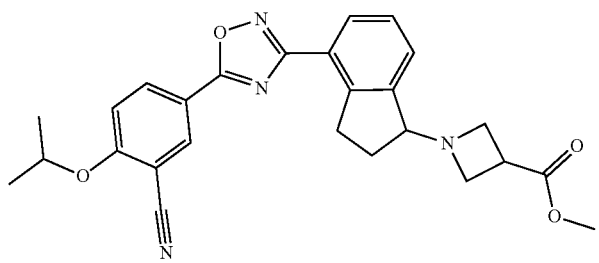 [SMILES: COC(=O)C1CN(C2CCc3c(-c4noc(-c5ccc(OC(C)C)c(C#N)c5)n4)cccc32)C1]
106
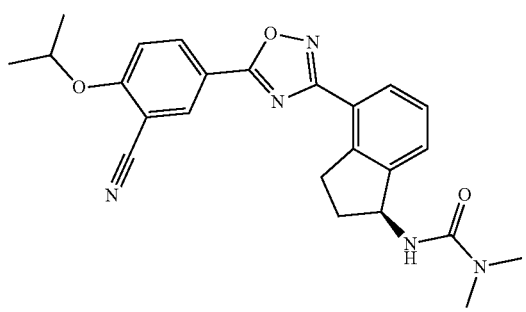 [SMILES: CC(C)Oc1ccc(-c2nc(-c3cccc4c3CC[C@@H]4NC(=O)N(C)C)no2)cc1C#N]
107

TABLE 1-continued
Representative Compounds
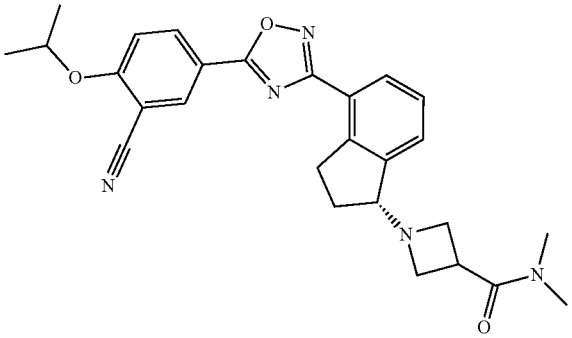 [SMILES: CC(C)Oc1ccc(-c2nc(-c3cccc4c3CC[C@H]4N3CC(C(=O)N(C)C)C3)no2)cc1C#N]
108
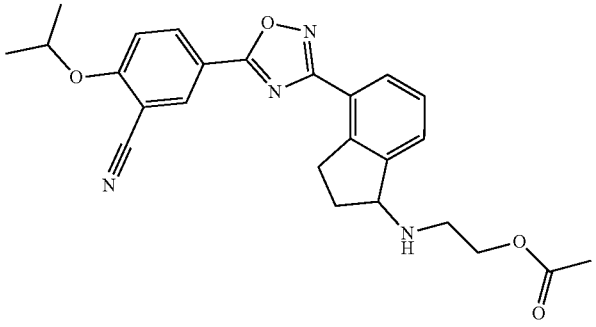 [SMILES: CC(=O)OCCNC1CCc2c(-c3noc(-c4ccc(OC(C)C)c(C#N)c4)n3)cccc21]
109
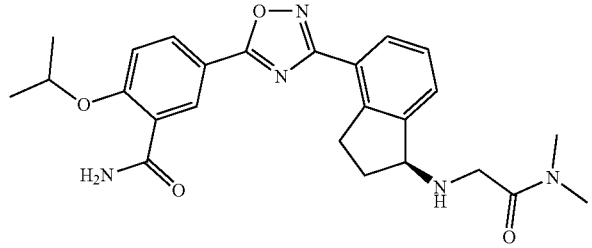 [SMILES: CC(C)Oc1ccc(-c2nc(-c3cccc4c3CC[C@@H]4NCC(=O)N(C)C)no2)cc1C(N)=O]
110
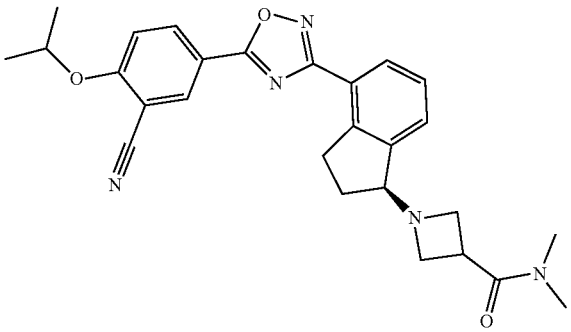 [SMILES: CC(C)Oc1ccc(-c2nc(-c3cccc4c3CC[C@@H]4N3CC(C(=O)N(C)C)C3)no2)cc1C#N]
111
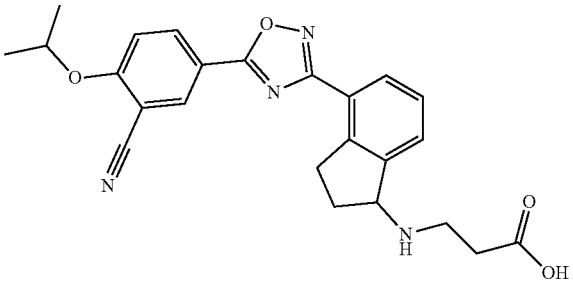 [SMILES: CC(C)Oc1ccc(-c2nc(-c3cccc4c3CCC4NCCC(=O)O)no2)cc1C#N]
112

TABLE 1-continued

Representative Compounds

| | |
|---|---|
| (structure) | 113 |
| (structure) | 114 |
| (structure) | 115 |
| (structure) | 116 |
| (structure) | 117 |

TABLE 1-continued

Representative Compounds

| | |
|---|---|
| (structure) | 118 |
| (structure) | 119 |
| (structure) | 120 |
| (structure) | 121 |
| (structure) | 122 |

TABLE 1-continued

Representative Compounds

123

124

125

126

127

TABLE 1-continued
Representative Compounds
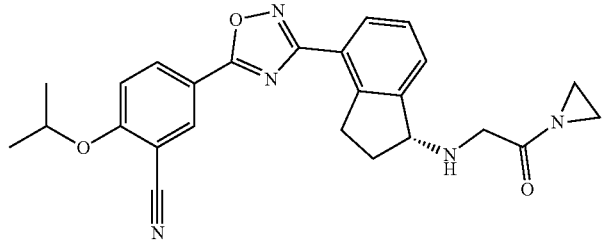 [SMILES: CC(C)Oc1ccc(-c2nc(-c3cccc4c3CC[C@H]4NCC(=O)N3CC3)no2)cc1C#N]
128
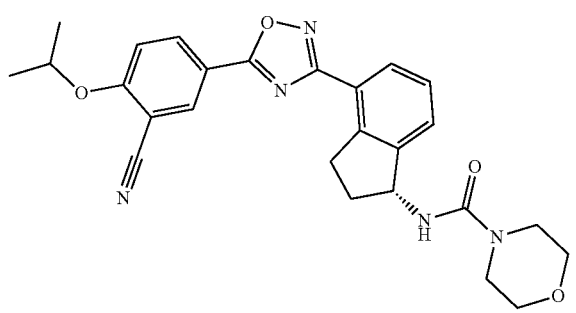 [SMILES: CC(C)Oc1ccc(-c2nc(-c3cccc4c3CC[C@H]4NC(=O)N3CCOCC3)no2)cc1C#N]
129
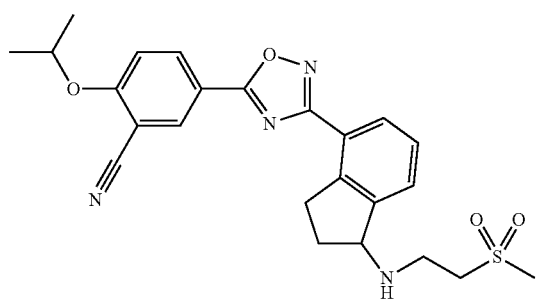 [SMILES: CC(C)Oc1ccc(-c2nc(-c3cccc4c3CCC4NCCS(C)(=O)=O)no2)cc1C#N]
130
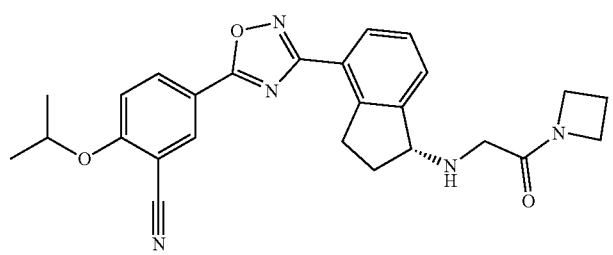 [SMILES: CC(C)Oc1ccc(-c2nc(-c3cccc4c3CC[C@H]4NCC(=O)N3CCC3)no2)cc1C#N]
131
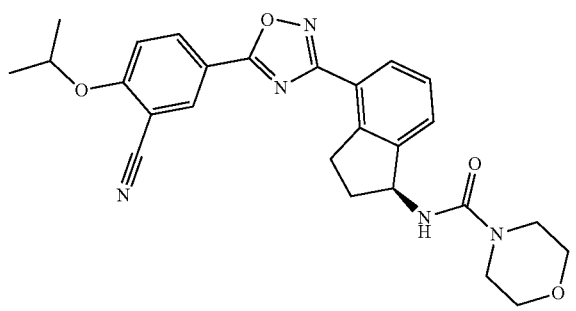 [SMILES: CC(C)Oc1ccc(-c2nc(-c3cccc4c3CC[C@@H]4NC(=O)N3CCOCC3)no2)cc1C#N]
132

TABLE 1-continued
Representative Compounds
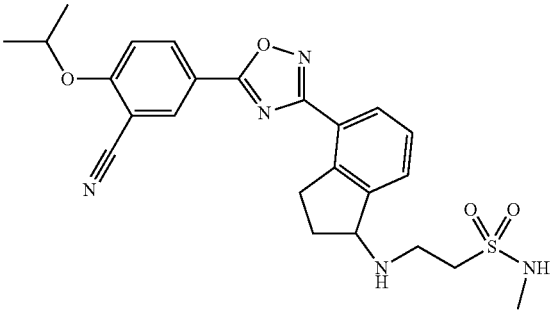 [SMILES: CNS(=O)(=O)CCNC1CCc2c(-c3noc(-c4ccc(OC(C)C)c(C#N)c4)n3)cccc21]
133
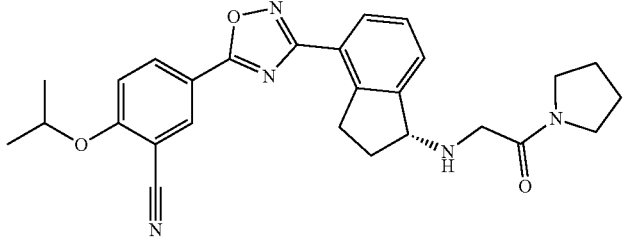 [SMILES: CC(C)Oc1ccc(-c2nc(-c3cccc4c3CC[C@H]4NCC(=O)N3CCCC3)no2)cc1C#N]
134
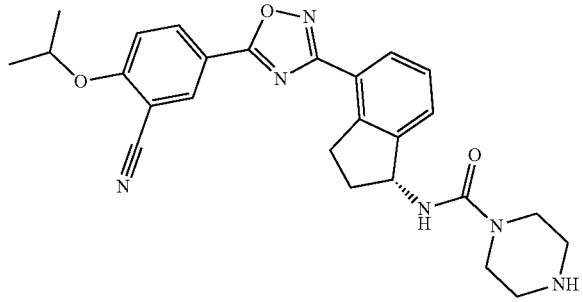 [SMILES: CC(C)Oc1ccc(-c2nc(-c3cccc4c3CC[C@H]4NC(=O)N3CCNCC3)no2)cc1C#N]
135
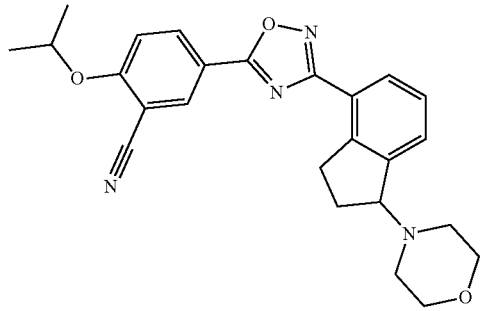
136
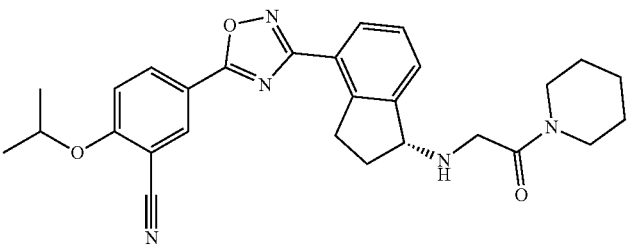 [SMILES: CC(C)Oc1ccc(-c2nc(-c3cccc4c3CC[C@H]4NCC(=O)N3CCCCC3)no2)cc1C#N]
137

TABLE 1-continued
Representative Compounds
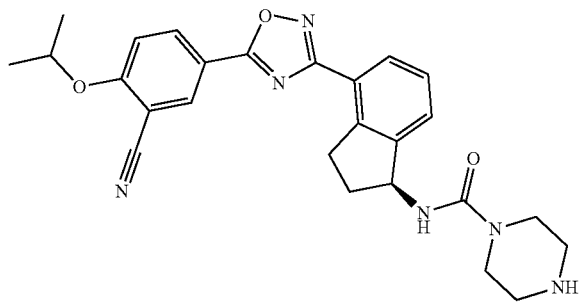 [SMILES: CC(C)Oc1ccc(-c2nc(-c3cccc4c3CC[C@@H]4NC(=O)N3CCNCC3)no2)cc1C#N]
138
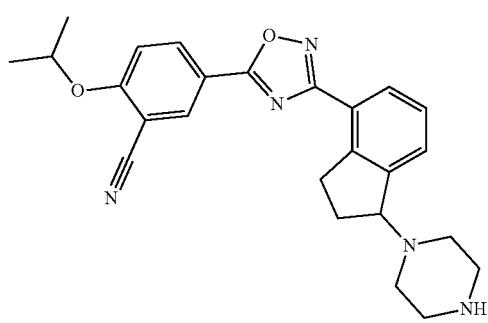 [SMILES: CC(C)Oc1ccc(-c2nc(-c3cccc4c3CCC4N3CCNCC3)no2)cc1C#N]
139
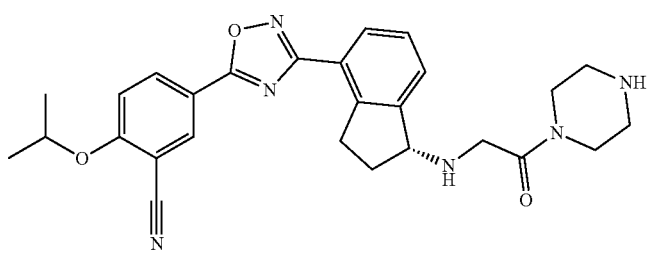 [SMILES: CC(C)Oc1ccc(-c2nc(-c3cccc4c3CC[C@H]4NCC(=O)N3CCNCC3)no2)cc1C#N]
140
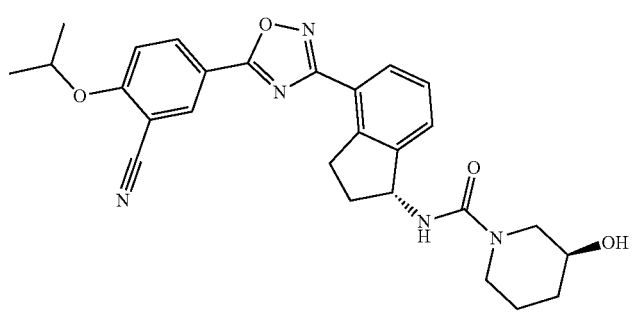 [SMILES: CC(C)Oc1ccc(-c2nc(-c3cccc4c3CC[C@H]4NC(=O)N3CCC[C@H](O)C3)no2)cc1C#N]
141
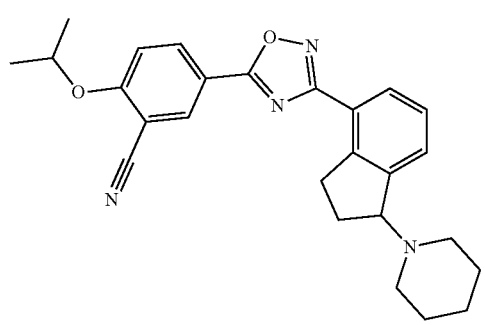 [SMILES: CC(C)Oc1ccc(-c2nc(-c3cccc4c3CCC4N3CCCCC3)no2)cc1C#N]
142

TABLE 1-continued
Representative Compounds
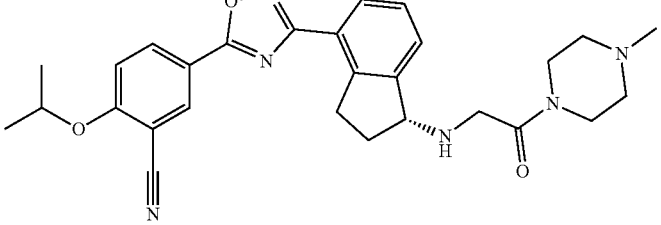
143
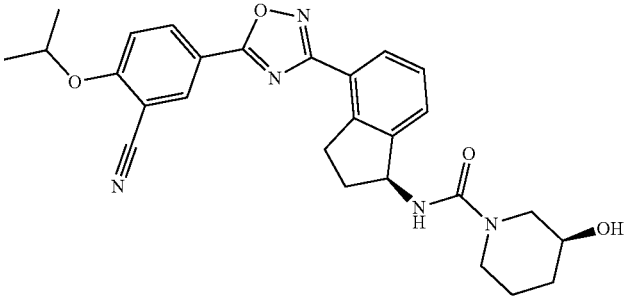 [SMILES: CC(C)Oc1ccc(-c2nc(-c3cccc4c3CC[C@@H]4NC(=O)N3CCC[C@H](O)C3)no2)cc1C#N]
144
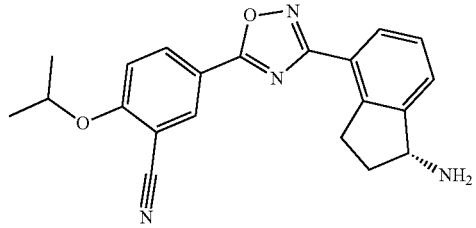 [SMILES: CC(C)Oc1ccc(-c2nc(-c3cccc4c3CC[C@H]4N)no2)cc1C#N]
145
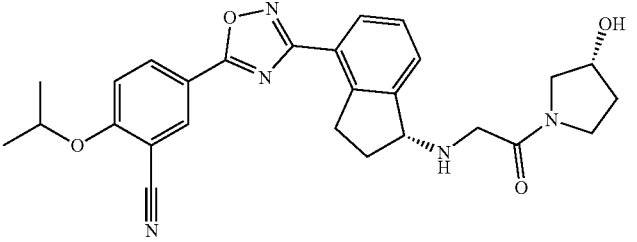 [SMILES: CC(C)Oc1ccc(-c2nc(-c3cccc4c3CC[C@H]4NCC(=O)N3CC[C@@H](O)C3)no2)cc1C#N]
146
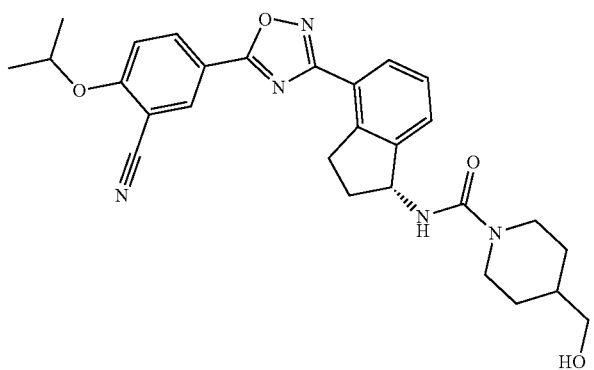 [SMILES: CC(C)Oc1ccc(-c2nc(-c3cccc4c3CC[C@H]4NC(=O)N3CCC(CO)CC3)no2)cc1C#N]
147

TABLE 1-continued
Representative Compounds
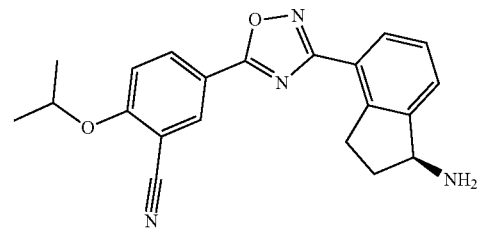 [SMILES: CC(C)Oc1ccc(-c2nc(-c3cccc4c3CC[C@@H]4N)no2)cc1C#N]
148
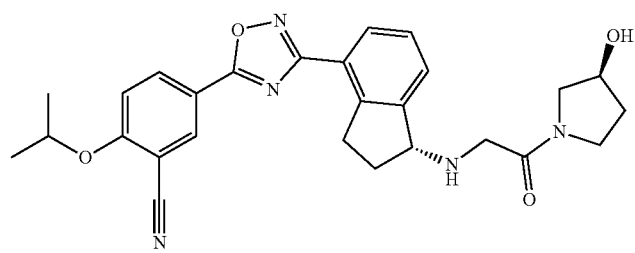 [SMILES: CC(C)Oc1ccc(-c2nc(-c3cccc4c3CC[C@H]4NCC(=O)N3CC[C@H](O)C3)no2)cc1C#N]
149
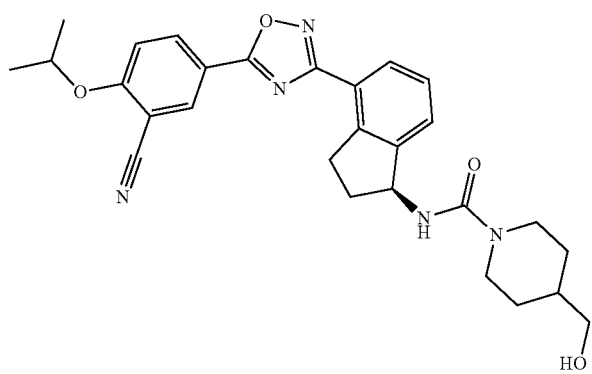 [SMILES: CC(C)Oc1ccc(-c2nc(-c3cccc4c3CC[C@@H]4NC(=O)N3CCC(CO)CC3)no2)cc1C#N]
150
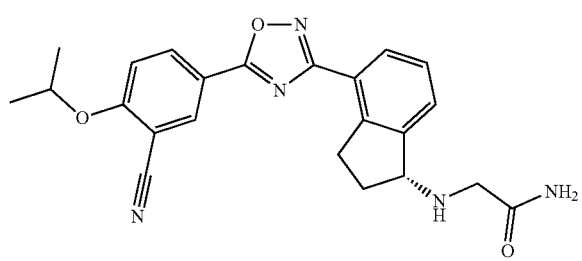 [SMILES: CC(C)Oc1ccc(-c2nc(-c3cccc4c3CC[C@H]4NCC(N)=O)no2)cc1C#N]
151
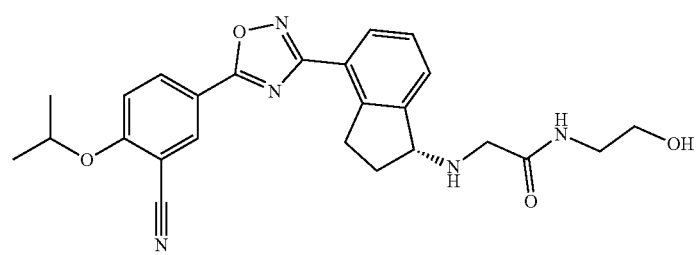 [SMILES: CC(C)Oc1ccc(-c2nc(-c3cccc4c3CC[C@H]4NCC(=O)NCCO)no2)cc1C#N]
152

US 11,278,526 B2
81                                    82
TABLE 1-continued
Representative Compounds
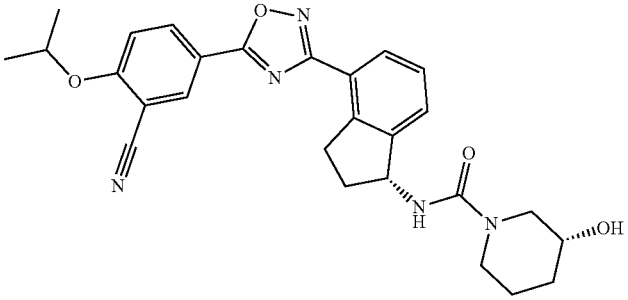 [SMILES: CC(C)Oc1ccc(-c2nc(-c3cccc4c3CC[C@H]4NC(=O)N3CCC[C@@H](O)C3)no2)cc1C#N]
153
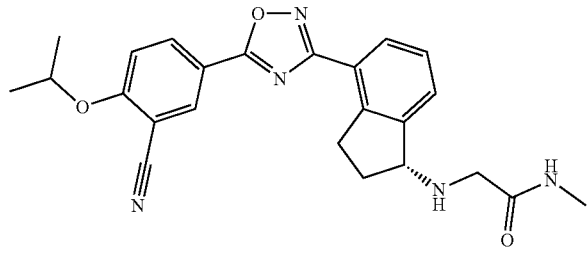
154
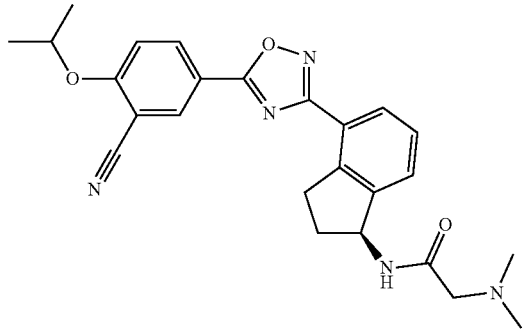 [SMILES: CC(C)Oc1ccc(-c2nc(-c3cccc4c3CC[C@@H]4NC(=O)CN(C)C)no2)cc1C#N]
155
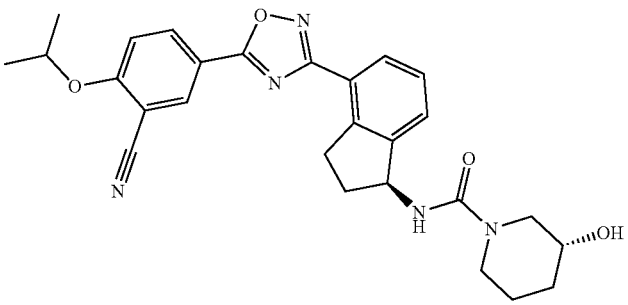 [SMILES: CC(C)Oc1ccc(-c2nc(-c3cccc4c3CC[C@@H]4NC(=O)N3CCC[C@@H](O)C3)no2)cc1C#N]
156
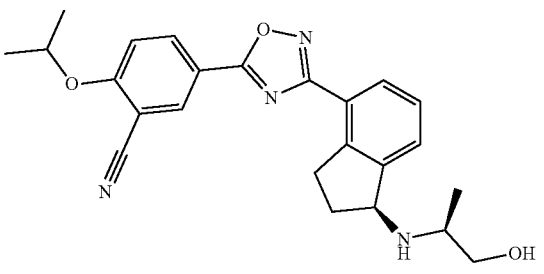 [SMILES: CC(C)Oc1ccc(-c2nc(-c3cccc4c3CC[C@@H]4N[C@@H](C)CO)no2)cc1C#N]
157

TABLE 1-continued

Representative Compounds

| | |
|---|---|
| (structure) | 158 |
| (structure) | 159 |
| (structure) | 160 |
| (structure) | 161 |
| (structure) | 162 |

TABLE 1-continued
Representative Compounds
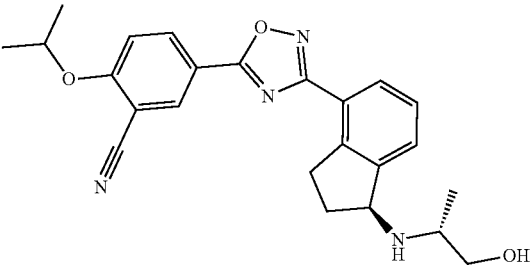 [SMILES: CC(C)Oc1ccc(-c2nc(-c3cccc4c3CC[C@@H]4N[C@H](C)CO)no2)cc1C#N]
163
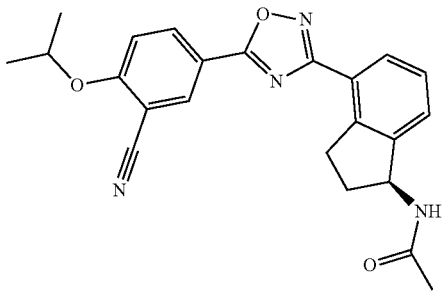 [SMILES: CC(=O)N[C@H]1CCc2c(-c3noc(-c4ccc(OC(C)C)c(C#N)c4)n3)cccc21]
164
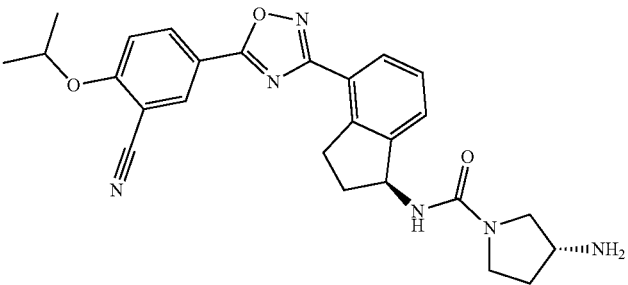 [SMILES: CC(C)Oc1ccc(-c2nc(-c3cccc4c3CC[C@@H]4NC(=O)N3CC[C@@H](N)C3)no2)cc1C#N]
165
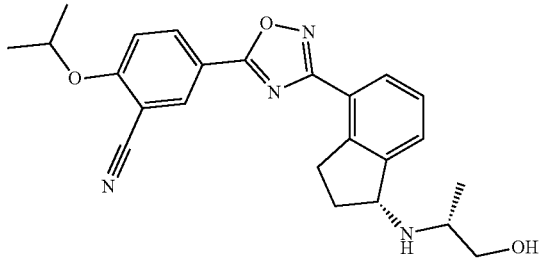 [SMILES: CC(C)Oc1ccc(-c2nc(-c3cccc4c3CC[C@H]4N[C@H](C)CO)no2)cc1C#N]
166
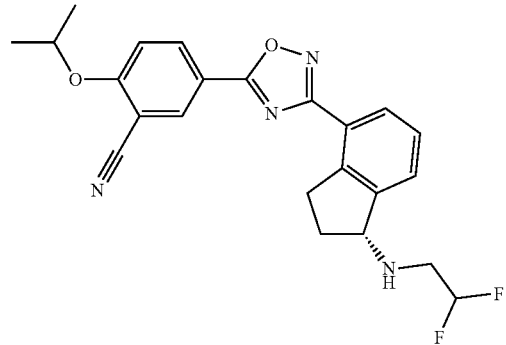 [SMILES: CC(C)Oc1ccc(-c2nc(-c3cccc4c3CC[C@H]4NCC(F)F)no2)cc1C#N]
167

TABLE 1-continued

Representative Compounds

| | |
|---|---|
| 168 | |
| 169 | |
| 170 | |
| 171 | |
| 172 | |

TABLE 1-continued
Representative Compounds
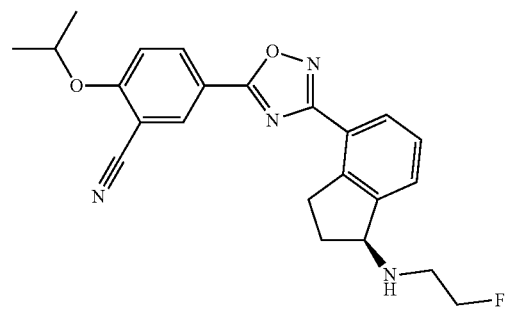 [SMILES: CC(C)Oc1ccc(-c2nc(-c3cccc4c3CC[C@@H]4NCCF)no2)cc1C#N]
173
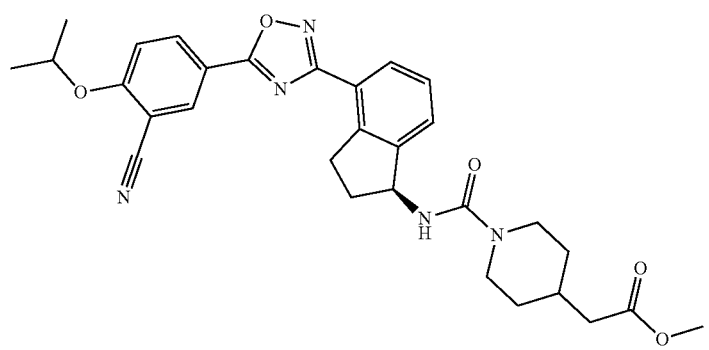 [SMILES: COC(=O)CC1CCN(C(=O)N[C@H]2CCc3c(-c4noc(-c5ccc(OC(C)C)c(C#N)c5)n4)cccc32)CC1]
174
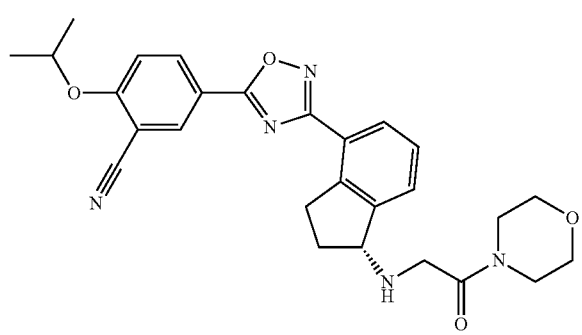 [SMILES: CC(C)Oc1ccc(-c2nc(-c3cccc4c3CC[C@H]4NCC(=O)N3CCOCC3)no2)cc1C#N]
175
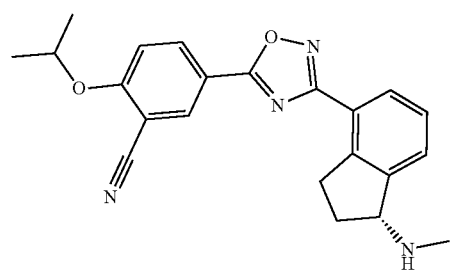 [SMILES: CN[C@@H]1CCc2c(-c3noc(-c4ccc(OC(C)C)c(C#N)c4)n3)cccc21]
176
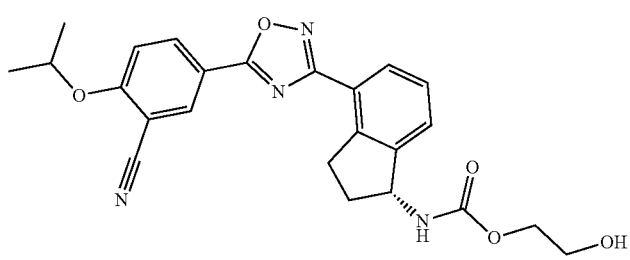 [SMILES: CC(C)Oc1ccc(-c2nc(-c3cccc4c3CC[C@H]4NC(=O)OCCO)no2)cc1C#N]
177

TABLE 1-continued
Representative Compounds
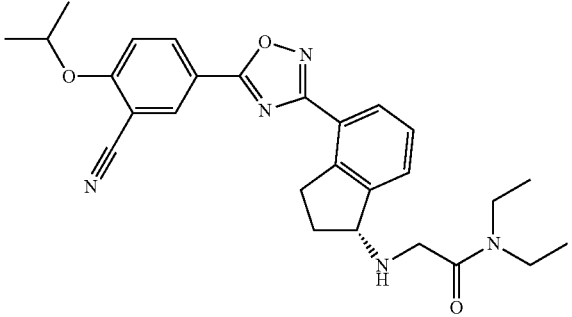 [SMILES: CCN(CC)C(=O)CN[C@@H]1CCc2c(-c3noc(-c4ccc(OC(C)C)c(C#N)c4)n3)cccc21]
178
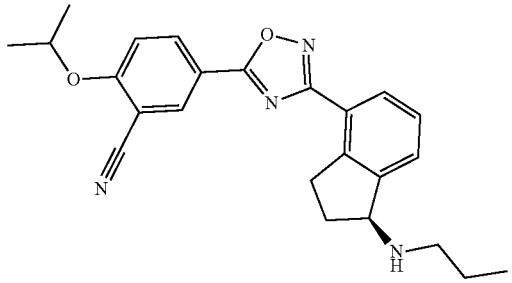 [SMILES: CCCN[C@H]1CCc2c(-c3noc(-c4ccc(OC(C)C)c(C#N)c4)n3)cccc21]
179
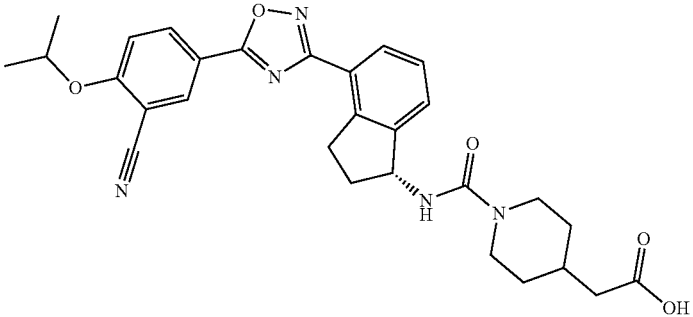 [SMILES: CC(C)Oc1ccc(-c2nc(-c3cccc4c3CC[C@H]4NC(=O)N3CCC(CC(=O)O)CC3)no2)cc1C#N]
180
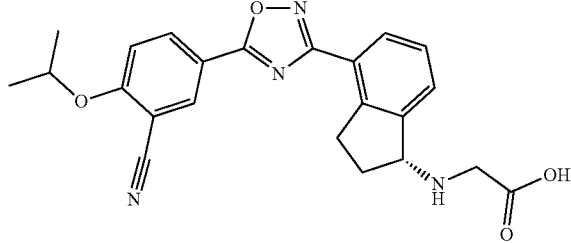 [SMILES: CC(C)Oc1ccc(-c2nc(-c3cccc4c3CC[C@H]4NCC(=O)O)no2)cc1C#N]
181
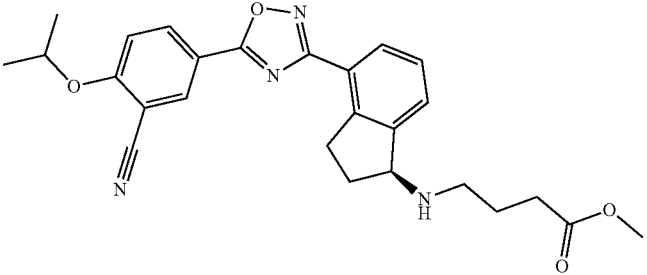 [SMILES: COC(=O)CCCN[C@H]1CCc2c(-c3noc(-c4ccc(OC(C)C)c(C#N)c4)n3)cccc21]
182

TABLE 1-continued

Representative Compounds

| | |
|---|---|
| [Structure of compound 183] | 183 |
| [Structure of compound 184] | 184 |
| [Structure of compound 185] | 185 |
| [Structure of compound 186] | 186 |
| [Structure of compound 187] | 187 |

TABLE 1-continued

Representative Compounds

188

189

190

191

192

193

TABLE 1-continued
Representative Compounds
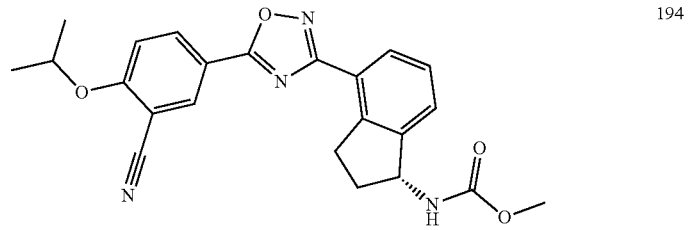
194
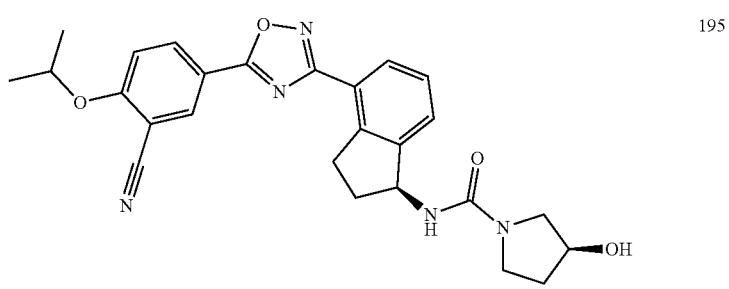
195
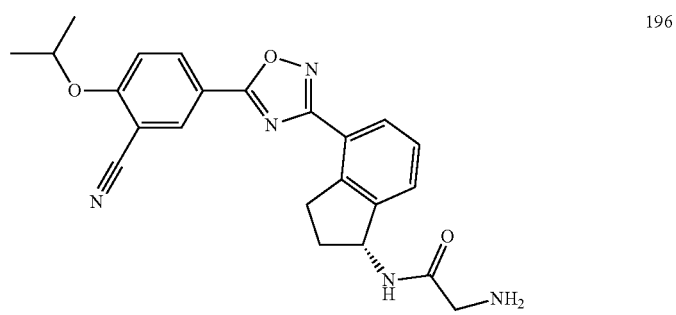
196
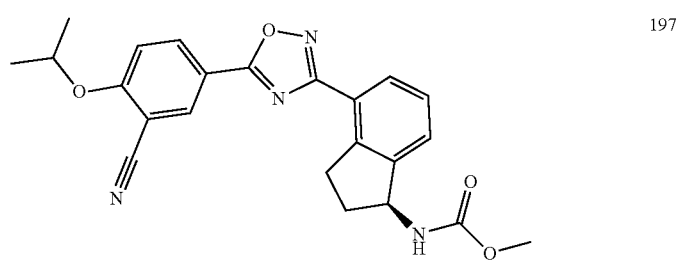
197
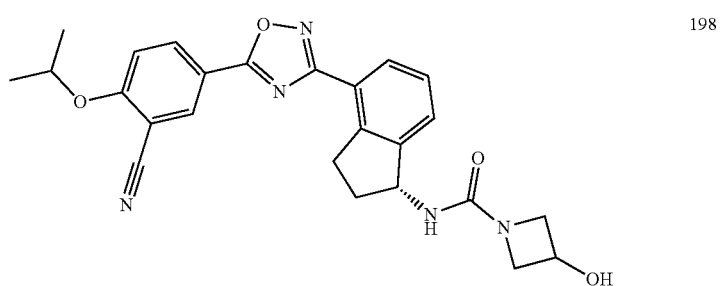
198

TABLE 1-continued
Representative Compounds
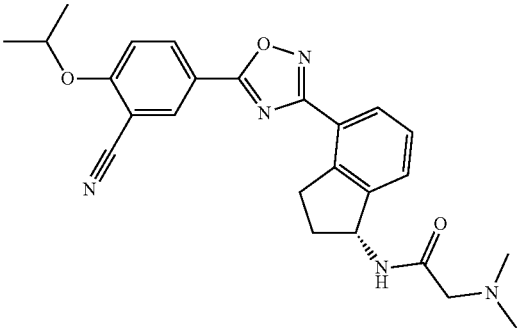 [SMILES: CC(C)Oc1ccc(-c2nc(-c3cccc4c3CC[C@H]4NC(=O)CN(C)C)no2)cc1C#N]
199
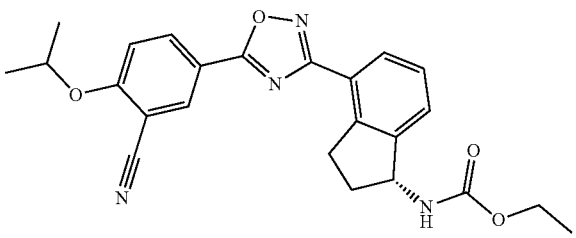 [SMILES: CCOC(=O)N[C@@H]1CCc2c(-c3noc(-c4ccc(OC(C)C)c(C#N)c4)n3)cccc21]
200
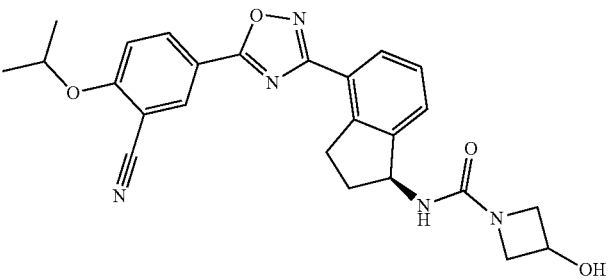 [SMILES: CC(C)Oc1ccc(-c2nc(-c3cccc4c3CC[C@@H]4NC(=O)N3CC(O)C3)no2)cc1C#N]
201
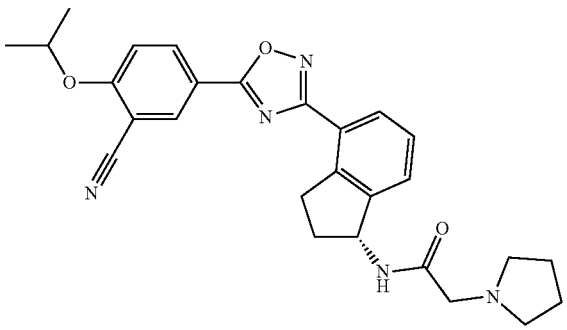 [SMILES: CC(C)Oc1ccc(-c2nc(-c3cccc4c3CC[C@H]4NC(=O)CN3CCCC3)no2)cc1C#N]
202
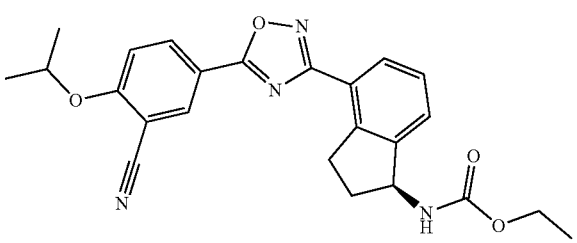 [SMILES: CCOC(=O)N[C@H]1CCc2c(-c3noc(-c4ccc(OC(C)C)c(C#N)c4)n3)cccc21]
203

TABLE 1-continued
Representative Compounds
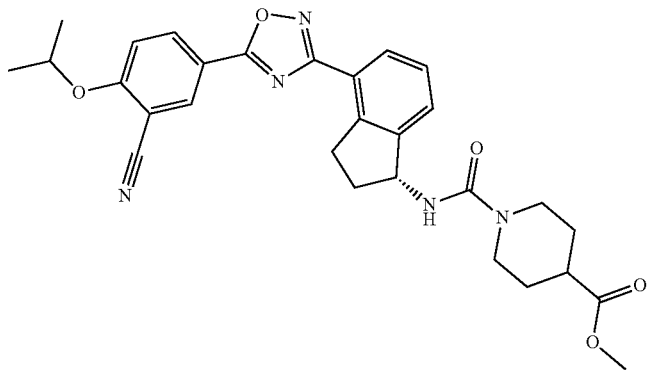 [SMILES: COC(=O)C1CCN(C(=O)N[C@@H]2CCc3c(-c4noc(-c5ccc(OC(C)C)c(C#N)c5)n4)cccc32)CC1]
204
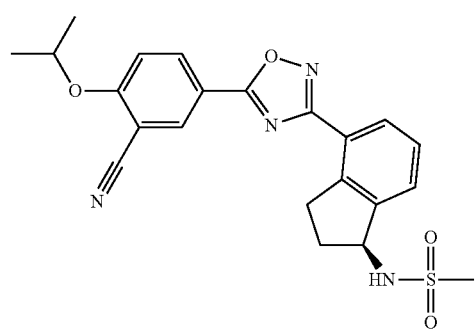 [SMILES: CC(C)Oc1ccc(-c2nc(-c3cccc4c3CC[C@@H]4NS(C)(=O)=O)no2)cc1C#N]
205
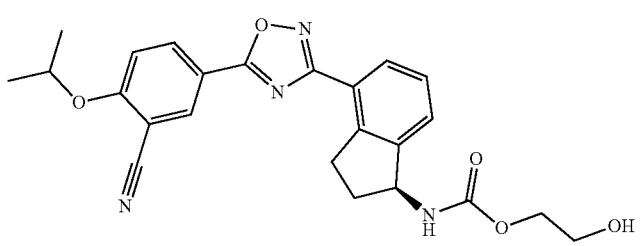 [SMILES: CC(C)Oc1ccc(-c2nc(-c3cccc4c3CC[C@@H]4NC(=O)OCCO)no2)cc1C#N]
206
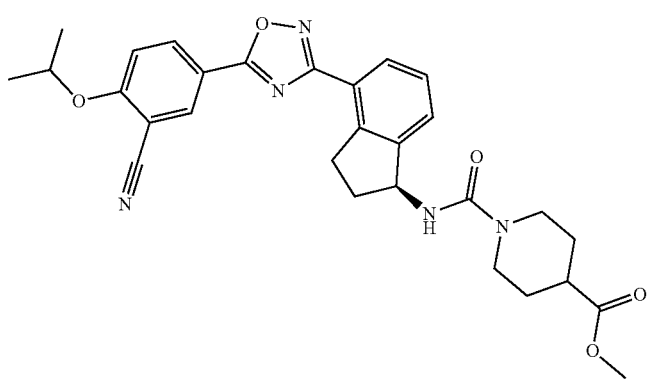 [SMILES: COC(=O)C1CCN(C(=O)N[C@H]2CCc3c(-c4noc(-c5ccc(OC(C)C)c(C#N)c5)n4)cccc32)CC1]
207

TABLE 1-continued

Representative Compounds

208

209

210

211

212

TABLE 1-continued
Representative Compounds
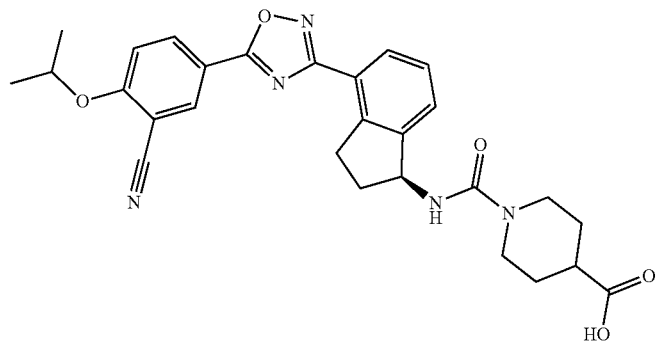 [SMILES: CC(C)Oc1ccc(-c2nc(-c3cccc4c3CC[C@@H]4NC(=O)N3CCC(C(=O)O)CC3)no2)cc1C#N]
213
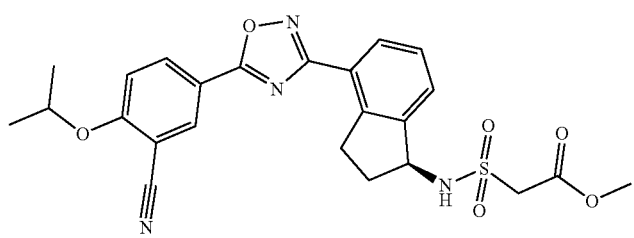 [SMILES: COC(=O)CS(=O)(=O)N[C@H]1CCc2c(-c3noc(-c4ccc(OC(C)C)c(C#N)c4)n3)cccc21]
214
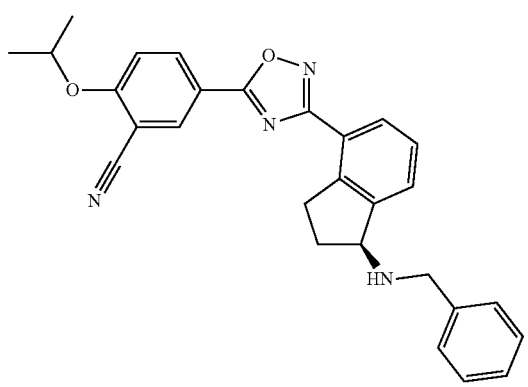 [SMILES: CC(C)Oc1ccc(-c2nc(-c3cccc4c3CC[C@@H]4NCc3ccccc3)no2)cc1C#N]
215
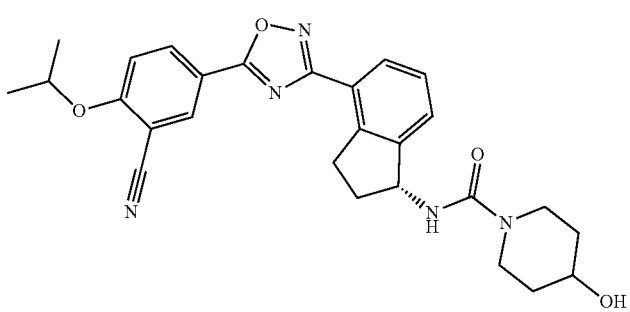 [SMILES: CC(C)Oc1ccc(-c2nc(-c3cccc4c3CC[C@H]4NC(=O)N3CCC(O)CC3)no2)cc1C#N]
216
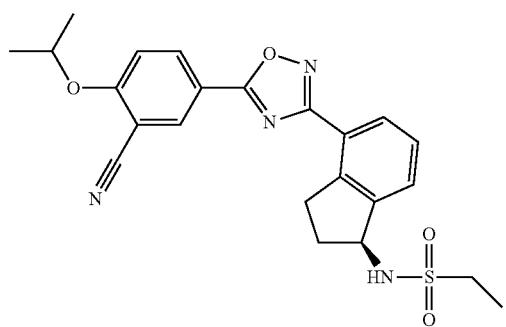 [SMILES: CCS(=O)(=O)N[C@H]1CCc2c(-c3noc(-c4ccc(OC(C)C)c(C#N)c4)n3)cccc21]
217

TABLE 1-continued
Representative Compounds
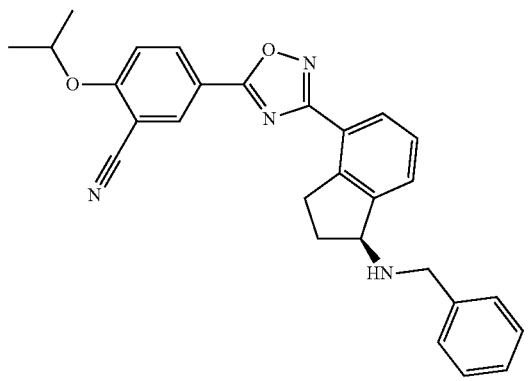 [SMILES: CC(C)Oc1ccc(-c2nc(-c3cccc4c3CC[C@@H]4NCc3ccccc3)no2)cc1C#N]
218
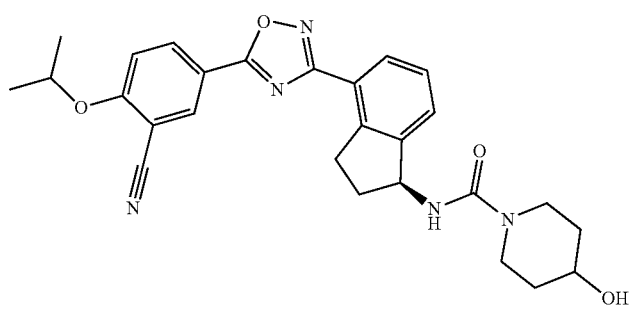 [SMILES: CC(C)Oc1ccc(-c2nc(-c3cccc4c3CC[C@@H]4NC(=O)N3CCC(O)CC3)no2)cc1C#N]
219
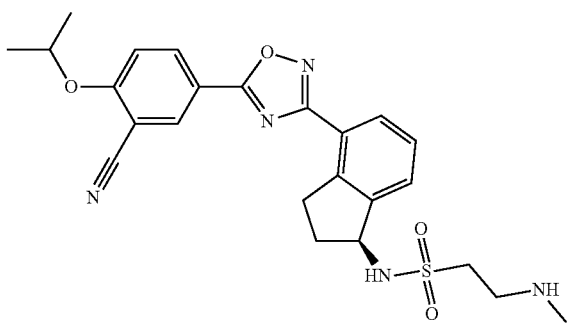 [SMILES: CNCCS(=O)(=O)N[C@H]1CCc2c(-c3noc(-c4ccc(OC(C)C)c(C#N)c4)n3)cccc21]
220
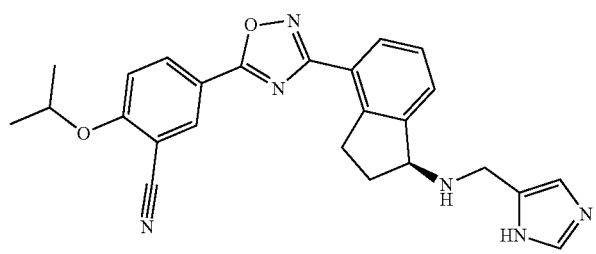 [SMILES: CC(C)Oc1ccc(-c2nc(-c3cccc4c3CC[C@@H]4NCc3cnc[nH]3)no2)cc1C#N]
221
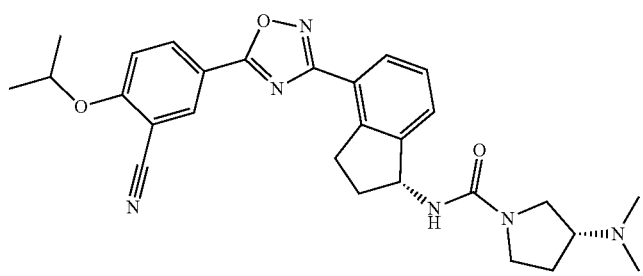 [SMILES: CC(C)Oc1ccc(-c2nc(-c3cccc4c3CC[C@H]4NC(=O)N3CC[C@@H](N(C)C)C3)no2)cc1C#N]
222

TABLE 1-continued
Representative Compounds
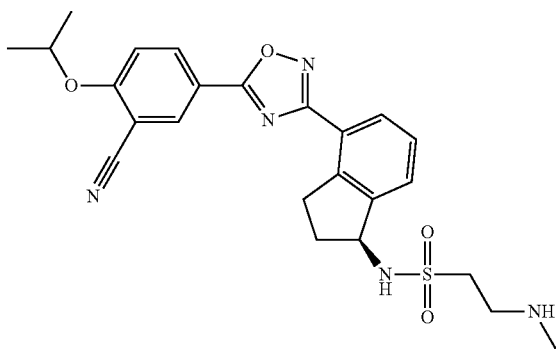 [SMILES: CNCCS(=O)(=O)N[C@H]1CCc2c(-c3noc(-c4ccc(OC(C)C)c(C#N)c4)n3)cccc21]
223
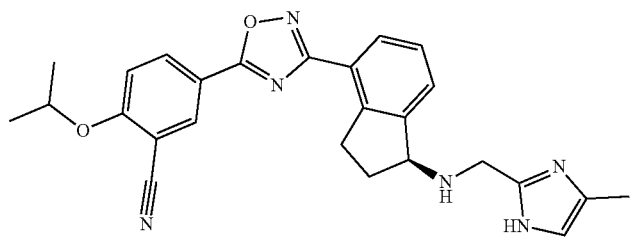 [SMILES: Cc1c[nH]c(CN[C@H]2CCc3c(-c4noc(-c5ccc(OC(C)C)c(C#N)c5)n4)cccc32)n1]
224
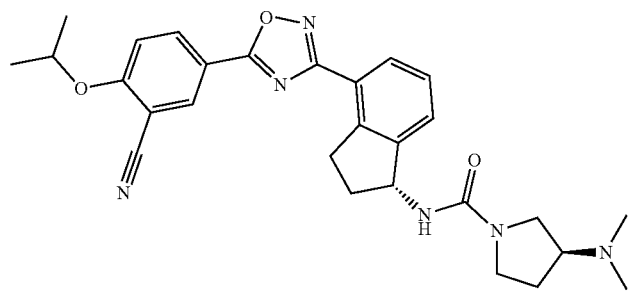 [SMILES: CC(C)Oc1ccc(-c2nc(-c3cccc4c3CC[C@H]4NC(=O)N3CC[C@H](N(C)C)C3)no2)cc1C#N]
225
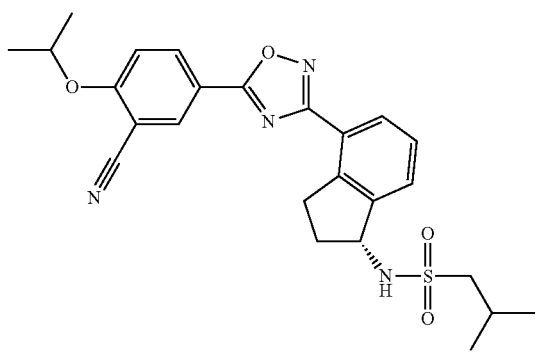 [SMILES: CC(C)CS(=O)(=O)N[C@@H]1CCc2c(-c3noc(-c4ccc(OC(C)C)c(C#N)c4)n3)cccc21]
226
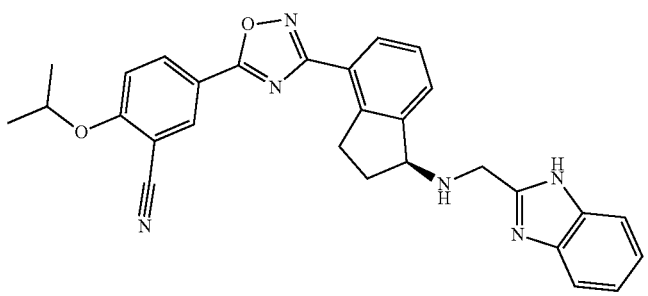 [SMILES: CC(C)Oc1ccc(-c2nc(-c3cccc4c3CC[C@@H]4NCc3nc4ccccc4[nH]3)no2)cc1C#N]
227

TABLE 1-continued
Representative Compounds
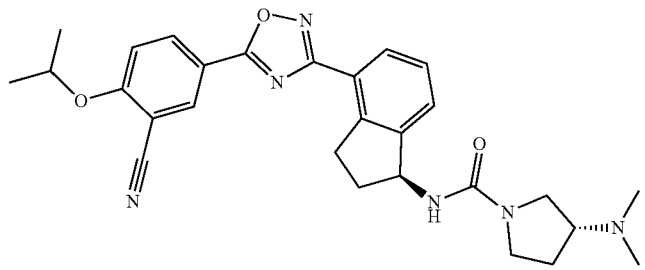 [SMILES: CC(C)Oc1ccc(-c2nc(-c3cccc4c3CC[C@@H]4NC(=O)N3CC[C@@H](N(C)C)C3)no2)cc1C#N]
228
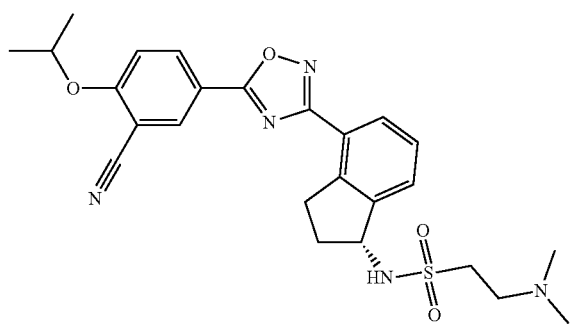 [SMILES: CC(C)Oc1ccc(-c2nc(-c3cccc4c3CC[C@H]4NS(=O)(=O)CCN(C)C)no2)cc1C#N]
229
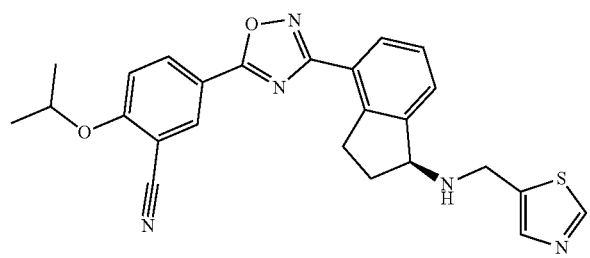 [SMILES: CC(C)Oc1ccc(-c2nc(-c3cccc4c3CC[C@@H]4NCc3cncs3)no2)cc1C#N]
230
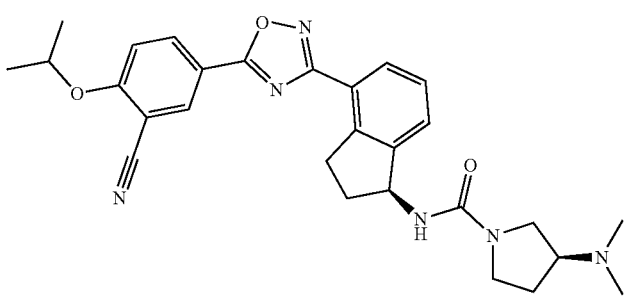 [SMILES: CC(C)Oc1ccc(-c2nc(-c3cccc4c3CC[C@@H]4NC(=O)N3CC[C@H](N(C)C)C3)no2)cc1C#N]
231
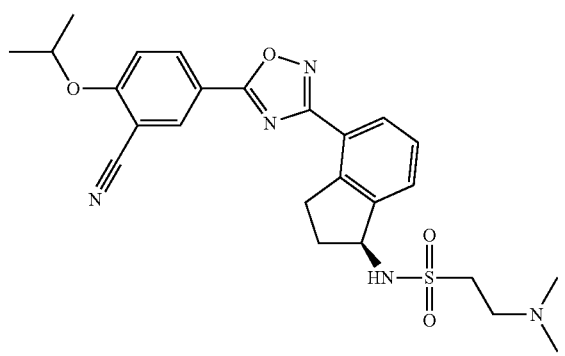 [SMILES: CC(C)Oc1ccc(-c2nc(-c3cccc4c3CC[C@@H]4NS(=O)(=O)CCN(C)C)no2)cc1C#N]
232

TABLE 1-continued
Representative Compounds
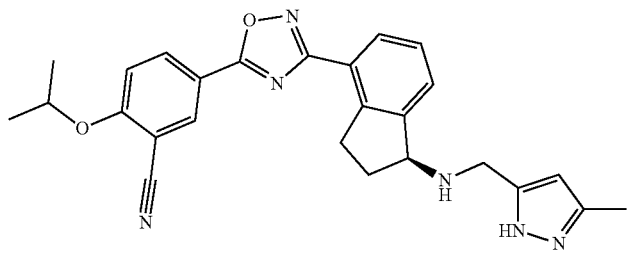 [SMILES: Cc1cc(CN[C@H]2CCc3c(-c4noc(-c5ccc(OC(C)C)c(C#N)c5)n4)cccc32)[nH]n1]
233
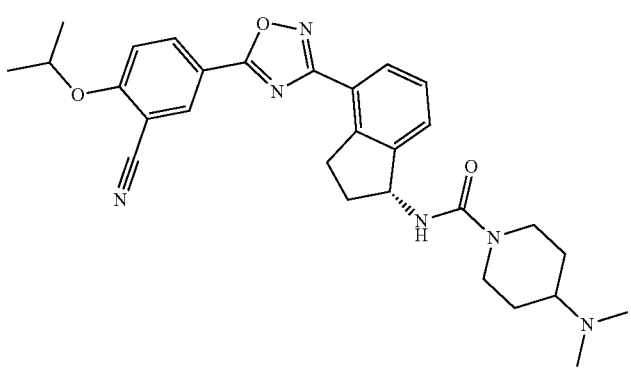 [SMILES: CC(C)Oc1ccc(-c2nc(-c3cccc4c3CC[C@H]4NC(=O)N3CCC(N(C)C)CC3)no2)cc1C#N]
234
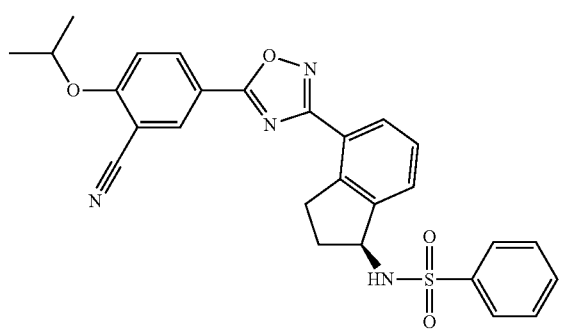 [SMILES: CC(C)Oc1ccc(-c2nc(-c3cccc4c3CC[C@@H]4NS(=O)(=O)c3ccccc3)no2)cc1C#N]
235
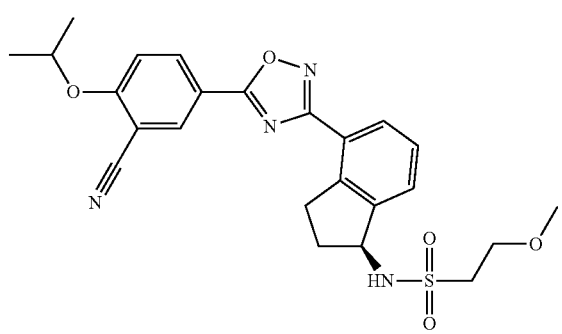 [SMILES: COCCS(=O)(=O)N[C@H]1CCc2c(-c3noc(-c4ccc(OC(C)C)c(C#N)c4)n3)cccc21]
236

TABLE 1-continued
Representative Compounds
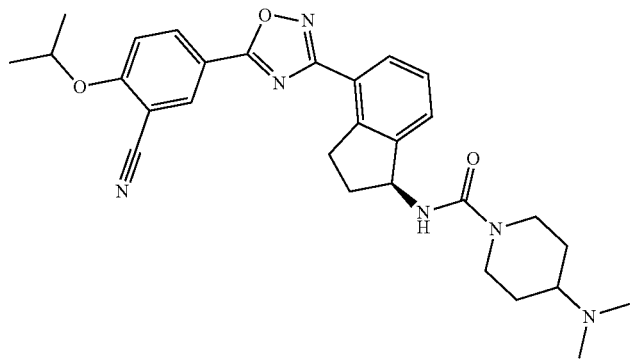 [SMILES: CC(C)Oc1ccc(-c2nc(-c3cccc4c3CC[C@@H]4NC(=O)N3CCC(N(C)C)CC3)no2)cc1C#N]
237
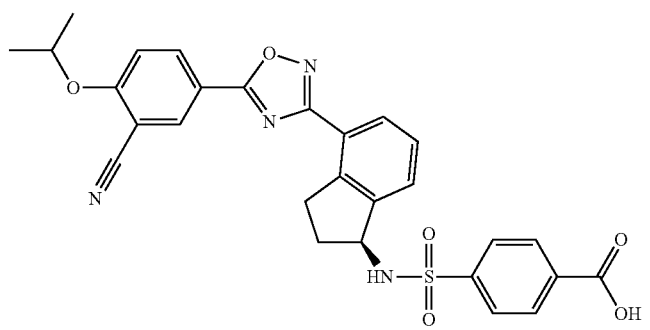 [SMILES: CC(C)Oc1ccc(-c2nc(-c3cccc4c3CC[C@@H]4NS(=O)(=O)c3ccc(C(=O)O)cc3)no2)cc1C#N]
238
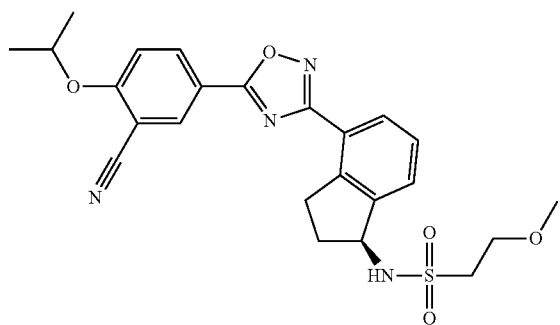 [SMILES: COCCS(=O)(=O)N[C@H]1CCc2c(-c3noc(-c4ccc(OC(C)C)c(C#N)c4)n3)cccc21]
239
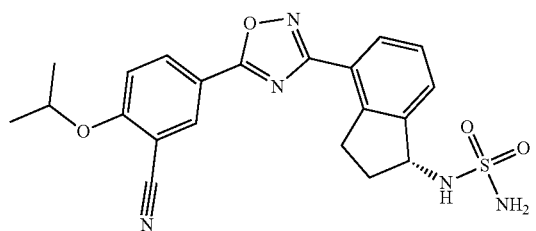 [SMILES: CC(C)Oc1ccc(-c2nc(-c3cccc4c3CC[C@H]4NS(N)(=O)=O)no2)cc1C#N]
240
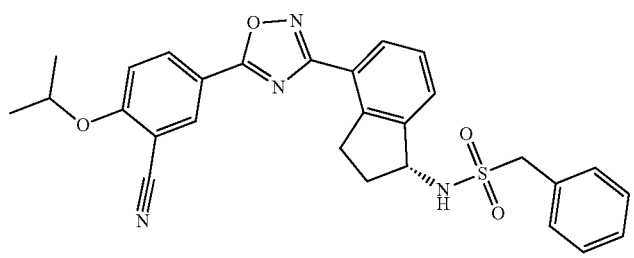 [SMILES: CC(C)Oc1ccc(-c2nc(-c3cccc4c3CC[C@H]4NS(=O)(=O)Cc3ccccc3)no2)cc1C#N]
241

117                                                                                  118
TABLE 1-continued
Representative Compounds
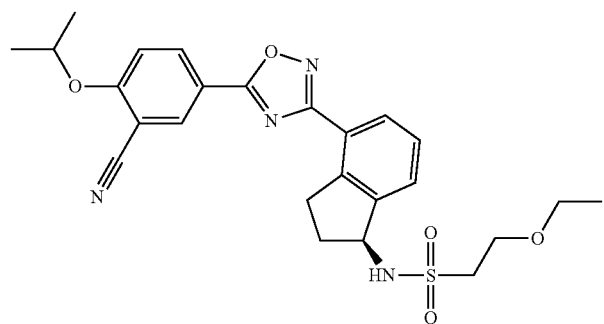 [SMILES: CCOCCS(=O)(=O)N[C@H]1CCc2c(-c3noc(-c4ccc(OC(C)C)c(C#N)c4)n3)cccc21]
242
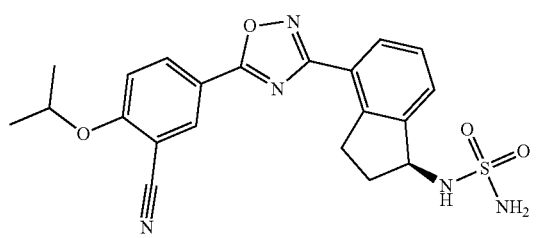 [SMILES: CC(C)Oc1ccc(-c2nc(-c3cccc4c3CC[C@@H]4NS(N)(=O)=O)no2)cc1C#N]
243
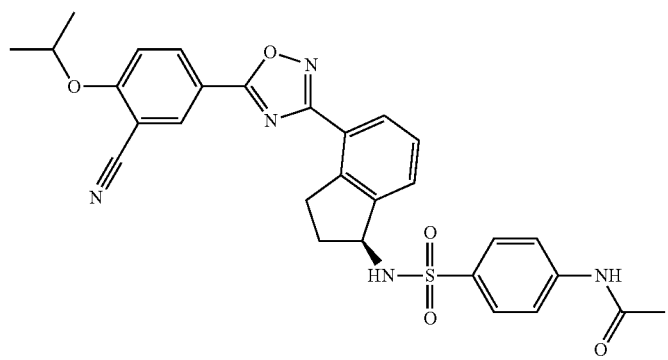 [SMILES: CC(=O)Nc1ccc(S(=O)(=O)N[C@H]2CCc3c(-c4noc(-c5ccc(OC(C)C)c(C#N)c5)n4)cccc32)cc1]
244
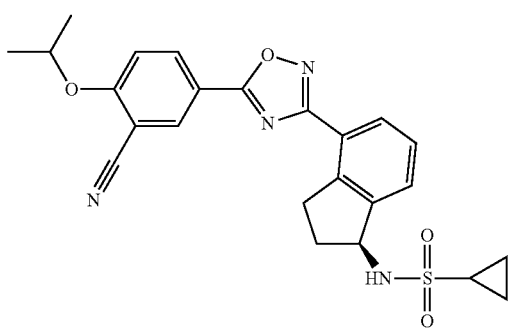 [SMILES: CC(C)Oc1ccc(-c2nc(-c3cccc4c3CC[C@@H]4NS(=O)(=O)C3CC3)no2)cc1C#N]
245
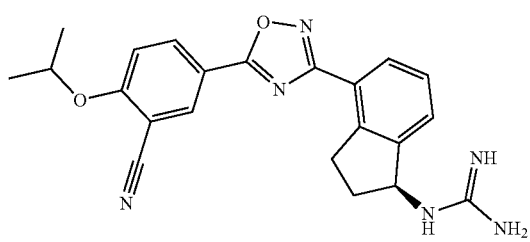 [SMILES: CC(C)Oc1ccc(-c2nc(-c3cccc4c3CC[C@@H]4NC(=N)N)no2)cc1C#N]
246

TABLE 1-continued
Representative Compounds
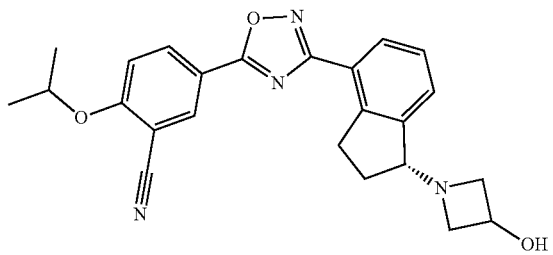 [SMILES: CC(C)Oc1ccc(-c2nc(-c3cccc4c3CC[C@H]4N3CC(O)C3)no2)cc1C#N]
247
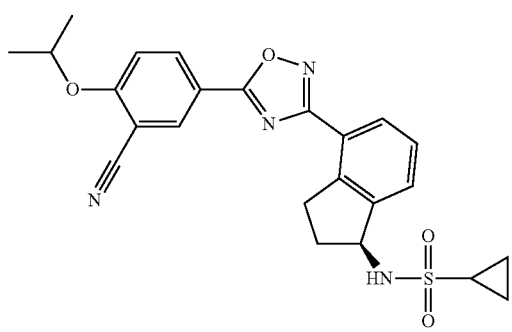 [SMILES: CC(C)Oc1ccc(-c2nc(-c3cccc4c3CC[C@@H]4NS(=O)(=O)C3CC3)no2)cc1C#N]
248
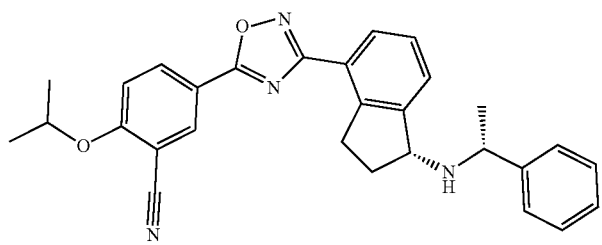 [SMILES: CC(C)Oc1ccc(-c2nc(-c3cccc4c3CC[C@H]4N[C@H](C)c3ccccc3)no2)cc1C#N]
249
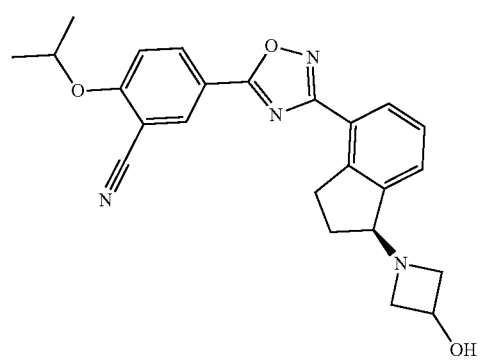 [SMILES: CC(C)Oc1ccc(-c2nc(-c3cccc4c3CC[C@@H]4N3CC(O)C3)no2)cc1C#N]
250
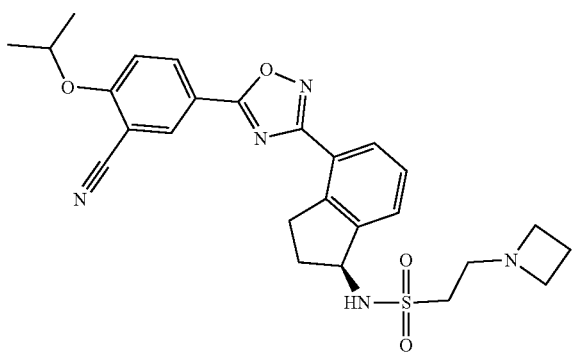 [SMILES: CC(C)Oc1ccc(-c2nc(-c3cccc4c3CC[C@@H]4NS(=O)(=O)CCN3CCC3)no2)cc1C#N]
251

TABLE 1-continued

Representative Compounds

252

[Chemical structure: 5-(4-isopropoxy-3-(methylsulfonyl)phenyl)-3-(1-amino-2,3-dihydro-1H-inden-4-yl)-1,2,4-oxadiazole]

In another aspect, the present disclosure provides methods for modulating an expression level of a gene associated with an immune response, or fibrosis, or that is otherwise associated with systemic lupus erythematosus, in a subject having or suspected of having systemic lupus erythematosus, the methods comprising administering to the subject in need thereof an effective amount of a compound as disclosed herein. In various embodiments, modulating the expression level of the gene results in an increased expression level of the gene. In various embodiments, modulating the expression level of the gene results in a decreased expression level of the gene. In various embodiments, the compound is selected from Table 1. In various embodiments, the compound is compound 148. Genes that are associated with an immune response, or fibrosis, or that are otherwise associated with SLE are known by those having ordinary skill in the art. In various embodiments of this aspect, the gene is IL-10, IL-1β, CCL5, TNFSF13b/BAFF, CXCL9, CXCL10, TGFβ2, LCN2/Lipocalin 2, TAGLN/Transgelin, Timp1, LOXL1, or CD88a/Girdin.

Assays for determining gene expression are well known in the art, and include, for example, reverse-transcription polymerase chain reaction (RT-PCR), DNA microarray, and Northern blot. For example, RT-PCR using primers specific to the gene or genes of interest may be performed using the Qiagen OneStep RT-PCR Kit®. Genes associated with immune response, inflammation, fibrosis, and other indicia of SLE are known or will be readily identified by those of skill in the art. Primers for performing RT-PCR to determine the expression level of a gene of interest may be generated using routine primer design techniques based on gene sequences available on, for example, Ensembl, OMIM, UniProt, and other publically available genome databases.

In yet another aspect, the present disclosure provides a kit for use in treating SLE. In various embodiments, the kit comprises a compound according to the present disclosure and instructions for administering the compound to a subject in need thereof in order to treat SLE. In various embodiments, the compound is selected from Table 1. In various embodiments, the compound is compound 148.

As mentioned above, SLE often escapes diagnosis because the classical symptoms of the disease, which may vary in intensity over time and from subject to subject, are also associated with other conditions, such as rheumatoid arthritis. Thus, in a further aspect, the present disclosure provides a diagnostic kit for autoimmune diseases including SLE, comprising a panel of biomarkers associated with SLE. The biomarkers may be, for example, the products of gene (mRNA) and/or protein expression. Assays for determining gene expression are well known in the art, and include, for example, reverse-transcription polymerase chain reaction (RT-PCR), DNA microarray, and Chemical Ligation Dependent Probe Amplification (CLPA) combined with either Capillary Electrophoresis (CE) or Next Generation Sequencing for clinical delivery. Thus, in various embodiments, a diagnostic kit comprises RT-PCR primers suitable for reverse transcription of an RNA molecule of interest, primers suitable for amplifying a cDNA resulting from the reverse transcription, capillary electrophoresis reagents and conditions, and, optionally, other RT-PCR reagents. In various embodiments, a diagnostic kit further comprises RNA extraction reagents and materials for extracting RNA from a subject sample, such as serum obtained from the subject.

In various embodiments, the diagnostic kit comprises one or more sets of RT-PCR primers for specifically amplifying an mRNA product of an interferon-inducible (IFI) gene. In various embodiments, the IFI genes are selected from the group consisting of: IFI27, IFI44, IFI33L, RSAD2, EPSTI1, SPATS2L, and EIF2AK2. The kit may further comprise RT-PCR primers specific for one or more constitutively expressed (control) gene. In various embodiments, the one or more control gene is selected from the group consisting of 18S, ACTB, and GAPDH. In various embodiments, the kit further comprises a non-transitory computer-readable medium storing a program capable of causing a computer to (a) compare the expression levels of the one or more IFI gene and the one or more control gene in a sample and (b) determine, based on the comparison, whether a sample obtained from the subject shows a clinically relevant increase of IFI gene expression relative to control (in which case the subject is diagnosed as having or being at high risk for having SLE).

Assays for determining protein expression are well known in the art, and include, for example, Western blotting, 2-D gel electrophoresis, and immunoassays. Thus, in various embodiments, a diagnostic kit comprises one or more antibody having specific affinity for an interferon-inducible protein, such as the protein product produced by expression of an IFI gene as described above. In various embodiments, a diagnostic kit further comprises one or more antibody having specific affinityfor a control protein, such as the protein product produced by expression of a control gene as described above. In various embodiments, the kit further comprises a non-transitory computer-readable medium storing a program capable of causing a computer to (a) compare the expression levels of the one or more IFI protein and the one or more control protein in a sample and (b) determine, based on the comparison, whether a sample obtained from the subject shows a clinically relevant increase of IFI protein expression relative to control (in which case the subject is diagnosed as having or being at high risk for having SLE).

EXAMPLES

Compounds for use in the methods and kits of the present disclosure may be synthesized and evaluated in bioassays as described herein, as well as in U.S. Pat. Nos. 8,481,573, 8,362,048, and 8,796,318, the entireties of which are incorporated by reference. An exemplary compound for use in the methods of the present disclosure (compound 148 of Table 1) may be synthesized using the techniques described in Example 1 below. Methods for treating SLE using the compounds are exemplified in Examples 2-13.

Example 1

Synthesis of Compound 148
General Methods of Synthesis $^1$H NMR (400 MHz) and $^{13}$C NMR (100 MHz) were obtained in solution of deuteriochloroform (CDCl$_3$), deuteriomethanol (CD$_3$OD) or dimethyl sulfoxide—D$_6$ (DMSO). NMR spectra were processed using Mestrec 5.3.0 and 6.0.1. $^{13}$C NMR peaks that are bracketed are two rotomers of the same carbon. Mass spectra (LCMS) were obtained using an Agilent 1100/6110 HPLC system equipped with a Thompson ODS-A, 100 Å, 5µ(50×4.6 mm) column using water with 0.1% formic acid as the mobile phase A, and acetonitrile with 0.1% formic acid as the mobile phase B. The gradient was 20-100% with mobile phase B over 2.5 min then held at 100% for 2.5 mins. The flow rate was 1 mL/min. For more hydrophobic compounds, the following gradient was used, denoted as Method 1: 40-95% over 0.5 min, hold at 95% for 8.5 min, then return to 40% over 2 min, with a flow rate of 1 mL/min. Final compounds were checked for purity using Method 2: 5% for 1 min, 5-95% over 9 min, then hold at 95% for 5 min, with a flow rate of 1 mL/min. Enantiomeric excess was determined by integration of peaks that were separated on a Chiralpak AD-H, 250×4.6 mm column, 5 m particle size. Flow rate of 1 mL/min and an isocratic mobile phase. Unless otherwise indicated, the chiral data provided uses this method. Alternatively, chiral separations were performed under the following conditions, denoted as Chiral Method 1: Chiralpak AY-H, 250×4.6 mm column, 5 m particle size. Flow rate of 1 mL/min and an isocratic mobile phase. Chiral Method 2: Chiralcel OZ-3, 250×4.6, 3 µm particle size at a flow rate of 0.75 ml/min. The pyridine, dichloromethane (DCM), tetrahydrofuran (THF), and toluene used in the procedures were from Aldrich Sure-Seal bottles kept under nitrogen (N$_2$). All reactions were stirred magnetically and temperatures are external reaction temperatures. Chromatographies were carried out using a Combiflash Rf flash purification system (Teledyne Isco) equipped with Redisep (Teledyne Isco) silica gel (SiO$_2$) columns. Preparative HPLC purifications were done on Varian ProStar/PrepStar system using water containing 0.05% trifluoroacetic acid as mobile phase A, and acetonitrile with 0.05% trifluoroacetic acid as mobile phase B. The gradient was 10-80% with mobile phase B over 12 min, hold at 80% for 2 min, and then return to 10% over 2 min with flow rate of 22 mL/min. Other methods similar to this may have been employed. Fractions were collected using a Varian Prostar fraction collector and were evaporated using a Savant SpeedVac Plus vacuum pump. Compounds with salt-able centers were presumed to be the trifluoroacetic acid (TFA) salt. Microwave heating was performed using a Biotage Initiator microwave reactor equipped with Biotage microwave vessels. The following abbreviations are used: ethyl acetate (EA), triethylamine (TEA), diethyl amine (DEA), hydroxybenzotriazole (HOBt), 1-ethyl-3-(3-dimethylaminopropyl) carbodiimide hydrochloride (EDC), isopropanol (IPA), dimethylformamide (DMF), dimethyl acetamide (DMA). Norit is activated charcoal.

1. 1-oxo-2,3-dihydro-1H-indene-4-carbonitrile (INT-1)

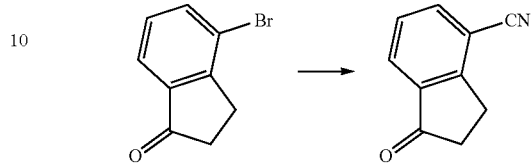

To a stirred solution of 4-bromo-2,3-dihydro-1H-inden-1-one (100.0 g, 0.48 mol) in 150 mL of 1-methy-2-pyrrolidine (NMP) was added zinc cyanide (111.8 g, 0.95 mol) and tetrakis(triphenylphosphine)palladium [Pd(PPh$_3$)$_4$] (2.75 g, 0.024 mol). The solution was degassed with N$_2$ and the reaction mixture heated at 95° C. for 7 h. Upon cooling, the reaction mixture was poured onto ice water (3.5 L). The compound and inorganic Zn salts precipitated. The solid was collected and partitioned between DCM (3×100 mL) and water. The organic layers were filtered to remove the Zn salts, and the filtrate was concentrated and crystallized from a 4:1 mixture of EtOH and MeOH (400 mL) to give 45.5 g (60%) of 1-oxo-2,3-dihydro-1H-indene-4-carbonitrile INT-1 as a light yellow solid. LCMS-ESI (m/z) calculated for C$_{10}$H$_7$NO: 157.2; found 158.1 [M+H]$^+$, t$_R$=2.67 min. $^1$H NMR (400 MHz, CDCl$_3$) δ 8.00-7.90 (m, 1H), 7.86 (dd, J=7.5, 1.1, 1H), 7.50 (t, J=7.6, 1H), 3.40-3.19 (m, 2H), 2.90-2.61 (m, 2H). $^{13}$C NMR (101 MHz, CDCl$_3$) δ 204.70, 157.90, 138.38, 137.88, 128.44, 128.28, 116.31, 111.70, 36.01, 25.49.

2. (S)-1-hydroxy-2,3-dihydro-1H-indene-4-carbonitrile (INT-2)

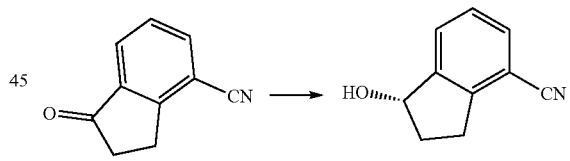

To a 3-neck flask with an internal thermometer and an addition funnel was added (R)-(+)-2-methyl-CBS-oxazaborolidine solution in toluene (3.0 mL) and borane-dimethylsulfide (300 µL). The reaction was stirred at room temperature for 10 min then diluted with DCM (25 mL). Borane-dimethylsulfide (6.0 mL) was added and, after stirring for 5 min, the reaction was cooled to −20° C. 1-Oxo-2,3-dihydro-1H-indene-4-carbonitrile INT-1 (4.7 g, 30 mmol) in DCM (25 mL) was added dropwise by addition funnel over 20 min while maintaining the reaction at −20±5° C. The reaction was stirred for 1 h then quenched by the dropwise addition of MeOH (20 mL). After hydrogen evolution ceased, MeOH (30 mL) was added and removed by heating at atmospheric pressure. MeOH (50 mL) was added in two and removed by heating twice. All the solvent was evaporated to give a solid which was recrystallized from EA (9 mL) and hexane (22 mL). The compound was filtered and washed with 5:1 hexane/EA (30 mL) to provide 3.73 g (78%) of (S)-1-hydroxy-2,3-dihydro-1H-indene-4-carbonitrile INT-2 as a white powder. LCMS-ESI (m/z) calculated for $C_{10}H_9NO$: 159.1; found 160.1 $[M+H]^+$, $t_R$=2.39 min. $^1H$ NMR (400 MHz, $CDCl_3$) δ 7.62 (d, J=7.6 Hz, 1H), 7.53 (d, J=7.6 Hz, 1H), 7.32 (t, J=7.6 Hz, 1H), 5.28 (d, J=4.1 Hz, 1H), 3.23 (ddd, J=17.0, 8.7, 4.4 Hz, 1H), 3.04-2.90 (m, 1H), 2.64-2.51 (m, 1H), 2.00 (dddd, J=13.4, 8.7, 7.1, 5.7 Hz, 1H), 1.91 (d, J=5.4 Hz, 1H). Chiral HPLC: (S)-1-hydroxy-2,3-dihydro-1H-indene-4-carbonitrile was eluted in 20% IPA in hexane: >99.9% ee, $t_R$=7.42 min. The (R)-enantiomer was obtained in an analogous fashion using (S)-(−)-2-methyl-CBS-oxazaborolidine. $t_R$ for (R)-enantiomer=6.79 min.

3. (+/−) 1-hydroxy-2,3-dihydro-1H-indene-4-carbonitrile

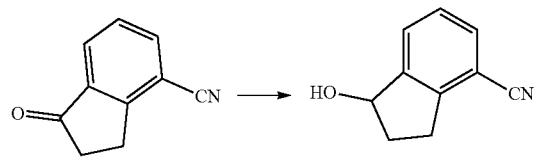 [SMILES: N#Cc1cccc2c1CCC2=O ; N#Cc1cccc2c1CCC2O]

To a stirred suspension of 1-oxo-2,3-dihydro-1H-indene-4-carbonitrile (1.2 g, 7.64 mmol) and silica gel (catalytic) in EtOH at 0° C. was added $NaBH_4$ (237.2 mg, 7.64 mmol). The reaction was allowed to warm to room temperature and stirred for 2 h. The solvent was removed under reduced pressure, and the product was purified by chromatography (50% EA/hexane) to afford 1.02 g (82.3%) of 1-hydroxy-2,3-dihydro-1H-indene-4-carbonitrile as white solid. LCMS-ESI (m/z) calculated for $C_{10}H_9NO$; 159.18; found 160.1 $[M+H]^+$, $t_R$=2.39 min.

4. (S)—N,1-dihydroxy-2,3-dihydro-1H-indene-4-carboximidamide (INT-3)

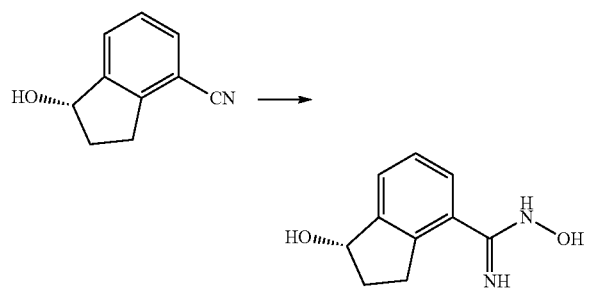

To hydroxylamine hydrochloride (0.87 g, 12.5 mmol) and sodium carbonate (1.32 g, 12.5 mmol) in EtOH (20 mL) was added (S)-1-hydroxy-2,3-dihydro-1H-indene-4-carbonitrile INT-2 (1.59 g, 10 mmol) in one portion and the solution was heated to reflux. After 16 h, the reaction was cooled and filtered to remove the solids. The EtOH was removed and the compound purified by chromatography (MeOH/DCM) to give 1.74 g (90%) of (S)—N,1-dihydroxy-2,3-dihydro-1H-indene-4-carboximidamide INT-3 as a white foam. LCMS-ESI (m/z) calculated for $C_{10}H_{12}N_2O_2$: 192.1; found: 193.1 $[M+H]^+$, $t_R$=0.56 min. $^1H$ NMR (400 MHz, MeOD) δ 10.30 (s, 1H), 9.97 (s, 1H), 7.72-7.58 (m, 1H), 7.46-7.37 (m, 2H), 5.22 (t, J=6.5, 1H), 3.17-3.03 (m, 1H), 2.99-2.83 (m, 1H), 2.49 (dddd, J=11.4, 8.0, 7.0, 4.4, 1H), 2.02-1.88 (m, 1H). (R)—N,1-dihydroxy-2,3-dihydro-1H-indene-4-carboximidamide is made in an analogous fashion from (R)-1-hydroxy-2,3-dihydro-1H-indene-4-carbonitrile.

5. Preparation of Indanols

To the benzoic acid (1 eq) in DMF (0.15 M) was added HOBt (1.5 eq) and EDC (1.5 eq). The reaction was stirred at room temperature for 2-16 h until the acid was fully activated. (R)- or (S)—N,1-dihydroxy-2,3-dihydro-1H-indene-4-carboximidamide was added in one portion and the reaction was stirred at room temperature for 2 h until complete formation of the pre-cyclized intermediate. The reaction mixture was then heated to 85° C. for 18 h. The reaction mixture was cooled to room temperature and water was added and the mixture was allowed to stand. The resulting precipitate was filtered. The material was purified by chromatography (EA/hexane) or recrystallized to give the 5-(3-(1-hydroxy-2,3-dihydro-1H-inden-4-yl)-1,2,4-oxadiazol-5-yl)-benzenes as white solids.

6. Preparation of Indane Amines from Indanols

To a flask containing racemic 5-(3-(1-hydroxy-2,3-dihydro-1H-inden-4-yl)-1,2,4-oxadiazol-5-yl)-2-isopropoxy-benzonitrile (1 eq) in DCM (0.14M) at 0° C. was added $SOCl_2$ (2 eq). After stirring for 30 min, the reaction mixture was concentrated in vacuo and placed under high vacuum for 2 h. The resulting crude chloride was dissolved in DMA (0.02M). The amine (3 eq), DIEA (3 eq), and in some cases NaBr (3 eq) were added and the resulting reactions were stirred at 55-60° C. overnight and purified either by preparative HPLC or column chromatography. If the amine contained a ether, the material could be further hydrolysed with NaOH to the acid. Diamines protected with Boc groups can be deprotected using TFA.

7. (R)—N-(4-cyano-2,3-dihydro-1H-indene-1-ylidene)-2-methylpropane-2-sulfinamide (INT-4)

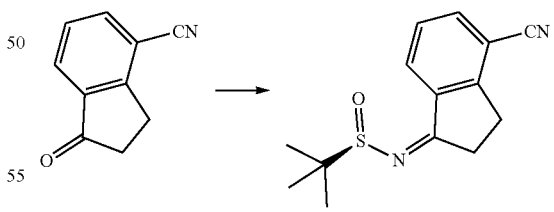

To 1-oxo-2,3-dihydro-1H-indene-4-carbonitrile INT-1 (42.5 g, 0.27 mol) and (R)-2-methylpropane-2-sulfinamide (36.0 g, 0.30 mol) in toluene (530 mL) was added titanium tetraethoxide (84.1 mL, 92.5 g, 0.40 mol) and the reaction mixture was heated at 60° C. for 12 h under $N_2$. The crude (R)—N-(4-cyano-2,3-dihydro-1H-indene-1-ylidene)-2-methylpropane-2-sulfinamide INT-4 was used directly in the next experiment. LCMS-ESI (m/z) calculated for $C_{14}H_{16}N_2OS$: 260.3; found 261.1 $[M+H]^+$, $t_R$=3.19 min.

8. (R)—N—((R)-4-cyano-2,3-dihydro-1H-inden-1-yl)-2-methylpropane-2-sulfinamide (INT-5)

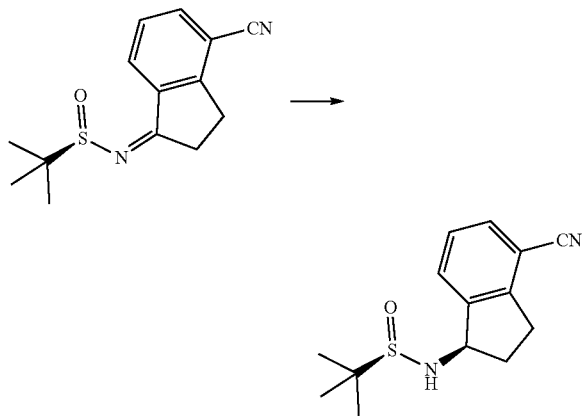

To a flask containing the crude suspension of (R)—N-(4-cyano-2,3-dihydro-1H-indene-1-ylidene)-2-methylpropane-2-sulfinamide INT-4 under $N_2$ was added THF (1.0 L) and the reaction mixture cooled to −78° C. Sodium borohydride (40.9 g, 1.08 mol) was added portion-wise over 30 mins. (The internal temperature did not rise during the addition). The reaction mixture was stirred at −78° C. for 30 mins, half out of the bath for 30 mins, then warmed to 0° C. over 1 h. The 0° C. reaction mixture was placed in an ice bath and quenched with brine (100 mL) followed by saturated sodium potassium tartrate (420 mL) and the Ti salts precipitated. The reaction mixture was diluted with EA (1.5 L) and stirred at room temperature overnight. The organic layers were decanted and washed successively with saturated $NH_4Cl$, water, and brine. The organic layers were dried over $MgSO_4$ and filtered through a pad of $MgSO_4$. The filtrate was concentrated to produce 52.9 g of crude (R)—N—((R)-4-cyano-2,3-dihydro-1H-inden-1-yl)-2-methylpropane-2-sulfinamide INT-5 as a brown oil, which was used directly in the next step. LCMS-ESI (m/z) calculated for $C_{14}H_{18}N_2OS$: 262.3; found 263.1 [M+H]$^+$, $t_R$=2.99 min. $^1$H NMR (400 MHz, CDCl$_3$) δ 7.89 (d, J=7.7, 1H), 7.56 (t, J=6.8, 1H), 7.36 (t, J=7.7, 1H), 4.97 (q, J=7.5, 1H), 3.50 (d, J=7.6, 1H), 3.22 (ddd, J=16.9, 8.8, 3.9, 1H), 3.01 (dt, J=22.4, 6.9, 1H), 2.70-2.53 (m, 1H), 2.15-1.95 (m, 1H), 1.33-1.20 (m, 9H).

9. (R)-1-amino-2,3-dihydro-1H-indene-1-yl)-4-carbonitrile (INT-6)

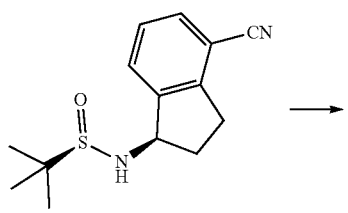

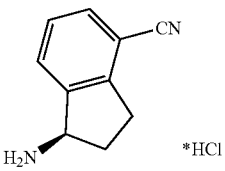

To crude (R)—N—((R)-4-cyano-2,3-dihydro-1H-inden-1-yl)-2-methylpropane-2-sulfinamide INT-5 (52.9 g, 0.20 mol) in MeOH (200 mL) was added 4N HCl in dioxane (152.0 mL, 0.60 mol) and the resulting yellow suspension was stirred at room temperature for 1.5 h. The crude reaction mixture was diluted with MeOH (500 mL) and filtered to remove some Ti by-products. The filtrate was concentrated and the resulting solid refluxed in acetonitrile (500 mL). The resulting white solid was collected to produce 13.0 g (31% over 3 steps) of the HCl salt of (R)-1-amino-2,3-dihydro-1H-indene-1-yl)-4-carbonitrile INT-6. LCMS-ESI (m/z) calculated for $C_{10}H_{10}N_2$: 158.2; found 142.0 [M-NH$_2$]$^+$, $t_R$=0.84 min. $^1$H NMR (400 MHz, DMSO) δ 8.61 (s, 3H), 7.96 (d, J=7.7, 1H), 7.83 (d, J=7.5, 1H), 7.52 (t, J=7.7, 1H), 4.80 (s, 1H), 3.23 (ddd, J=16.6, 8.7, 5.2, 1H), 3.05 (ddd, J=16.6, 8.6, 6.3, 1H), 2.62-2.51 (m, 1H), 2.15-2.01 (m, 1H). $^{13}$C NMR (101 MHz, DMSO) δ 148.09, 141.15, 132.48, 130.32, 127.89, 117.27, 108.05, 54.36, 39.08, 29.64. The free base can be prepared by extraction with 1N NaHCO$_3$ and DCM. LCMS-ESI (m/z) calculated for $C_{10}H_{10}N_2$: 158.2; found 142.0 [M-NH$_2$]$^+$, $t_R$=0.83 min. $^1$H NMR (400 MHz, CDCl$_3$) δ 7.52-7.38 (m, 2H), 7.23 (dd, J=17.4, 9.8, 1H), 4.35 (t, J=7.6, 1H), 3.11 (ddd, J=16.8, 8.7, 3.2, 1H), 2.89 (dt, J=16.9, 8.5, 1H), 2.53 (dddd, J=12.8, 8.1, 7.3, 3.2, 1H), 1.70 (dtd, J=12.8, 8.8, 8.0, 1H). $^{13}$C NMR (101 MHz, DMSO) δ 150.16, 146.67, 130.19, 128.74, 127.38, 117.77, 107.42, 56.86, 38.86, 29.14. Chiral HPLC: (R)-1-amino-2,3-dihydro-1H-indene-1-yl)-4-carbonitrile was eluted using 5% EtOH in hexanes, plus 0.05% TEA: 95% ee, $t_R$=23.02 min. The (S)-enantiomer INT-7 was prepared in an analogous fashion using (S)-2-methylpropane-2-sulfinamide. $t_R$ for (S)-enantiomer=20.17 min.

10. (R)-tert-butyl 4-cyano-2,3-dihydro-1H-inden-1-ylcarbamate (INT-8)

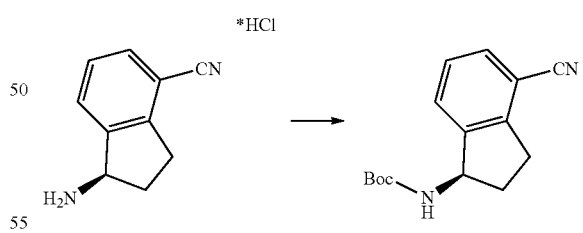

To (R)-1-amino-2,3-dihydro-1H-indene-1-yl)-4-carbonitrile HCl INT-6 (11.6 g, 59.6 mmol) in DCM (100 mL) at 0° C. was added TEA (12.0 mL, 131.0 mmol). To the resulting solution was added a solution of Boc anhydride (14.3 g, 65.6 mmol) in DCM (30 mL) and the reaction mixture stirred at room temperature for 1.5 h. The reaction mixture was washed with brine, and the organic layers were dried over MgSO$_4$ and filtered. Additional DCM was added to a total volume of 250 mL and Norit (4.5 g) was added. The product was refluxed for 15 mins and the hot mixture filtered through a pad of celite/silica. The filtrate was concentrated and recrystallized from EA (50 mL) and hexane (150 mL) to produce 12.93 g (84%) of (R)-tert-butyl 4-cyano-2,3-dihydro-1H-inden-1-ylcarbamate INT-8 as an off-white solid. LCMS-ESI (m/z) calculated for $C_{15}H_{18}N_2O_2$: 258.3; found 281.1 [M+Na]$^+$, $t_R$=3.45 min. Elemental Analysis determined for $C_{15}H_{18}N_2O_2$; C calculated=69.74%; found=69.98%. H calculated=7.02%; found=7.14%. N calculated=10.84%; found=10.89%. $^1$H NMR (400 MHz, CDCl$_3$) δ 7.64-7.49 (m, 2H), 7.34 (dt, J=7.7, 3.8, 1H), 5.36-5.20 (m, 1H), 4.78 (d, J=6.8, 1H), 3.20 (ddd, J=16.9, 8.9, 3.3, 1H), 3.02 (dt, J=25.4, 8.4, 1H), 2.82-2.53 (m, 1H), 1.88 (dq, J=13.2, 8.6, 1H), 1.55-1.44 (m, 9H). $^{13}$C NMR (101 MHz, DMSO) δ 155.52, 146.68, 146.32, 130.89, 128.70, 127.63, 117.51, 107.76, 77.98, 55.09, 31.88, 29.11, 28.19. Chiral HPLC: (R)-tert-butyl 4-cyano-2,3-dihydro-1H-inden-1-ylcarbamate was eluted using 2.5% EtOH in hexanes: >99.9% ee, $t_R$=19.36 min. The (S)-enantiomer INT-9 was prepared in an analogous fashion using (S)-1-amino-2,3-dihydro-1H-indene-1-yl)-4-carbonitrile HCl. $t_R$ for (S)-enantiomer=28.98 min.

11. Preparation of Indane Amide Oximes

A. To (R)- or (S)-tert-butyl 4-cyano-2,3-dihydro-1H-inden-1-ylcarbamate (1 eq) in EtOH (0.56 M) was added hydroxylamine hydrochloride (3 eq) and TEA (3 eq) and the reaction mixture heated at 85° C. for 1-2 h. The organic soluble amide oximes were isolated by removal of the solvent and partitioning between water and DCM. The water soluble amide oximes were chromatographed or used directly in the cyclization. Pure amide oximes can be obtained by recrystallization from alcoholic solvents.

B. (R)-tert-butyl 4-(N-hydroxycarbamimidoyl)-2,3-dihydro-1H-inden-1-ylcarbamate (INT-10)

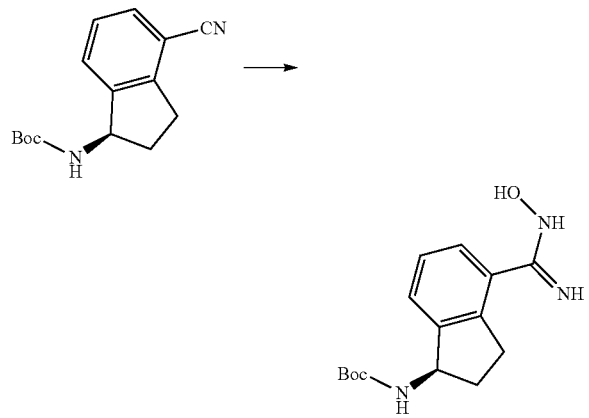

C. To (R)-tert-butyl 4-cyano-2,3-dihydro-1H-inden-1-ylcarbamate INT-8 (15.0 g, 58.2 mmol) in EtOH (100 mL) was added hydroxylamine hydrochloride (12.1 g, 174.2 mmol) and TEA (17.6 mL, 174.2 mmol) and the reaction mixture heated at 85° C. for 2 h. The solvents were removed and the resulting white solid was partitioned between water and DCM. The organic layers were dried over Na$_2$SO$_4$, concentrated, and recrystallized from isopropanol (50 mL) to afford 14.4 g (85%) of (R)-tert-butyl 4-(N-hydroxycarbamimidoyl)-2,3-dihydro-1H-inden-1-ylcarbamate INT-10 as white crystalline solid. LCMS-ESI (m/z) calculated for $C_{15}H_{21}N_3O_3$: 291.4; found 292.1 [M+H]$^+$, $t_R$=2.04 min. $^1$H NMR (400 MHz, DMSO) δ 9.53 (s, 1H), 7.38-7.32 (m, 1H), 7.32-7.12 (m, 3H), 5.68 (s, 2H), 4.97 (q, J=8.5, 1H), 3.07 (ddd, J=16.6, 8.7, 2.6, 1H), 2.86 (dt, J=16.8, 8.4, 1H), 2.30 (ddd, J=12.6, 7.6, 3.6, 1H), 1.75 (dq, J=12.3, 9.0, 1H), 1.44 (s, 9H).

12. Cyclization to Indane Oxadiazole Amines

A solution of the appropriate acid (1 eq), HOBt (1.3 eq), and EDC (1.3 eq) in DMF (0.08 M in acid) was stirred at room temperature under an atmosphere of N$_2$. After the complete formation of the HOBt-acid complex (1-3 h), the (R)- or (S)-amide oxime (1.1 eq) was added to the mixture. After complete formation of the coupled intermediate (ca. 0.5-2 h), the mixture was heated to 75-95° C. until the cyclization was complete (8-12 h). The reaction mixture was diluted with saturated NaHCO$_3$ and extracted with EA. The combined organic extracts were dried, concentrated, and either purified by chromatography (EA/hexanes) or taken on directly. The oxadiazole was treated with HCl (5N in dioxane, 5 eq) at 50-60° C. for 0.5-6 h. The reaction mixture could be extracted (DCM/NaHCO$_3$), or the resulting HCl salt concentrated, suspended in Et$_2$O, and collected. Pure indane amines can be obtained by recrystallization from alcoholic solvents or by chromatography.

13. (R)-tert-butyl 4-(5-(3-cyano-40isopropoxyphenyl)-1,2,4-oxadiazol-3-yl)-2,3-dihydro-1H-inden-1-ylcabamate (INT-12)

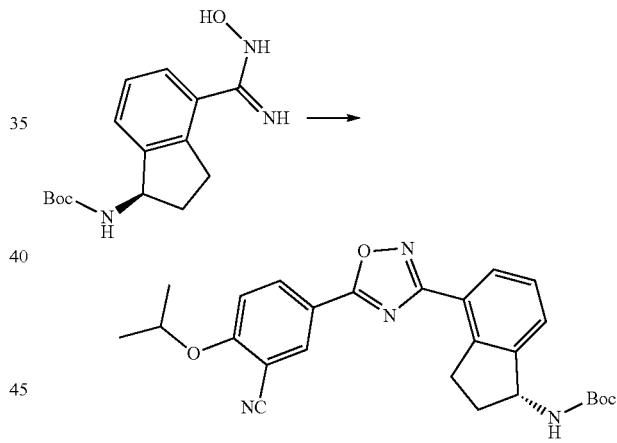

Prepared using the cyclization procedure described at step 12 above. To a solution of 3-cyano-4-isopropoxybenzoic acid (7.74 g, 37.7 mmol) in DMF (50 mL) was added HOBt (6.02 g, 44.6 mmol) and EDC (8.53 g, 44.6 mmol) at room temperature. The reaction was stirred for 2 h until complete formation of the HOBt-acid complex. (R)-tert-butyl 4-(N-hydroxycarbamimidoyl)-2,3-dihydro-1H-inden-1-ylcarbamate INT-10 (10.0 g, 34.3 mmol) was added and the reaction mixture stirred at room temperature for 2 h until the formation of INT-11, (R)-tert-butyl 4-(N-(3-cyano-4-isopropoxybenzolyloxy) carbamimidoyl)-2,3-dihydro-1H-inden-1-ylcarbamate. The mixture was partitioned between EA and NaHCO$_3$ and the organic layer was collected and dried over MgSO$_4$. INT-11 (16.3 g, 34.0 mmol) was re-dissolved in DMF (50 mL) and the mixture was heated to 95° C. for 12 hrs. The reaction was diluted with NaHCO$_3$ (200 mL) and extracted with EA (3×50 mL). The organic layer was dried over Na$_2$SO$_4$ and concentrated under reduced pressure to produce 12.8 g (81%) of (R)-tert-butyl 4-(5-(3-cyano-4-isopropoxyphenyl)-1,2,4-oxadiazol-3-yl)-2,3-dihydro-1H-inden-1-ylcarbamate INT-12 as a light brown solid and used without further purification in the next step. LCMS-ESI (m/z) calculated for $C_{26}H_{28}N_4O_4$: 460.5; found 483.2 [M+Na]$^+$, $t_R$=4.25 min. $^1$H NMR (400 MHz, CDCl$_3$) δ 8.43 (d, J=2.1, 1H), 8.34 (dd, J=8.9, 2.2, 1H), 8.09 (d, J=7.6, 1H), 7.51 (d, J=7.5, 1H), 7.39 (t, J=7.6, 1H), 7.12 (d, J=9.0, 1H), 5.28 (d, J=8.2, 1H), 4.80 (hept, J=6.0, 1H), 3.47 (ddd, J=17.4, 8.9, 3.5, 1H), 3.27-3.03 (m, 1H), 2.68 (d, J=8.7, 1H), 1.87 (td, J=16.7, 8.5, 1H), 1.53-1.43 (m, 15H). $^{13}$C NMR (101 MHz, CDCl3) δ 173.00, 168.82, 162.70, 155.68, 145.31, 142.96, 134.05, 133.83, 128.25, 127.21, 126.79, 123.09, 116.78, 115.24, 113.52, 103.87, 79.52, 72.70, 55.72, 33.86, 31.47, 28.39, 21.70. Chiral HPLC: (R)-tert-butyl 4-(5-(3-cyano-4-isopropoxyphenyl)-1,2,4-oxadiazol-3-yl)-2,3-dihydro-1H-inden-1-ylcarbamate was eluted using 20% i-PrOH in hexanes: >99.9% ee, $t_R$=13.33 min. The (S)-enantiomer INT-13 was prepared in an analogous fashion using (S)-tert-butyl 4-cyano-2,3-dihydro-1H-inden-1-ylcarbamate using the procedures described at steps 11 and 12 above ($t_R$ for (S)-enantiomer=16.31 min).

14. (R)-5-(3-(1-amino-2,3-dihydro-1H-inden-4-yl)-1,2,4-oxadiazol-5-yl)-2-isopropoxy-benzonitrile hydrochloride and (S)-5-(3-(1-amino-2,3-dihydro-1H-inden-4-yl)-1,2,4-oxadiazol-5-yl)-2-isopropoxy-benzonitrile

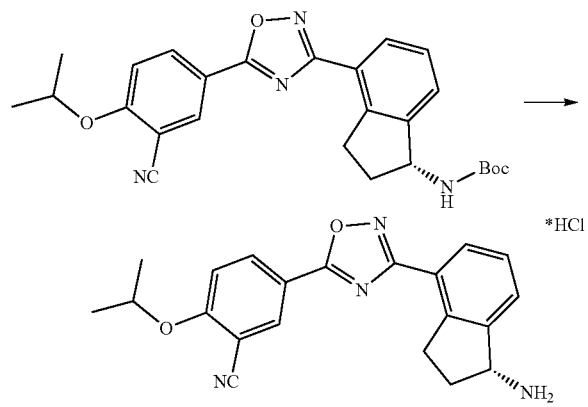

To (R)-tert-butyl 4-(5-(3-cyano-4-isopropoxyphenyl)-1,2,4-oxadiazol-3-yl)-2,3-dihydro-1H-inden-1-ylcarbamate (12.8 g, 27.8 mmol) in dioxane (200 mL) was added 4N HCl in dioxane (69 mL). The solution was heated to 55° C. for 1 h, and product precipitated. Dioxane was removed and the resulting solid suspended in ether and collected. The material was recrystallized from MeOH (200 mL) to produce 8.11 g (81%) of (R)-5-(3-(1-amino-2,3-dihydro-1H-inden-4-yl)-1,2,4-oxadiazol-5-yl)-2-isopropoxybenzonitrile as the HCl salt. LCMS-ESI (m/z): calcd for: $C_{21}H_{20}N_4O_2$: 360.4; found 383.2 [M+Na]$^+$, $t_R$=2.49 min. Elemental Analysis and NMR spectra determined for $C_{21}H_{21}N_4O_2Cl*0.5H_2O$; C calculated=62.14%; found=62.25%. H calculated=5.46%; found=5.30%. N calculated=13.80%; found=13.84%. Cl calculated=8.73%; found=8.34%. $^1$H NMR (400 MHz, DMSO) δ 8.71 (s, 3H), 8.49 (d, J=2.3, 1H), 8.39 (dd, J=9.0, 2.3, 1H), 8.11 (d, J=7.6, 1H), 7.91 (d, J=7.6, 1H), 7.55 (t, J=8.5, 2H), 4.97 (hept, J=6.1, 1H), 4.80 (s, 1H), 3.47 (ddd, J=17.4, 8.7, 5.3, 1H), 3.23 (ddd, J=17.4, 8.6, 6.4, 1H), 2.55 (ddd, J=13.7, 8.3, 3.2, 1H), 2.22-1.97 (m, 1H), 1.38 (d, J=6.0, 6H). $^{13}$C NMR (101 MHz, CDCl$_3$) δ 173.28, 167.98, 162.53, 143.69, 141.29, 134.59, 133.80, 128.93, 128.11, 127.55, 122.72, 115.87, 115.24, 114.91, 102.46, 72.54, 54.38, 31.51, 29.91, 21.47. Chiral HPLC of the free base: (R)-5-(3-(1-amino-2,3-dihydro-1H-inden-4-yl)-1,2,4-oxadiazol-5-yl)-2-isopropoxy benzonitrile was eluted using 15% i-PrOH in hexanes plus 0.3% DEA: >99.9% ee, $t_R$=30.80 min. (S)-5-(3-(1-amino-2,3-dihydro-1H-inden-4-yl)-1,2,4-oxadiazol-5-yl)-2-isopropoxy-benzonitrile (compound 148) was prepared in an analogous fashion from (S)-tert-butyl 4-cyano-2,3-dihydro-1H-inden-1-ylcarbamate: >99.9% ee, $t_R$ for (S)-enantiomer=28.58 min.

Example 2

Treatment of SLE in a Murine Model

Compound 148 was tested for efficacy in an art-accepted mouse model for SLE: NZB×NZW F1 ("NZBWF1") mice develop an autoimmune disease closely resembling SLE. These mice spontaneously produce high levels of anti-dsDNA antibodies, an indicator of SLE, starting after 20 weeks of age. These mice develop hemolytic anemia, proteinuria, and progressive glomerulonephritis mediated by immune complex deposition in the glomerular basement membrane.

Six groups of NZBWF1 mice (Jackson Laboratories, stock #100008) were used in the study and were acclimated to the research facility for 7 weeks prior to the start of the study. Weekly measurements of proteinuria (excess serum proteins present in the urine) and body weight began at 20 weeks of age. At 23 weeks of age, the mice were assigned to groups in a balanced manner in order to achieve average body weight and average proteinuria measurements across the groups. One "naive" group consisting of 10 mice was euthanized at the start of treatment and used as a source of tissue for analysis. Treatment began at 23 weeks of age.

Figure 34B:
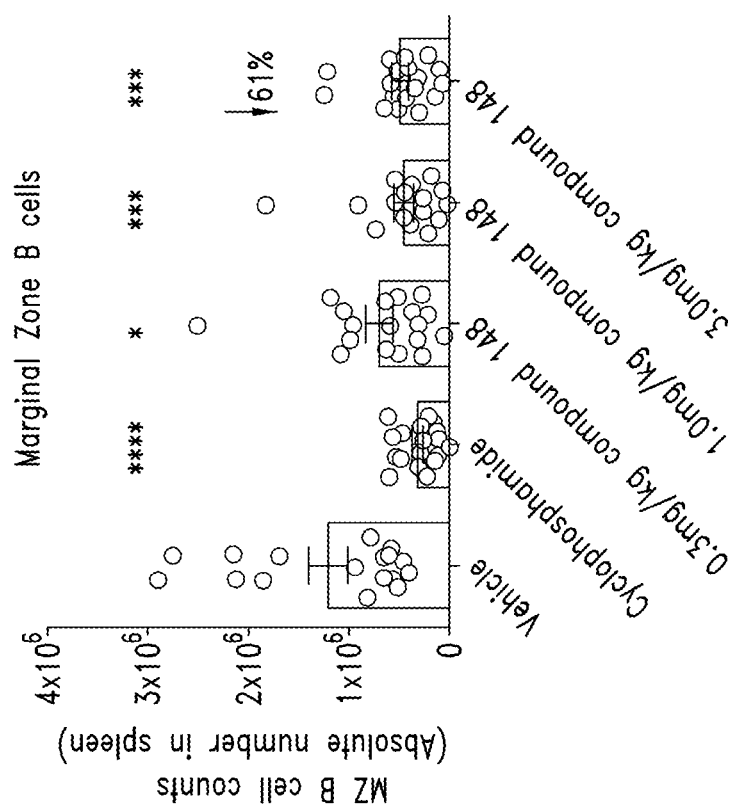
FIGS. 34A-38B relate to FIG. 8B and show absolute cell counts for several splenocytes in treated mice: CD19+ B cells (FIG. 34A); Marginal Zone B cells (FIG. 34B); Germinal Center B cells (FIG. 35A); Follicular B cells (FIG. 35B); plasma cells (FIG. 36); CD4+ T cells (FIG. 37A); CD8+ T cells (FIG. 37B); activated CD4+ T cells (FIG. 38A); naïve CD4+ T cells (FIG. 38B).
Figure 34A:
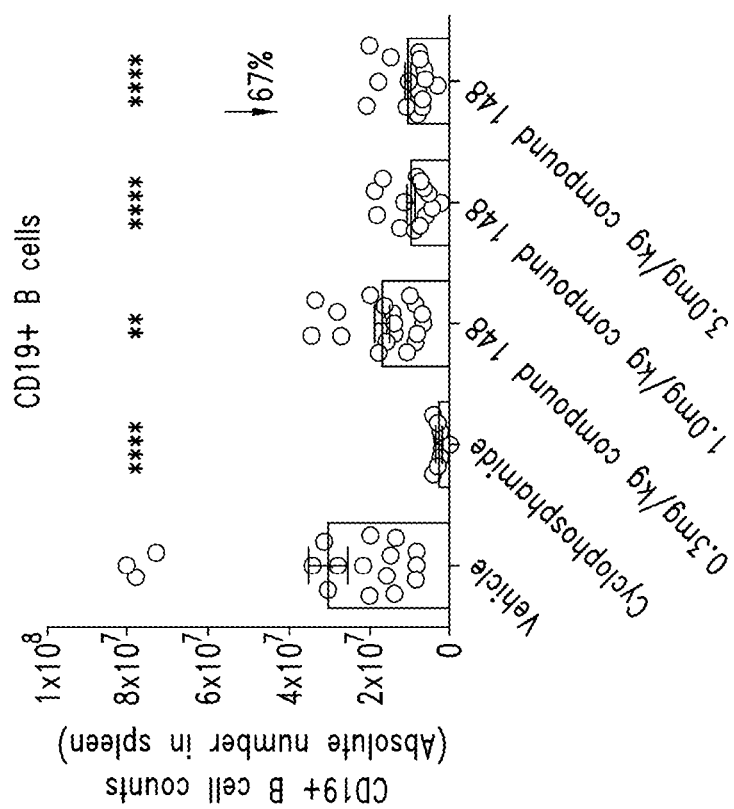
Figure 35B:
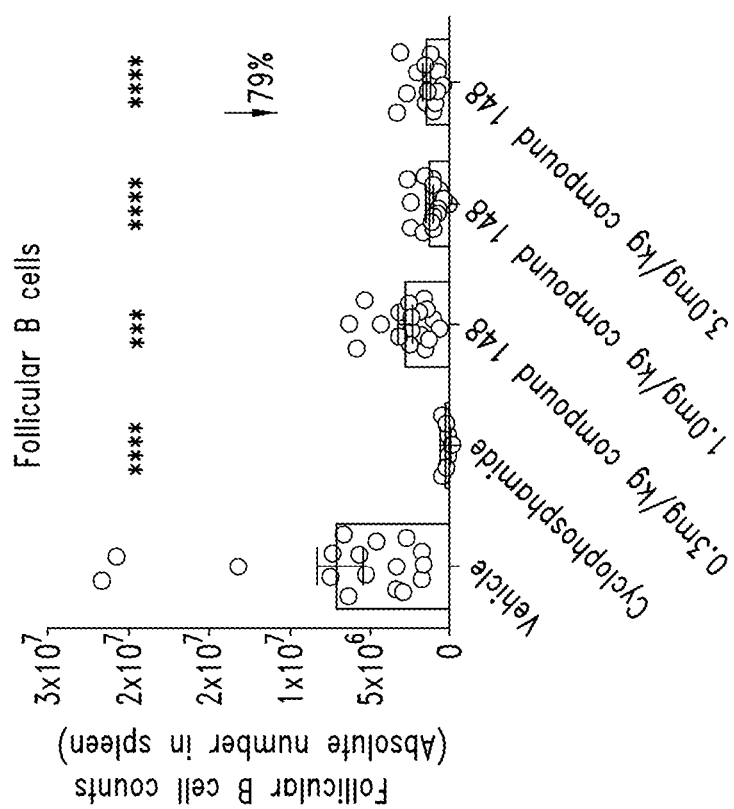
Figure 35A:
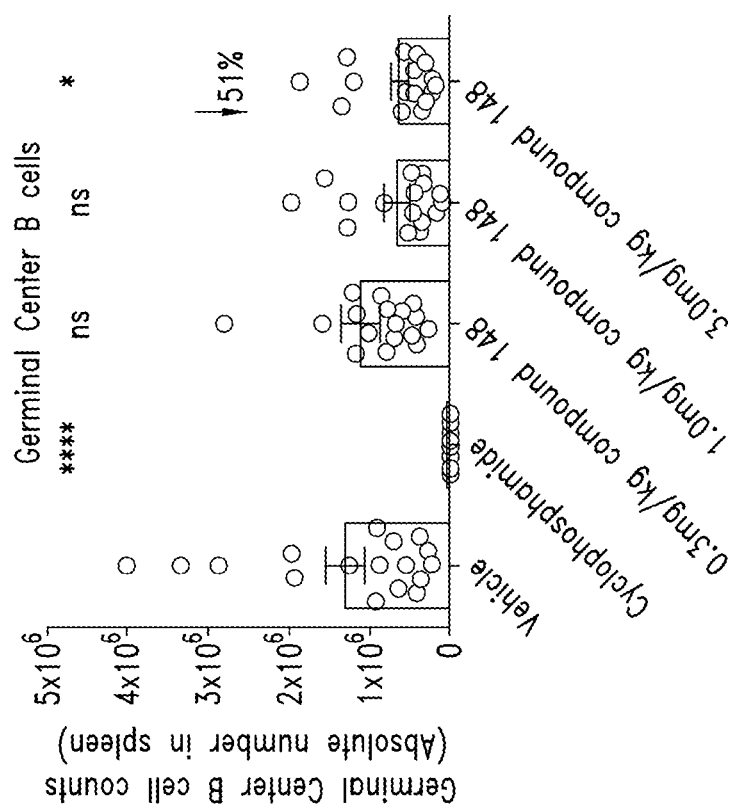
Figure 36:
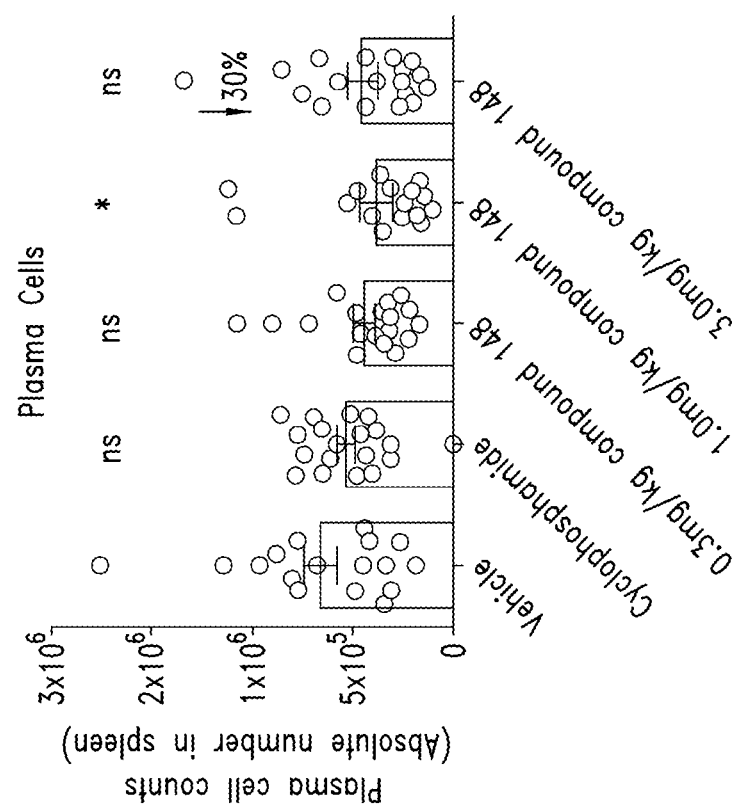
Figure 37B:
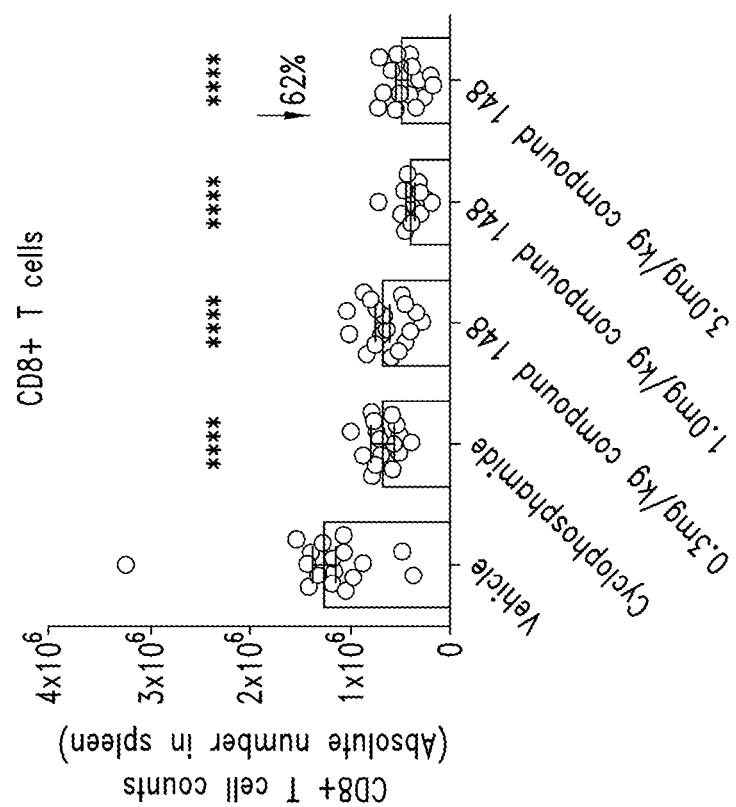
Figure 37A:
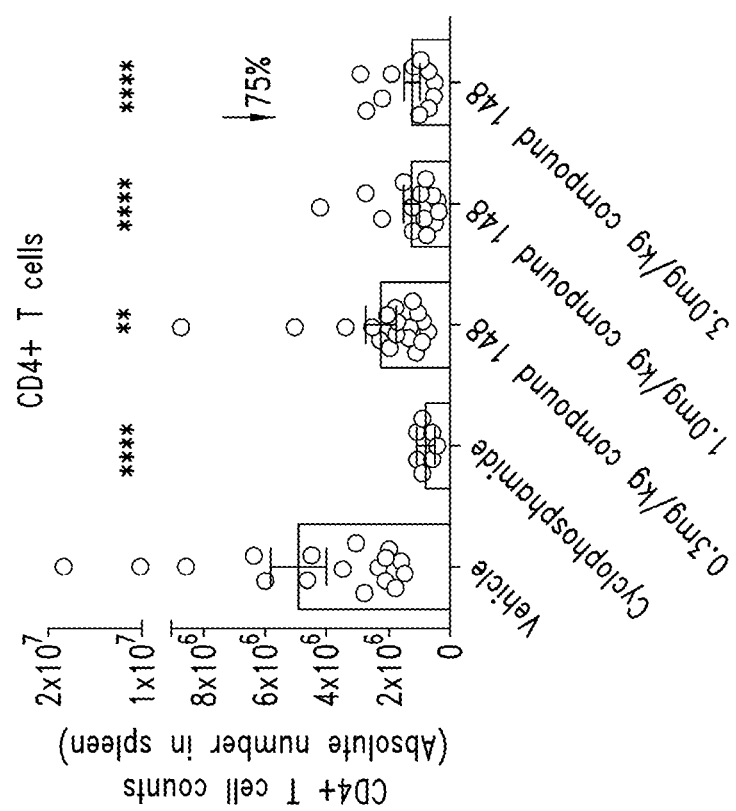

The five treatment groups were administered cyclophosphamide (positive control, 20 mice; introduced gradually to reduce toxicity (IP, once a week, 10 mg/kg at Week 23, 20 mg/kg Week 24; 50 mg/kg from Week 25 to Termination)), vehicle (negative control, 20 mice), or compound 148 (three groups of 20 mice), beginning at 23 weeks of age and observed over the course of 20 weeks. The three groups dosed with compound 148 received 0.3, 1.0, and 3.0 mg/kg PO QD, respectively (20 mice per dosage). Surviving animals were sacrificed at 42 weeks. See FIG. 1A. Treatment with cyclophosphamide increased body weights while vehicle- and treatment with compound 148-treated mice had similar body weights and minimal overall weight loss. See FIG. 34. Disease development was evaluated as disclosed in the following examples.

Example 3

Reduction of Proteinuria Scores

Figure 1A:
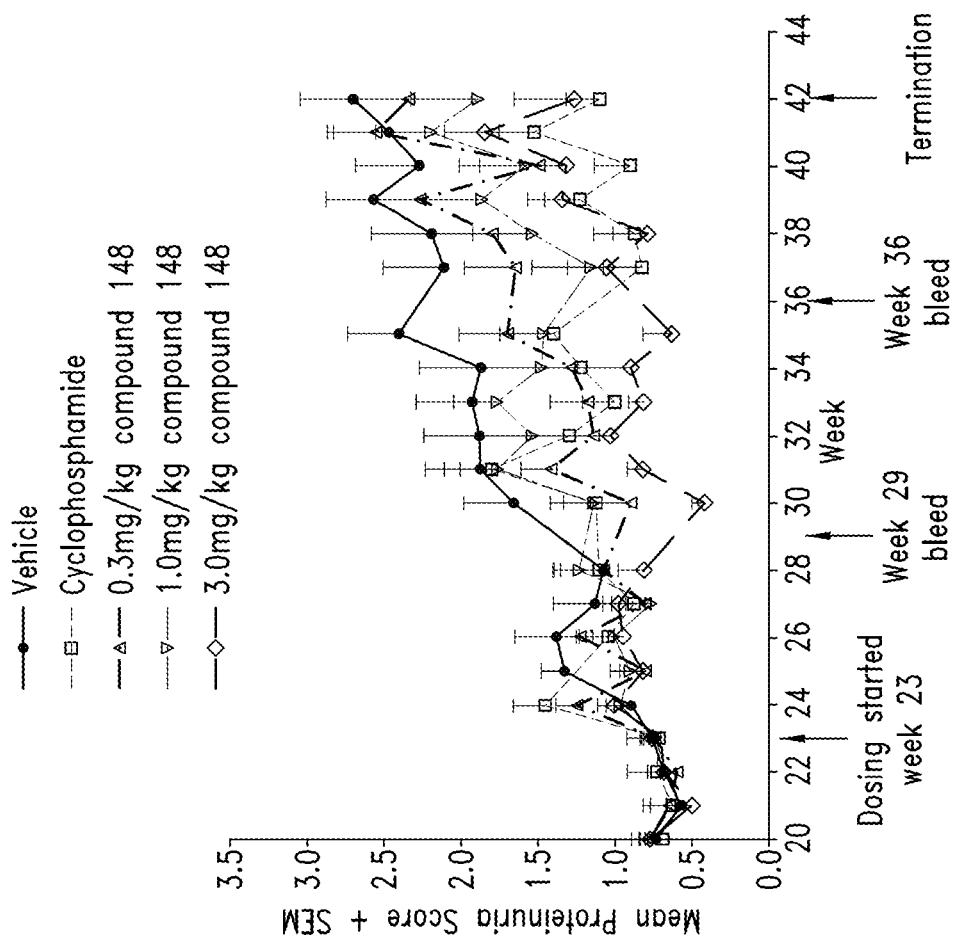
FIG. 1A shows mean proteinuria scores in NZBWF1 mice over the course of a 22-week study investigating the effects of an S1P1 modulator of the present disclosure (termed "compound 148") in this SLE mouse model. Weekly measurements began at week 20, and mice were administered: vehicle control PO QD (filled circle); 50 mg/kg cyclophosphamide IP ix/week (open square); 0.3 mg/kg compound 148 PO QD (open "up" triangle); 1.0 mg/kg compound 148 PO QD (open "down" triangle); or 3.0 mg/kg compound 148 PO QD (open diamond).

High levels of proteinuria are a strong indicator of SLE. As shown in FIG. 1A, proteinuria was measured weekly beginning at 20 weeks using urine dip sticks (Roche Diagnostics Chemstrip 2GP, cat. no. 11895397160, per manufacturer's protocol). Proteinuria was expressed as a score from 0 to 4 (0=no protein; 1=traces of protein (<30 mg/dL); 2=30-100 mg/dL; 3=100-500 mg/dL; 4=>500 mg/dL). Mean proteinuria scores over the course of the study are shown in FIG. 1B. As expected, mice treated with the vehicle developed proteinuria compared to the naïve group at the onset of treatment. Mice receiving compound 148 demonstrated lower proteinuria scores in a dose-dependent fashion compared to vehicle mice, and both the group receiving 3.0 mg/kg compound 148 and the group receiving cyclophosphamide showed significant improvement relative to vehicle (p<0.05; one-way ANOVA with Dunnett's comparison). Treatment with 3.0 mg/kg compound 148 demonstrated efficacy similar to cyclophosphamide.

Example 4

Reduction of Peripheral Lymphocyte Count and Serum BUN Levels

Figures 2A, 2B, 2C:
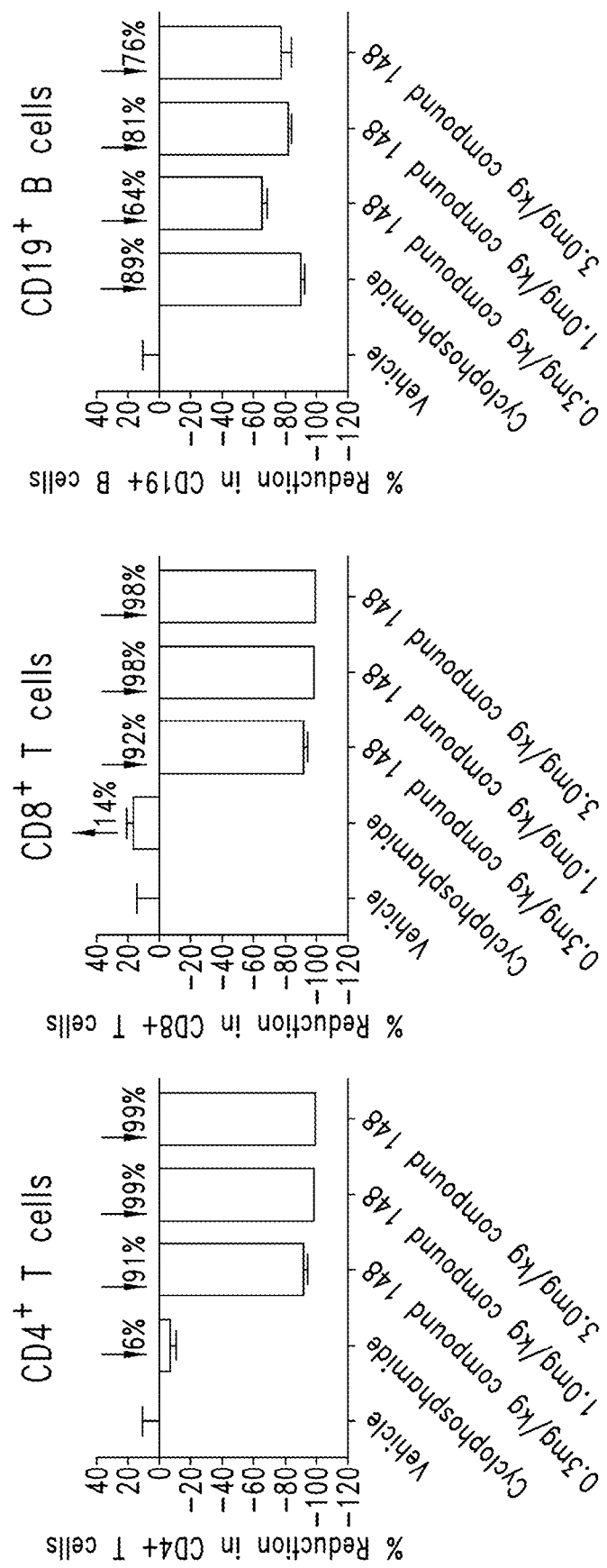
FIGS. 2A-2C show the effect of compound 148 on serum lymphocyte counts, as determined by flow cytometry.
Figure 3:
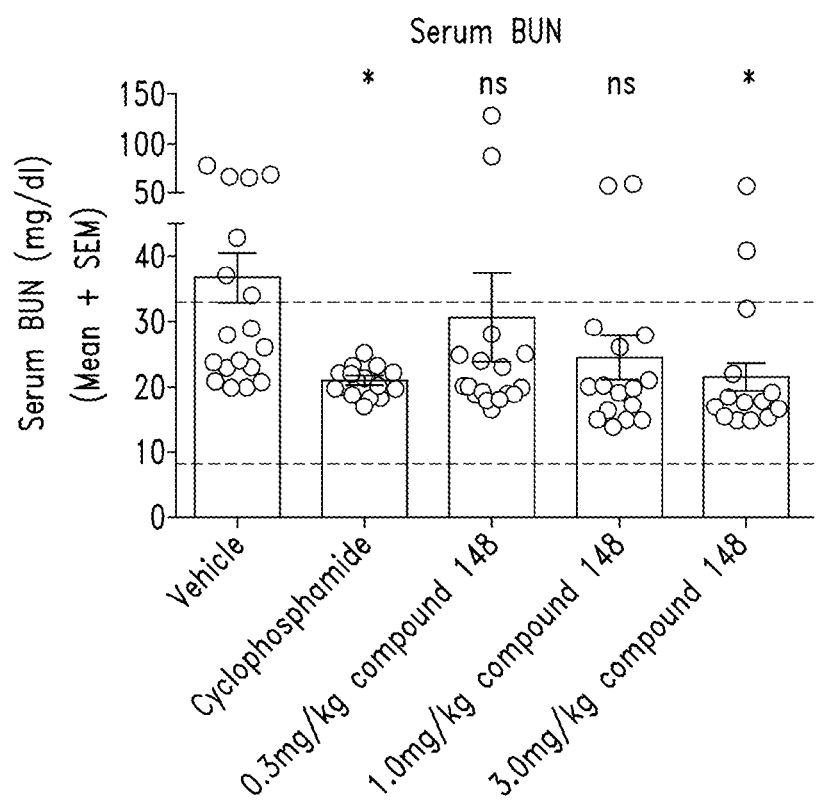
FIG. 3 shows serum Blood Urea Nitrogen (BUN) levels measured at termination.

Lymphocyte counts were measured from whole blood taken at 23, 31, and 36.5 weeks using flow cytometry. Cells were gated for CD4+ T cells, CD8+ T cells, and CD19+ B cells. As shown in FIGS. 2A-2C, all three doses of compound 148 significantly (>90%) reduced overall lymphocyte counts relative to vehicle (p<0.05; 2-tailed student's T-test). Significant reductions in $CD4^+$ T cells and $CD8^+$ T cells were observed with compound 148 relative to cyclophosphamide. Serum blood urea nitrogen (BUN) was also measured at termination to assess kidney function. As shown in FIG. 3, serum BUN was elevated in vehicle treated mice relative to expected serum levels (normal BUN range=8-33 mg/dl), and was decreased in all other treated groups. A significant reduction in serum BUN was observed for treatment with 3 mg/kg compound 148 or with cyclophosphamide (p<0.05, one-way ANOVA with Dunnett's comparison).

Example 5

Reduction of Kidney Weight, Tertiary Lymphatic Tissue, and Nephritic Lesions

Figure 4B:
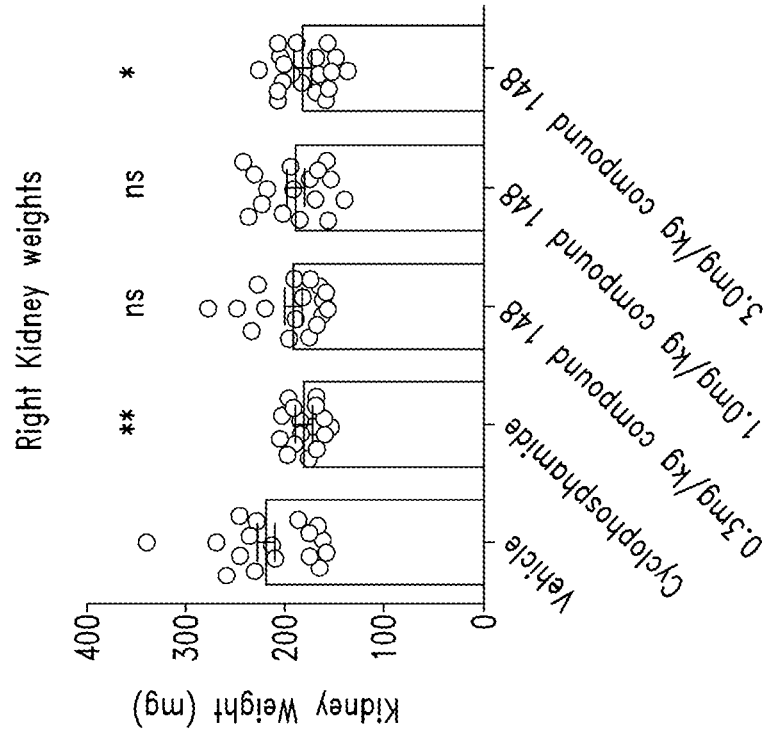
FIGS. 4A and 4B show mean kidney weights (left kidney, 4A; right kidney, 4B) taken from treated mice at termination.
Figure 4A:
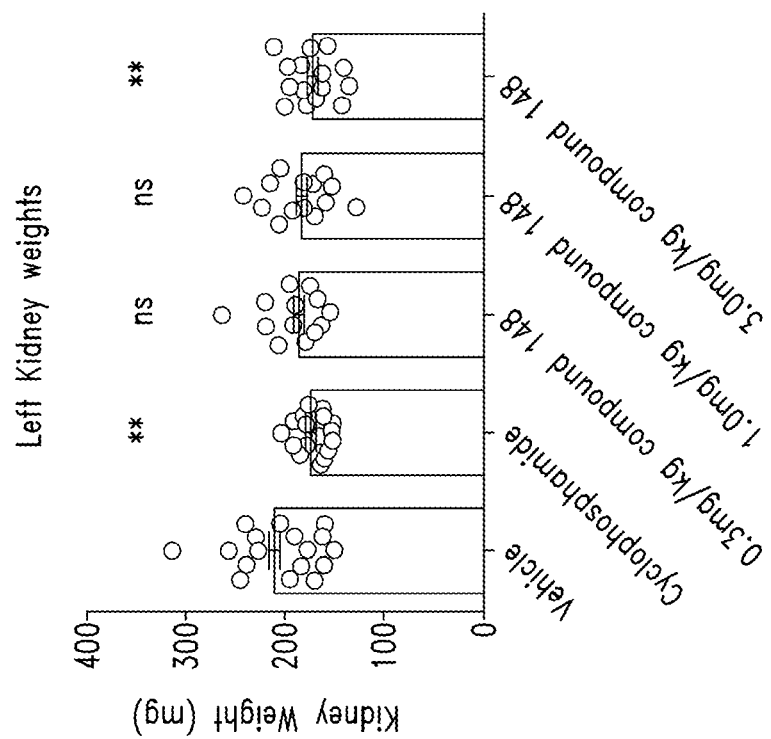

In SLE, inflammatory infiltrates known as Tertiary Lymphatic Tissue (TLT) accumulate in the kidney and spleen, among other tissues. As an indirect measure of disease progression, right and left kidneys were weighed (FIGS. 4A-4B) following termination at 42 weeks. Treatment with 3.0 mg/kg compound 148 or with cyclophosphamide significantly reduced kidney weight relative to vehicle (p<0.05; one-way ANOVA with Dunnett's comparison), indicating that disease progression was significantly slowed in these mice.

Figure 5:
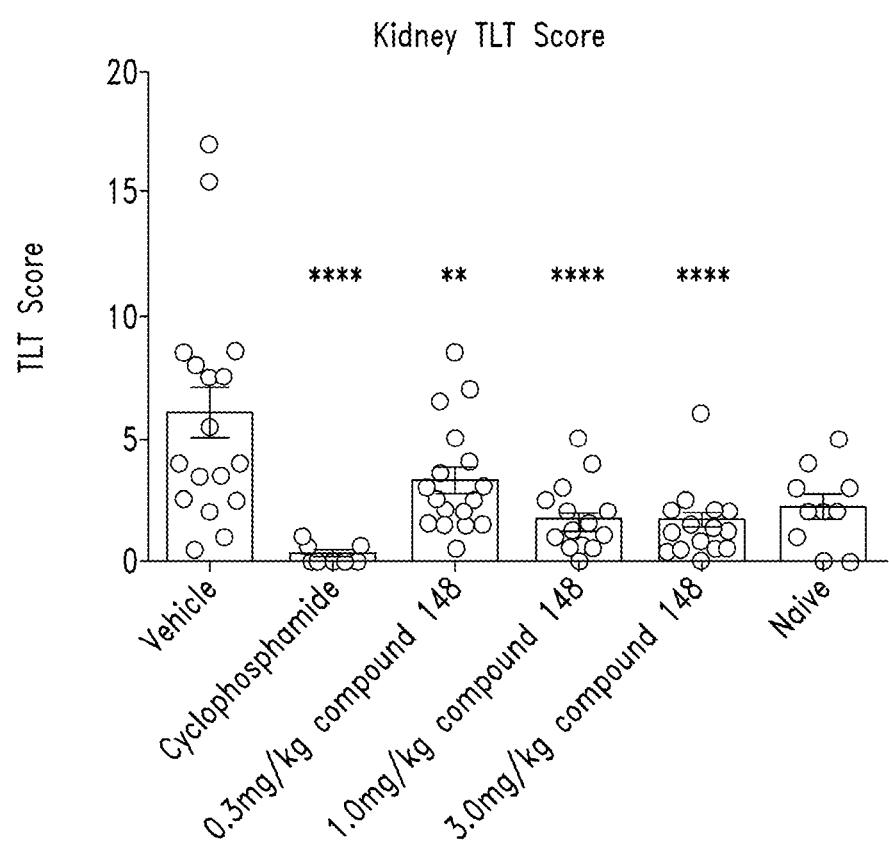
FIG. 5 shows Tertiary Lymphatic Tissue (TLT) scoring from kidneys of naïve NZBWF1 mice and NZBWF1 mice treated with vehicle, cyclophosphamide, 0.3, 1.0, or 3.0 mg/kg compound 148.

To directly assay disease progression, left kidney histology was observed and sections were stained using H&E (left kidney fixed in 4% PFA prior to staining for infiltrating PMN, lymphocytes, and TLTs) or PAS (for analysis of glomerular glycogen and glycoproteins). No neutrophils were observed. The number of aggregates was counted per section. As shown in FIG. 5, compound 148 significantly reduced TLT scores relative to vehicle (p<0.05; one-way ANOVA with Dunnett's comparison), although to a lesser degree than cyclophosphamide. Mice receiving 1.0 mg/kg or 3.0 mg/kg compound 148 had TLT scores similar to naïve mice, confirming fewer inflammatory infiltrates in kidneys of these mice.

Kidney lesions are another indicator of SLE progression. Kidney slides from test mice were stained with H&E and PAS, to evaluate interstitial infiltrates, tubular atrophy, and interstitial fibrosis (collectively, "tubular and interstitial lesions"), mesangial expansion, endocapillary and extracapillary proliferation, glomerular deposits, (collectively, "glomerular lesions"). Each lesion subtype was scored using a 4 point scale: 0=not present, 1=mild, 2=moderate and 3=severe. Average scores were calculated by multiplying the incidence of each grade by the value of the grade for each of the seven lesions and then adding the scores for the group. Thus, an incidence of 3 animals for grade 3 of a lesion equals a score of 9. The scores were then divided by the number of animals scored in the group.

Figure 6:
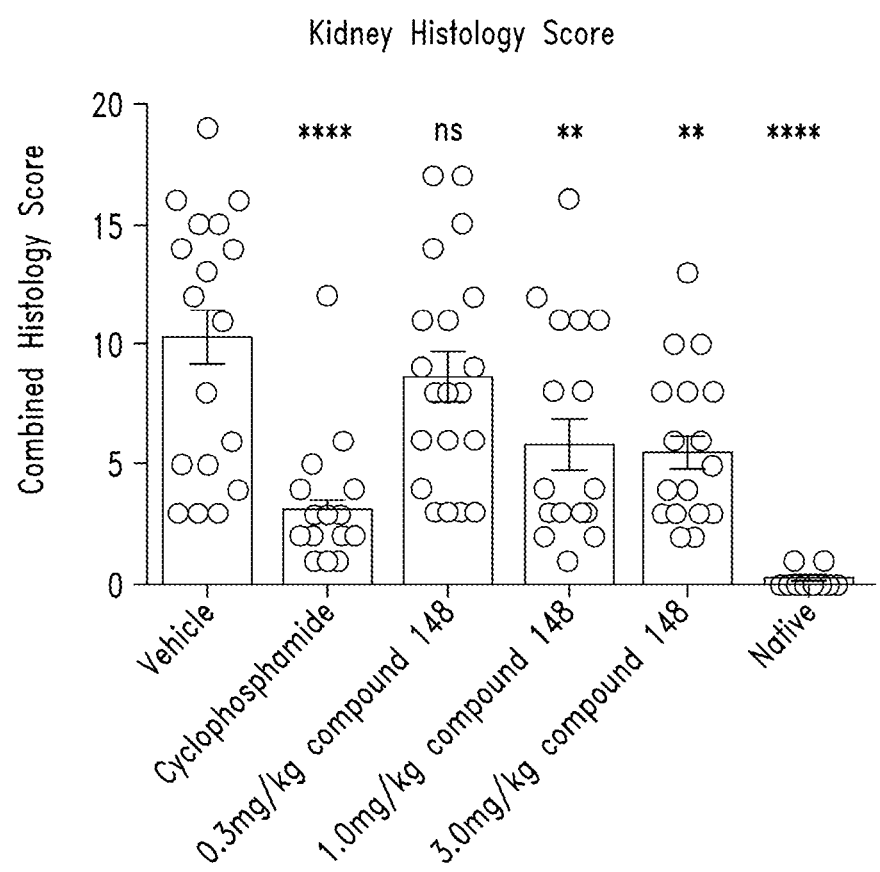
FIG. 6 shows combined histology scoring of glomerular, tubular, and interstitial lesions in treated and naïve NZBWF1 mice. Kidney sections were stained with H&E (hematoxylin and eosin for scoring tubular and interstitial lesions in test mice) or PAS (periodic acid Schiff for scoring glomerular lesions in test and naïve mice). Test mice were treated with vehicle, cyclophosphamide, 0.3, 1.0, or 3.0 mg/kg compound 148. Scoring criteria are described herein.

All slides were scored blind by assigning a random number to each animal and then affixing a temporary label with the random number to the slides. Scores were recorded using Graham StarTox software, version 3.1.0. The StarTox software has a setting that limits the screen display to the random number only, without group or animal number information for use while reading the slides. Treatment with 1.0 mg/kg and with 3.0 mg/kg compound 148 resulted in a dose-independent decrease in the severity of glomerular lesions, while animals treated with 0.3 mg/kg had a glomerular lesion score similar to that of the vehicle control (data not shown). The minimal score of 0.2 for untreated animals was attributed to biologic variation in the normal cellularity of the glomeruli. Treatment with compound 148 resulted in a dose-dependent decrease in tubular and interstitial lesions (p<0.05, one-way ANOVA with Dunnett's comparison) and was not statistically different from treatment with cyclophosphamide. Combined histology scores for each group of mice (glomerular lesion score plus tubular and interstitial lesion score) are shown in FIG. 6. As shown in FIG. 6, treatment with compound 148 showed a dose-related decrease in combined kidney lesion score for all three treatment groups as compared to vehicle.

Example 6

Reduction of Spleen Weight and Splenocyte Count

Figure 8A:
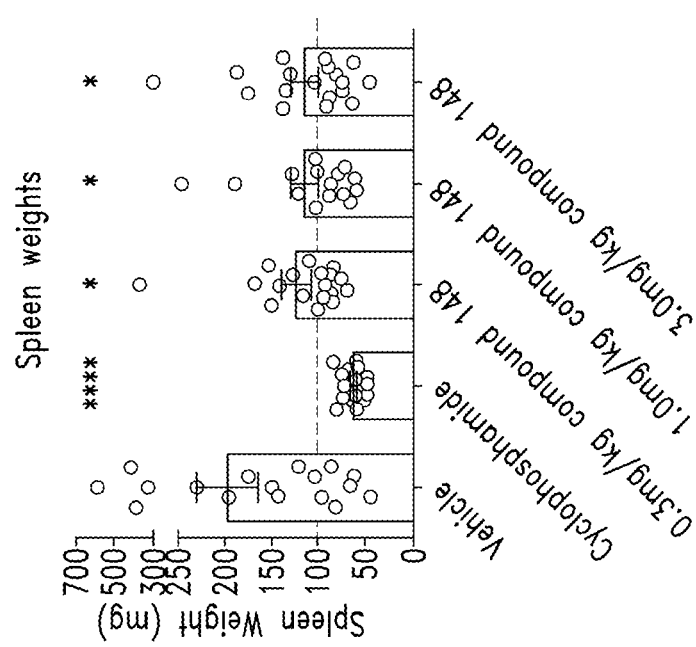
FIG. 8A shows spleen weights taken at termination from NZBWF1 mice treated with vehicle, cyclophosphamide, 0.3 mg/kg compound 148, 1.0 mg/kg compound 148, or 3.0 mg/kg compound 148.
Figure 8B:
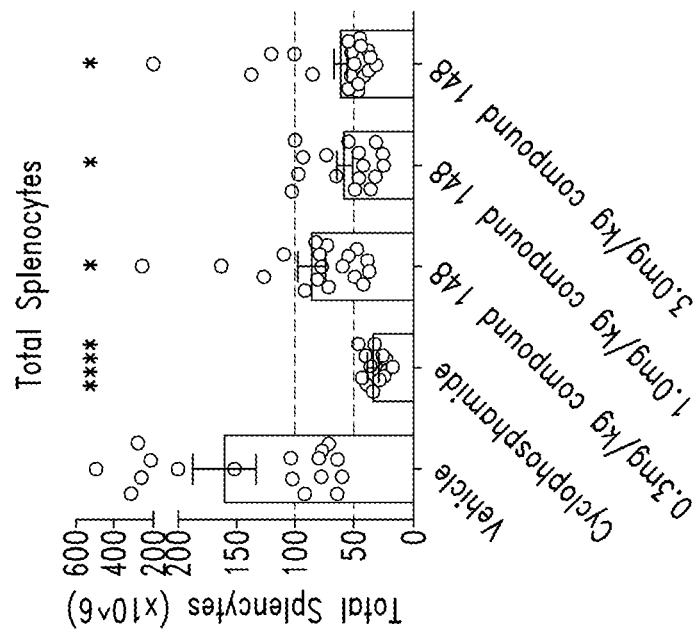
FIG. 8B shows splenocyte counts following RBC lysis.

To determine the effects of compound 148 on inflammatory infiltrate in the spleen, spleens were weighed at 42 weeks. As shown in FIG. 8A, spleen weights were significantly lower in all compound 148-treated groups relative to vehicle, indicating fewer inflammatory infiltrates in this organ (one-way ANOVA with Dunnett's comparison). Splenocyte suspensions were then prepared. RBCs were lysed and splenocytes were counted. As shown in FIG. 8B, total splenocyte counts were also reduced in all compound 148-treated groups relative to vehicle.

Figure 38B:
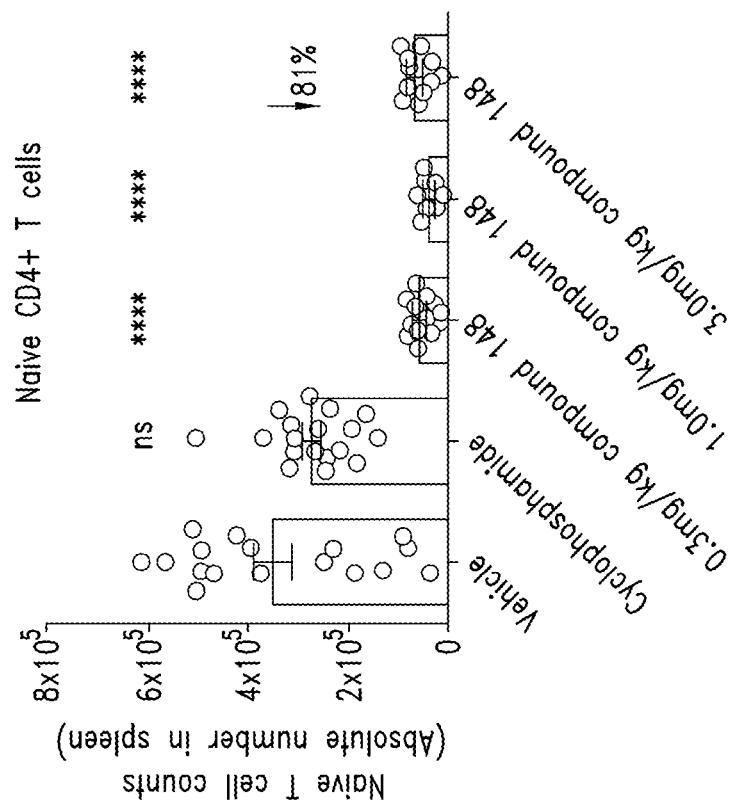
Figure 38A:
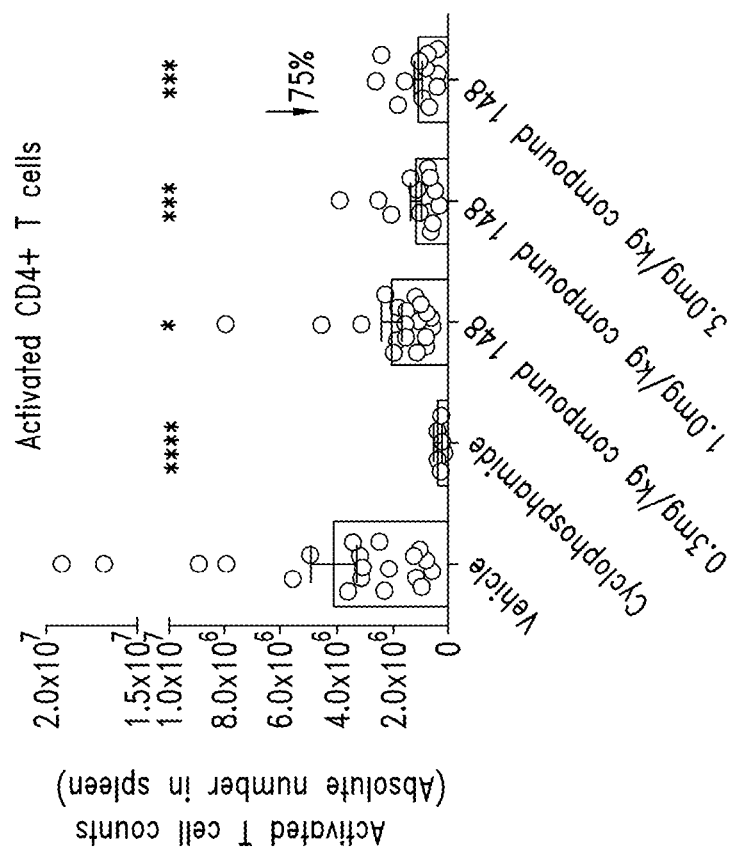

Cell counts of splenocyte subtypes are shown in FIGS. 34A-38B, which demonstrate that treatment with 3.0 mg/kg of compound 148 resulted in: a 67% reduction in $CD19^+$ B cell population (FIG. 34A; compare to 92% reduction with cyclophosphamide; raw counts not shown); a 61% reduction in Marginal Zone ("MZ") B cell population (FIG. 34B; compare to 74% reduction with cyclophosphamide; raw counts not shown); a 51% reduction in Germinal Center ("GC") B cell population treatment (FIG. 35A; compare to 99% reduction with cyclophosphamide; raw counts not shown); a 79% decrease in Follicular ("FO") B cells (FIG. 35B; compare to 96% reduction with cyclophosphamide; raw counts not shown); a 30% reduction in plasma cell population (FIG. 36; compare to 18% reduction with cyclophosphamide; raw counts not shown); a 75% decrease in $CD4^+$ T cell population (FIG. 37A; compare to 84% reduction with cyclophosphamide; raw counts not shown); a 62% reduction in $CD8^+$ T cell population (FIG. 37B; compare to 46% reduction with cyclophosphamide; raw counts not shown); a 75% reduction in activated $CD4^+$ T cell population (FIG. 38A; compare to 93% reduction with cyclophosphamide; raw counts not shown); and a surprising 81% reduction in naïve CD4+ T cells (FIG. 38B, compare to 47% reduction with cyclophosphamide; raw scores not shown).

Example 7

Reduction of Splenic pDC Cell Count

Figure 9:
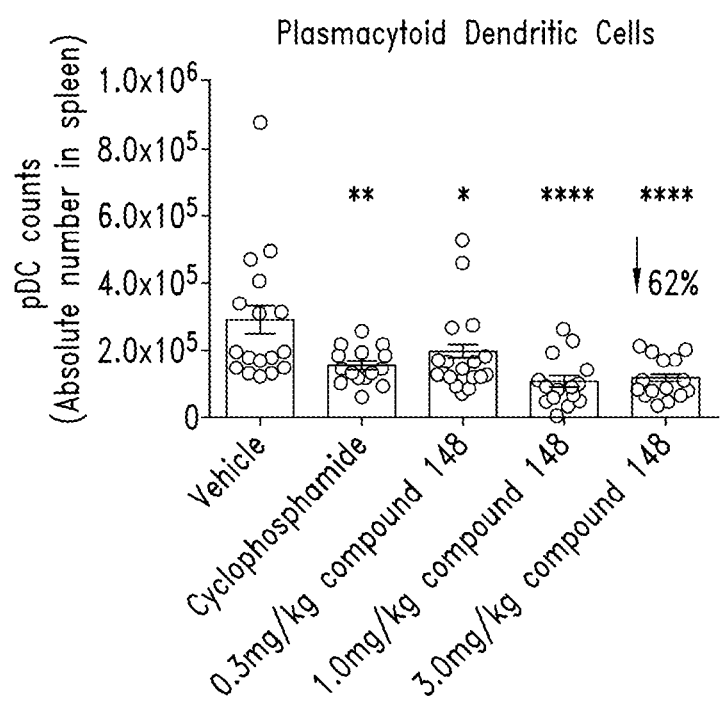
FIG. 9 shows plasmacytoid dendritic cell (pDC) counts from spleens of NZBWF1 mice treated with vehicle, cyclophosphamide, 0.3 mg/kg compound 148, 1.0 mg/kg compound 148, or 3.0 mg/kg compound 148.

Plasmacytoid dendritic cells (pDC) express IFNAR1 (Interferon alpha receptor 1), which amplifies the proinflammatory response to type 1 interferons (e.g., IFNα) that are associated with lupus. IFNAR activity is considered to be an important modulator of signal strength and duration in pDC and subsequent activation of T and B cells in the inflammatory response. pDC counts were measured at termination. As shown in FIG. 9, pDC counts were reduced in mice receiving 3.0 mg/kg compound 148 relative to vehicle in an approximately dose-dependent fashion. Notably, this represented a decrease of 62% relative to vehicle, whereas treatment with cyclophosphamide resulted in a 47% decrease relative to vehicle (raw scores not shown).

Example 8

Reduction of Anti-dsDNA Antibody Titers

Figure 7:
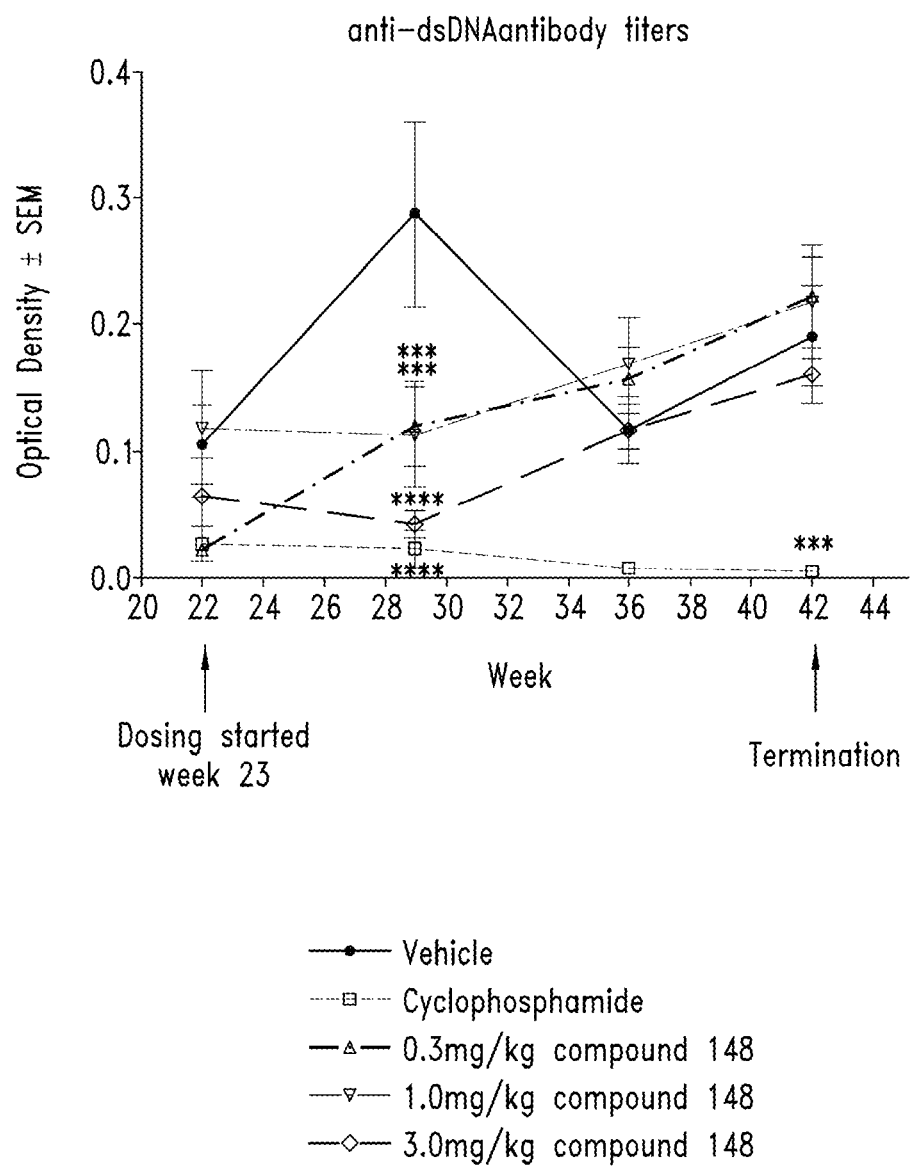
FIG. 7 shows anti-dsDNA antibody titers in NZBWF1 mice treated with vehicle, cyclophosphamide, 0.3 mg/kg compound 148, 1.0 mg/kg compound 148, or 3.0 mg/kg compound 148 over the course of the study. Titers were determined by measuring optical density in mouse sera taken at 22, 29, 36, and 42 weeks.

Serum anti-dsDNA antibody titers are used as an indicator of SLE state (see, e.g., Kavanaugh et al., "Guidelines for Clinical Use of the Antinuclear Antibody Test and Tests for Specific Autoantibodies to Nuclear Antigens", *Archives of Pathology & Laboratory Medicine,* 124:1, 71-81 (2000)) in most (although not all) patient populations, (see, Isenberg et al., *Rheumatology* 46:1052-1056, 2007). Titers were measured at 23, 31, 36.5, and 42 weeks. ELISA was performed using an anti-dsDNA ELISA kit (Shibayagi Co., Ltd., cat. no. RSHAKRDD061) following manufacturer's protocol. Results were expressed as optical density (OD) and as arbitrary units per mL. The ELISA standard curve was generated from a pool of sera from mice used a previous study with a known high concentration of anti-dsDNA antibodies. The highest concentration used in the standard curve was 1:100 of that pooled sera. All test samples were diluted 1000-fold for testing. Data was analyzed using http://www.elisaanalysis.com. As shown in FIG. 7, all three dosages of compound 148 resulted in decreased antibody titers at week 29, but, unlike mice receiving cyclophosphamide, this decrease was not sustained over the course of the study.

However, other immunomodulators have shown similarly limited effects on serum anti-dsDNA antibody titers in SLE mouse models (see Alperovich et al., *Lupus* 16(1):18-24 (2007), testing fingolimod in NZBWF1 mice; see also Ando et al. *Biochem. Biophys. Res. Commun.* 394(3):804-810 (2010), testing fingolimod in BXSB mice).

Example 9

Reduction in Expression of Inflammatory and Immune Genes

Figure 10B:
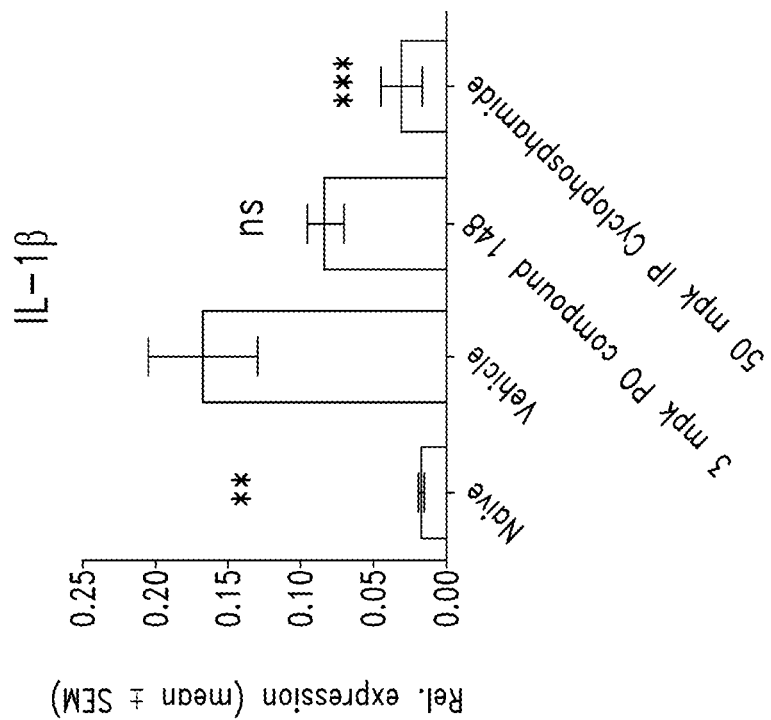
FIGS. 10A-16B show mRNA expression data from naïve and treated mice for several genes associated with inflammatory and/or immune response (10A-12B) or with fibrosis (13A-16B).
Figure 10A:
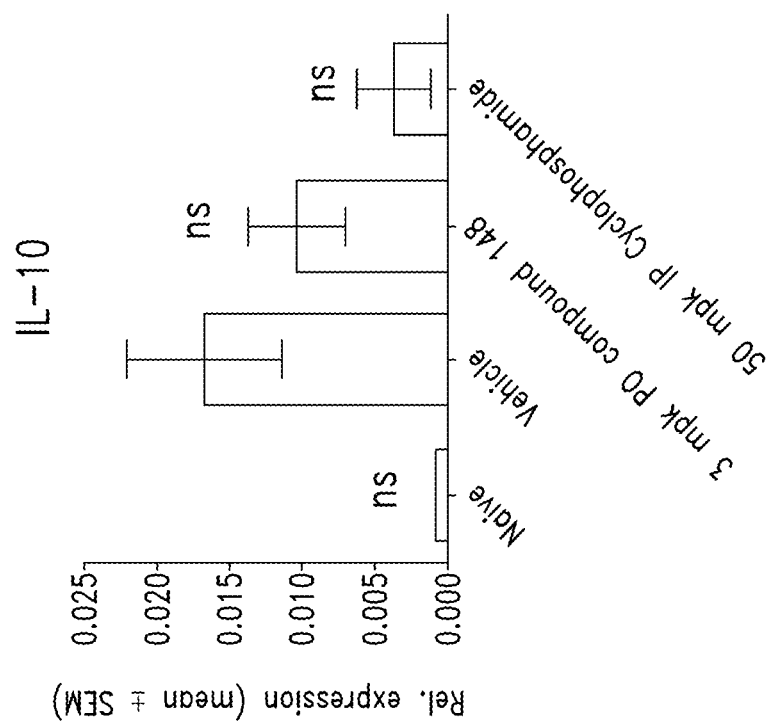
Figure 11B:
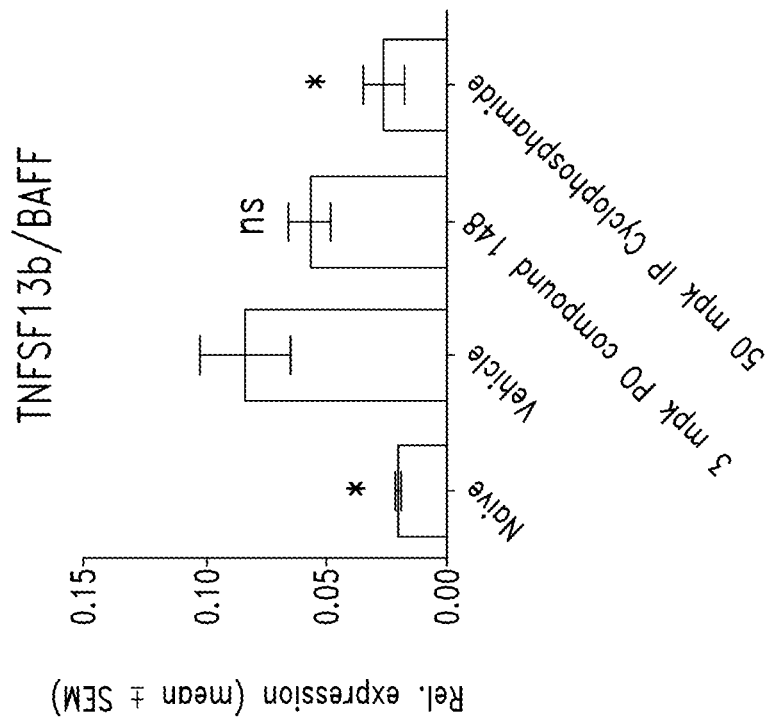
Figure 11A:
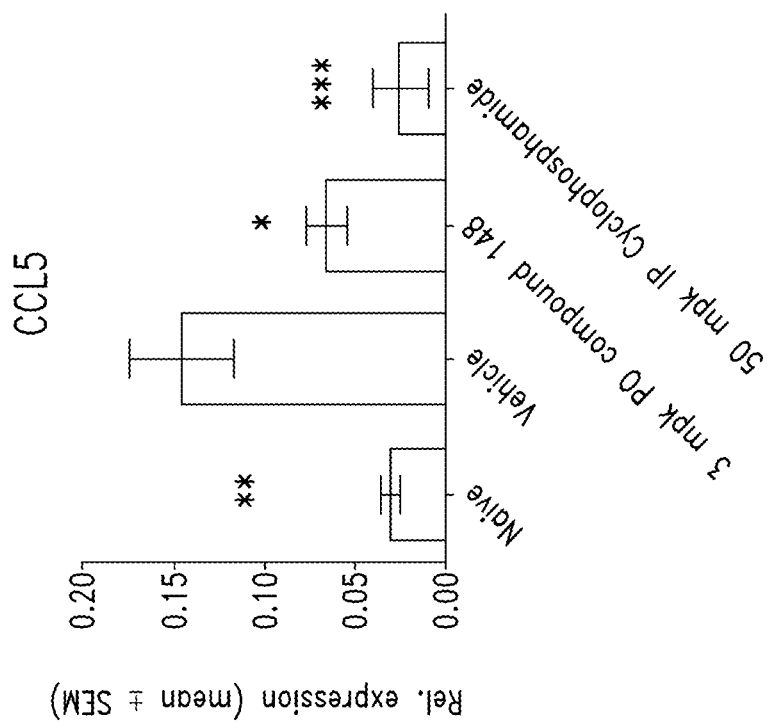
Figure 12B:
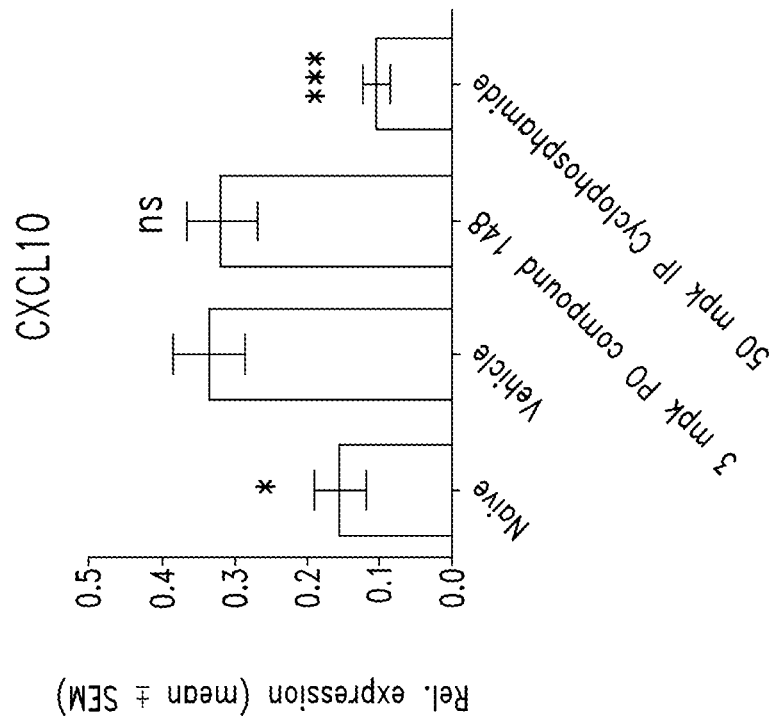
Figure 12A:
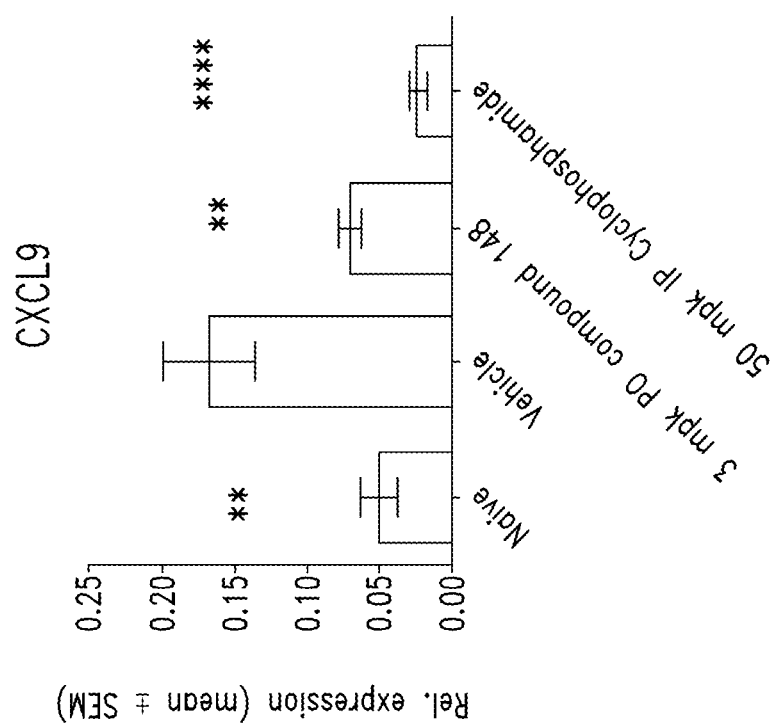

As explained above, SLE is characterized by aberrant recognition of healthy "self" tissue as antigenic. The resulting immune response is characterized by inflammation. To measure SLE status, mRNA levels were measured for an array of inflammatory and immune response genes from kidneys collected at termination or week 23 (naïve) and stored in RNAlater (n=5). mRNA was quantified using QuantiGene Multiplex Assay. Mice treated with 3 mpk PO compound 148 showed decreased levels of IL-10 (FIG. 10A), IL-1β (FIG. 10B), CCL5 (FIG. 11A), TNFSF13b/BAFF (FIG. 11B), CXCL9 (FIG. 12A) and CXCL10 (FIG. 12B) relative to control. These data show that treatment with compound 148 reduced expression of several inflammatory and immune response genes.

Example 10

Reduction of Expression of Fibrosis Genes

Figure 13B:
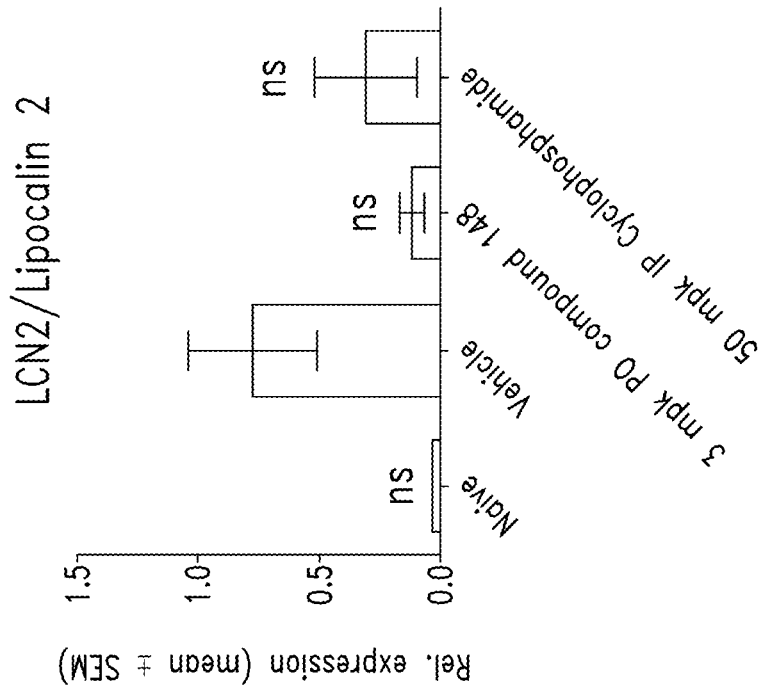
Figure 13A:
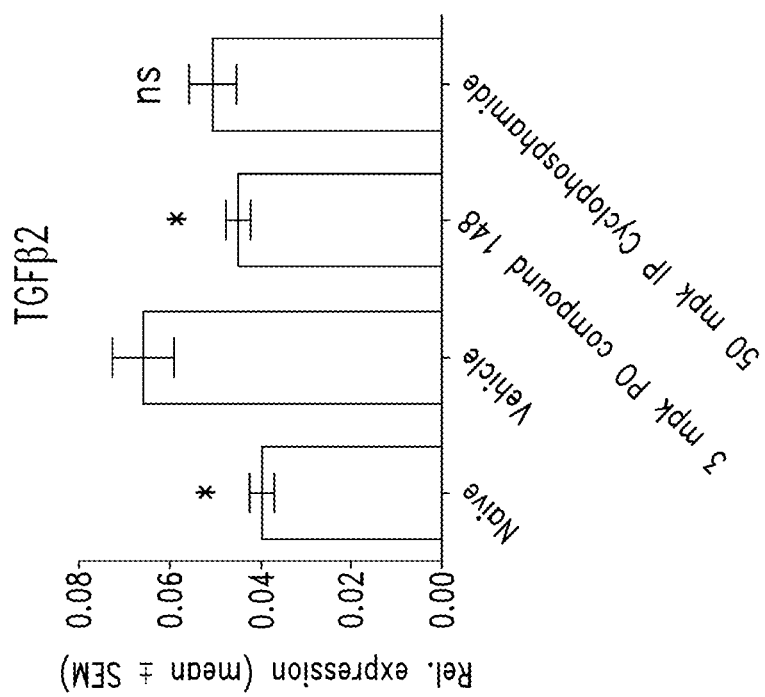
Figure 14B:
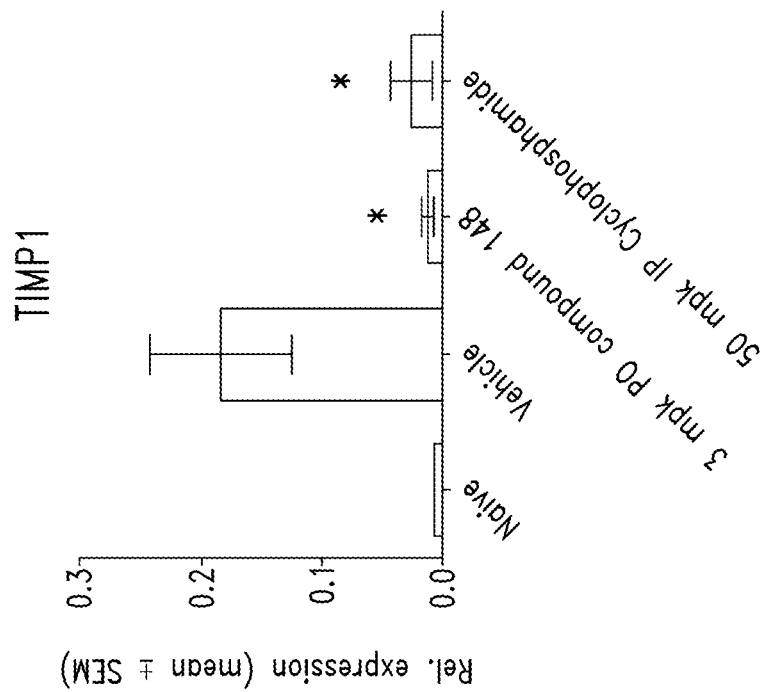
Figure 14A:
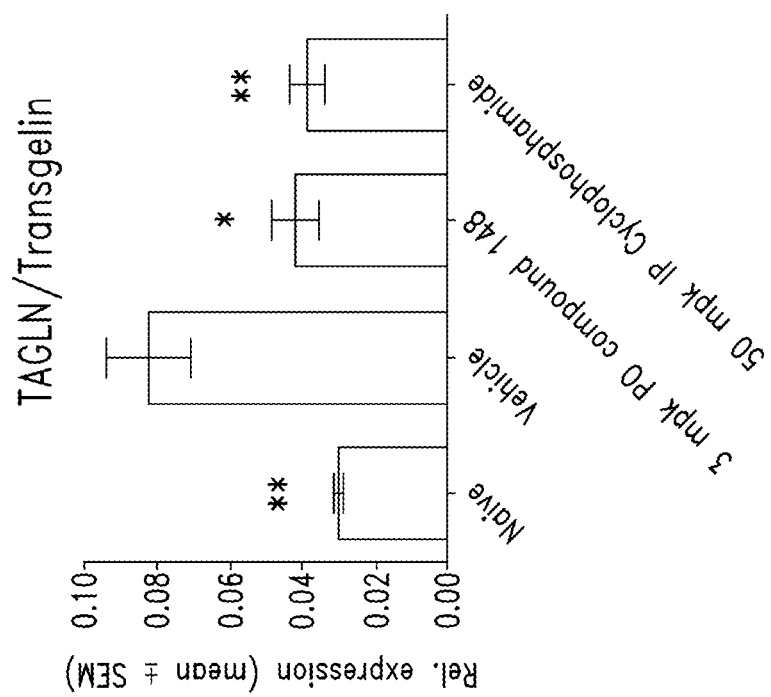
Figure 15:
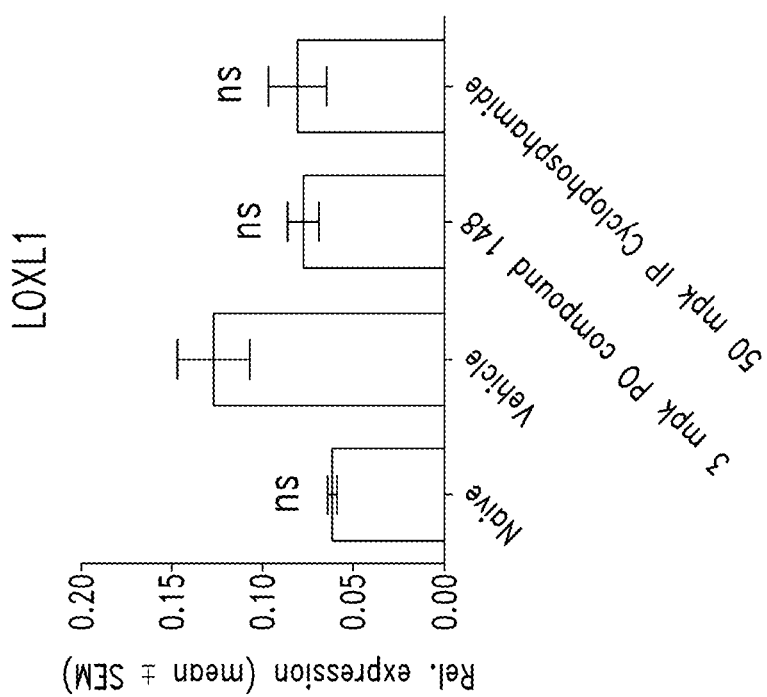
Figure 16B:
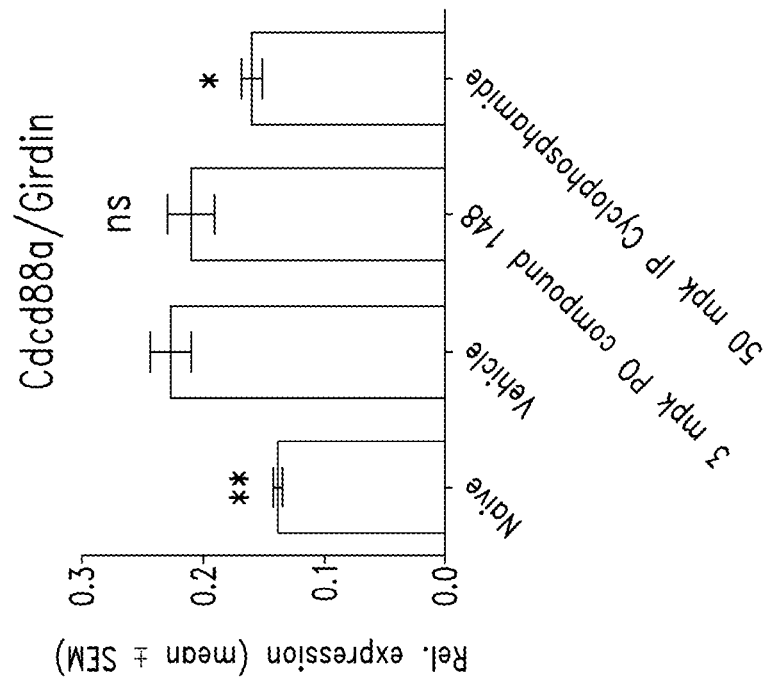
Figure 16A:
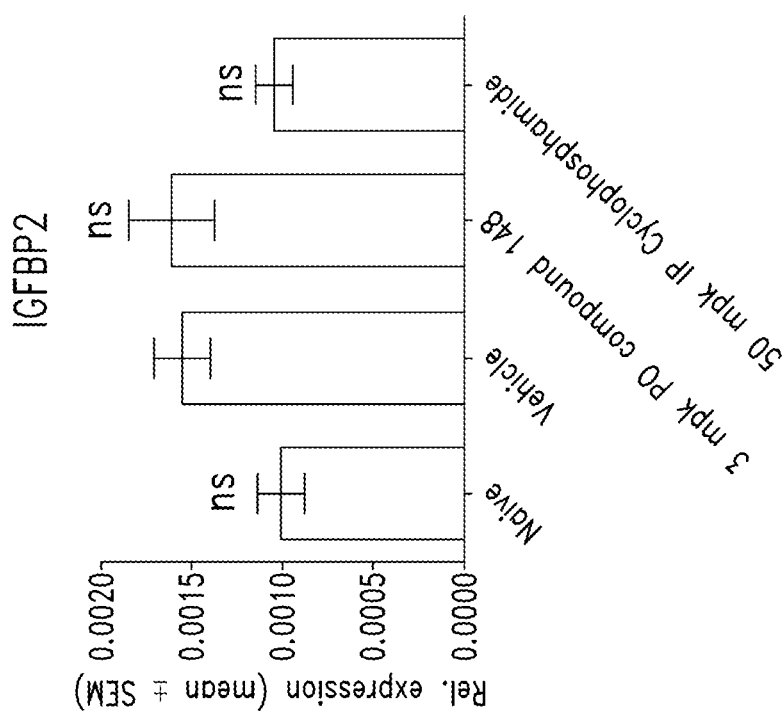

SLE-related inflammation can lead to fibrotic scarring. mRNA levels were measured for an array of profibrotic genes. Mice dosed with 3 mpk PO compound 148 showed decreased levels TGFβ2 (FIG. 13A), Lipocalin 2 (FIG. 13B), Transgelin (FIG. 14A), TIMP1 (FIG. 14B), LOXL1 (FIG. 15), and Cdcd88a/Girdin (FIG. 16B) relative to control. Expression signals of MMP10, IL-2, IL-6, and TNF were also measured, but were below LLOQ (data not shown). In contrast, IFGBP2 levels appeared to increase somewhat following administration of compound 148 (FIG. 16A). These data show that treatment with compound 148 decreased expression of several pro-fibrotic genes.

Example 11

Reduction of Expression of IFNα and IFNAR

Figure 17:
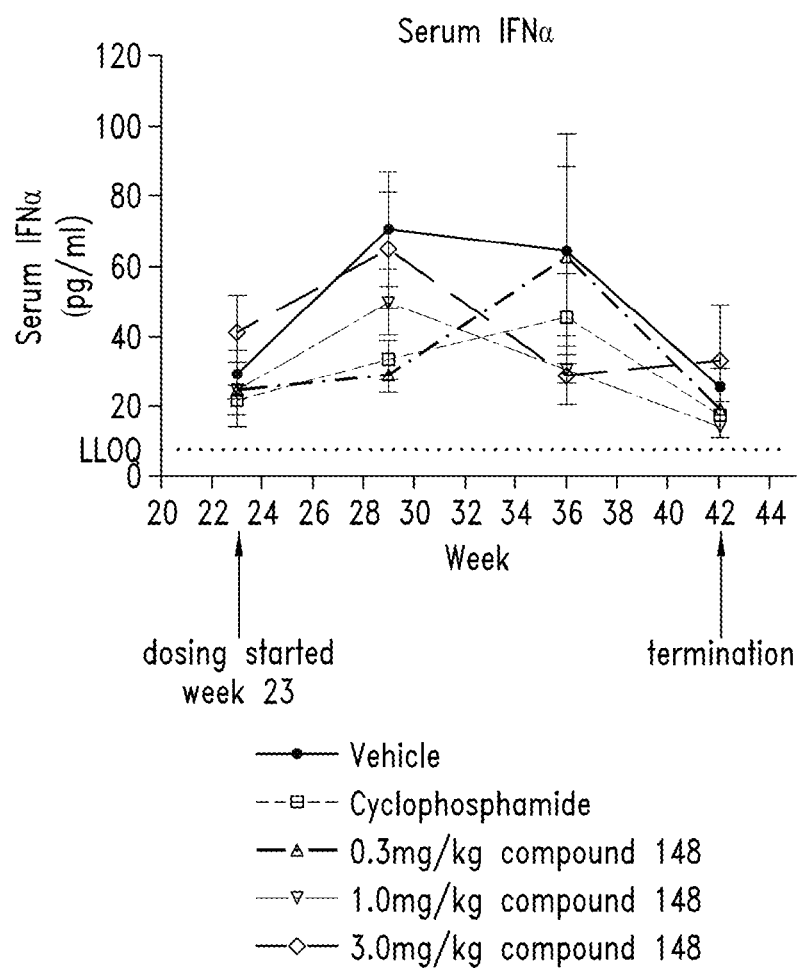
FIG. 17 shows serum IFNα levels measured in treated mice. Levels were measured at weeks 23, 29, 36, and 42.
Figure 18B:
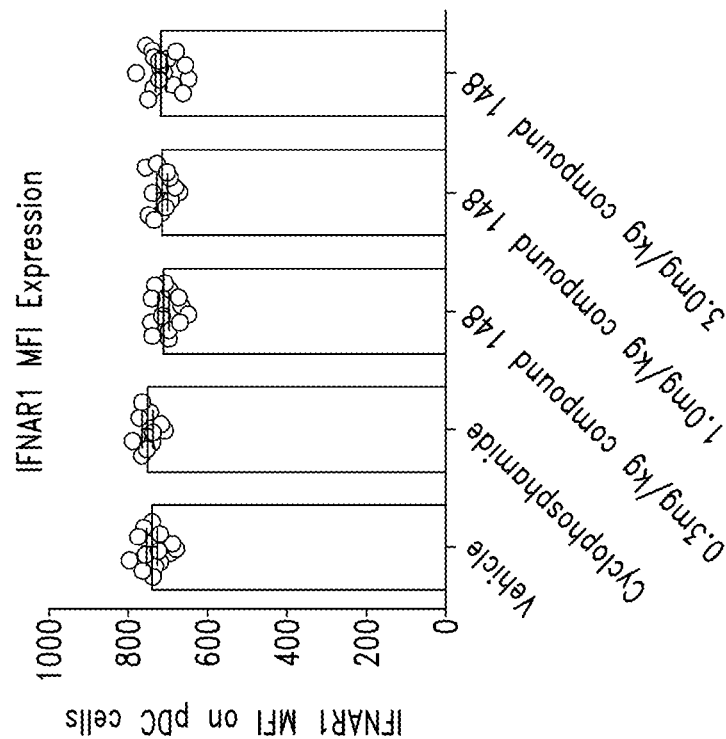
FIG. 18B shows average MFI (mean fluorescence intensity) of IFNAR1 expression in the pDCs.
Figure 18A:
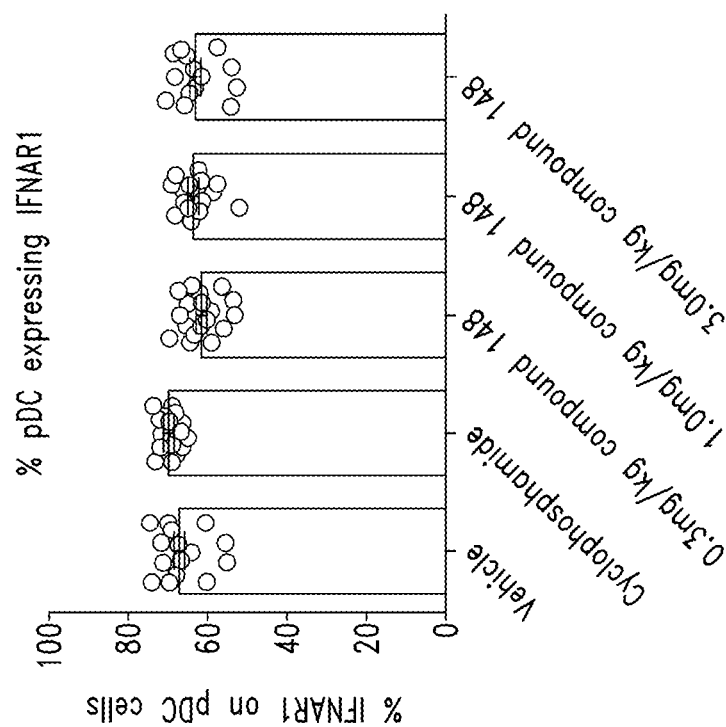
FIG. 18A shows the percentage of pDC splenocytes expressing IFNAR1.
Figure 19A:
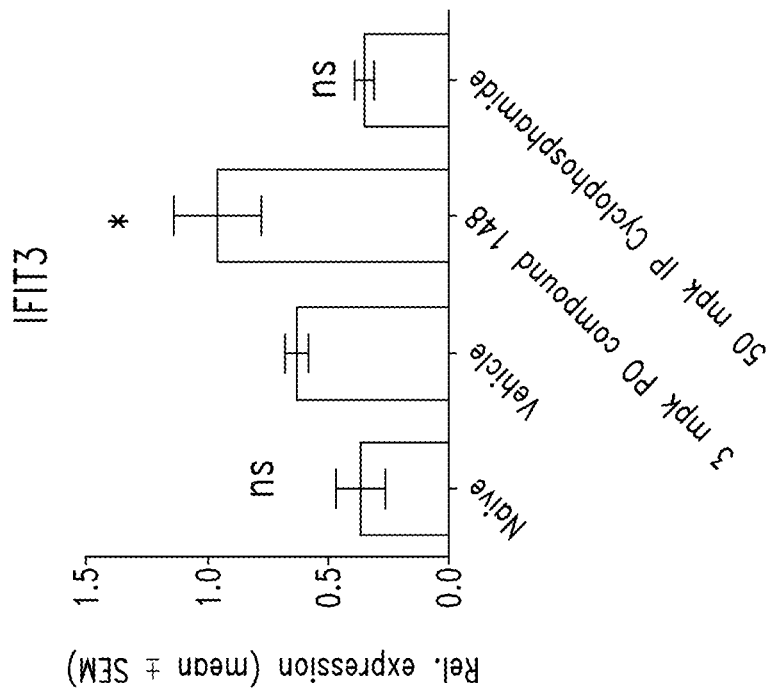
FIGS. 19A-32 show mRNA gene expression data from naïve and treated mice. mRNA expression of several genes known to be responsive to IFNα was determined.
Figure 19B:
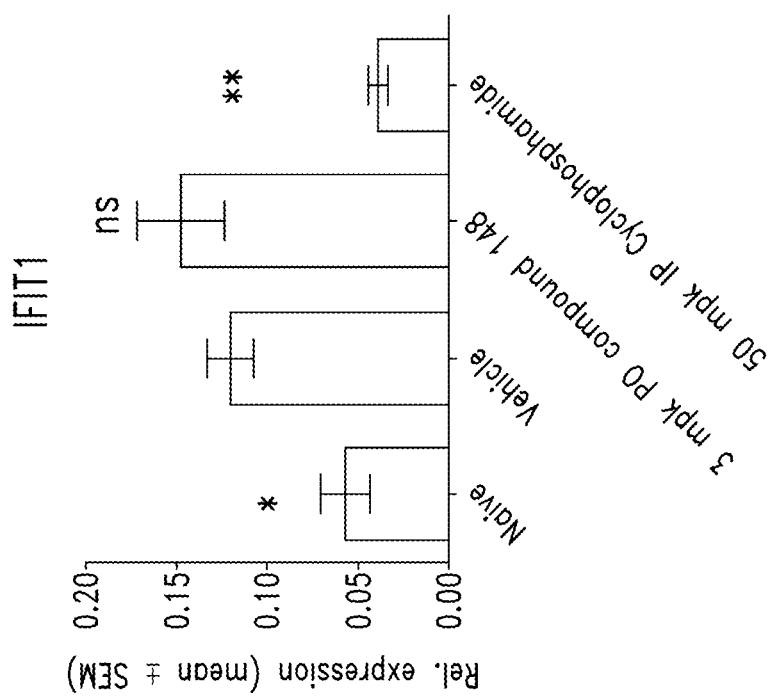
Figure 20B:
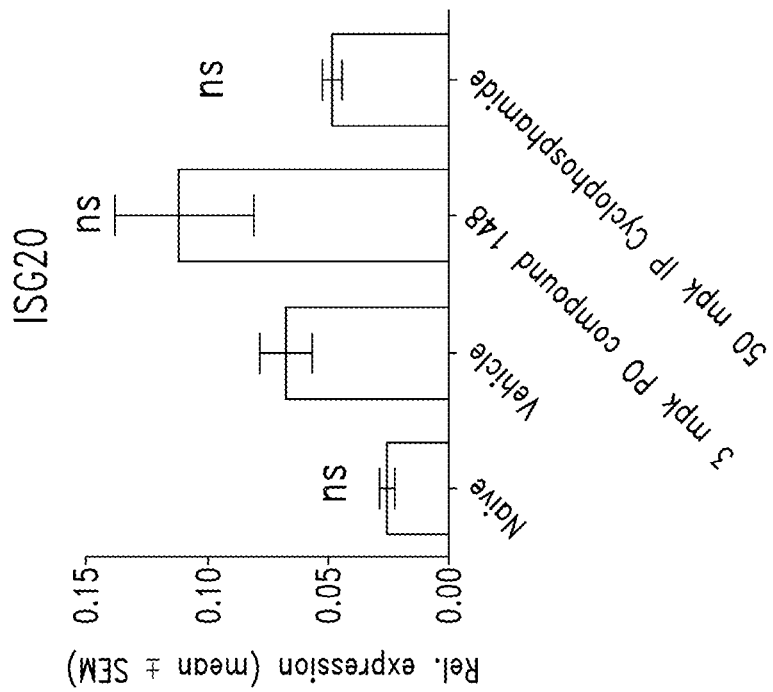
Figure 20A:
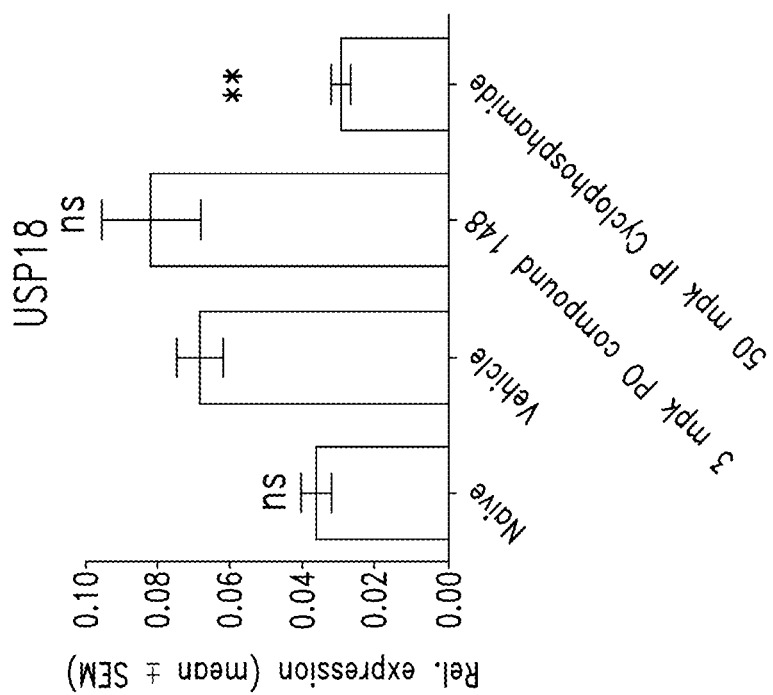
Figure 21B:
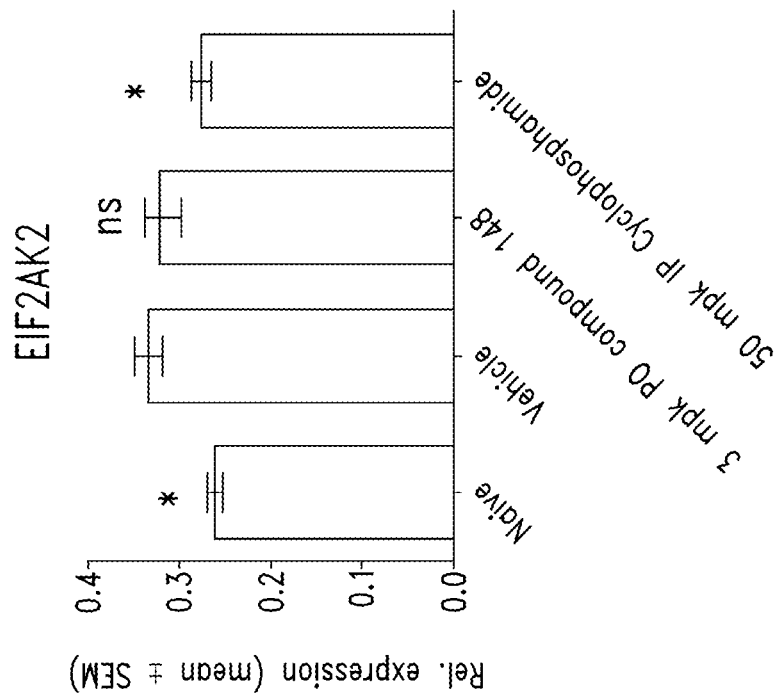
Figure 21A:
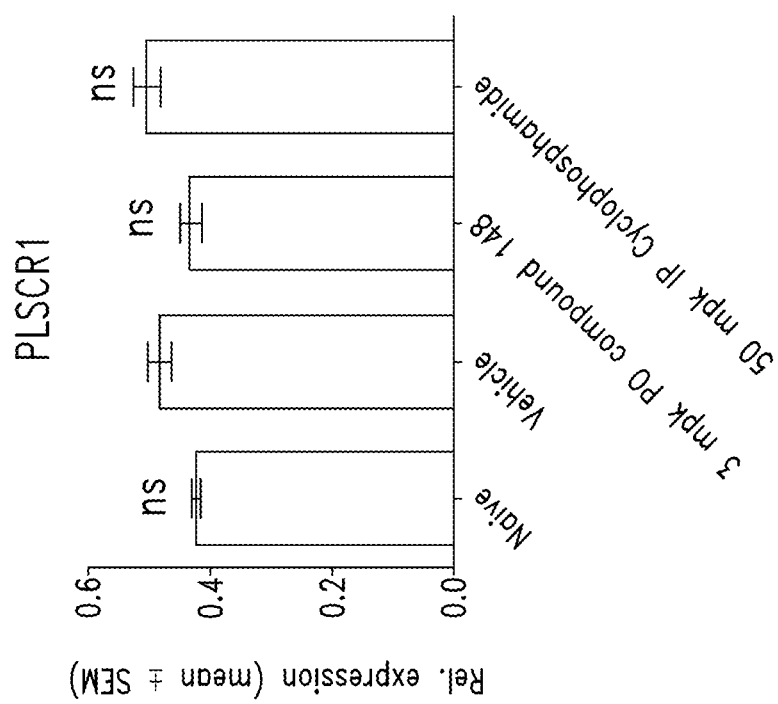
Figure 22B:
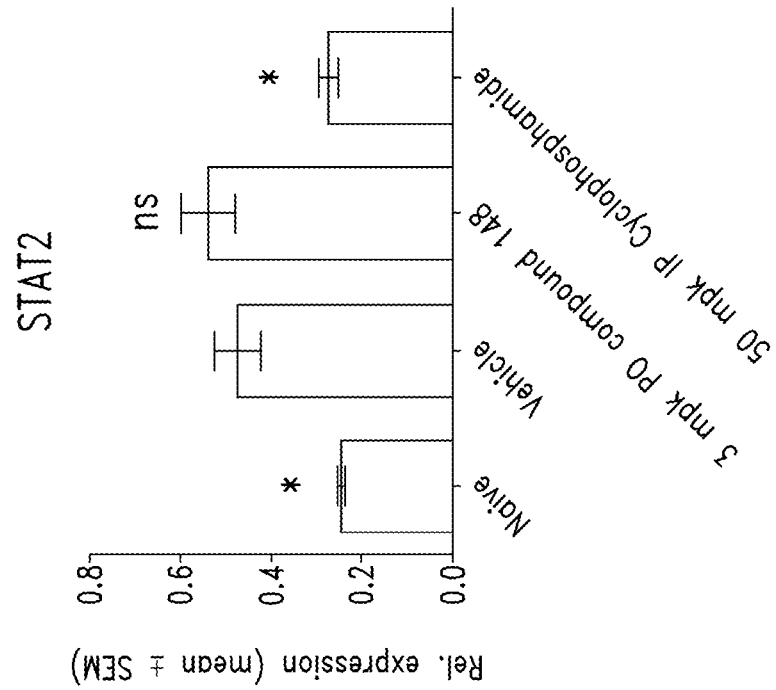
Figure 22A:
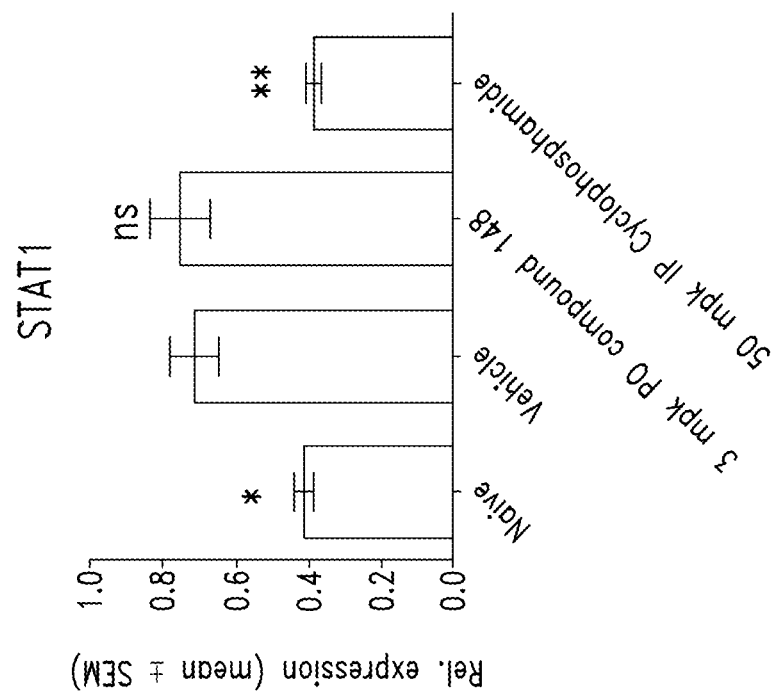
Figure 23B:
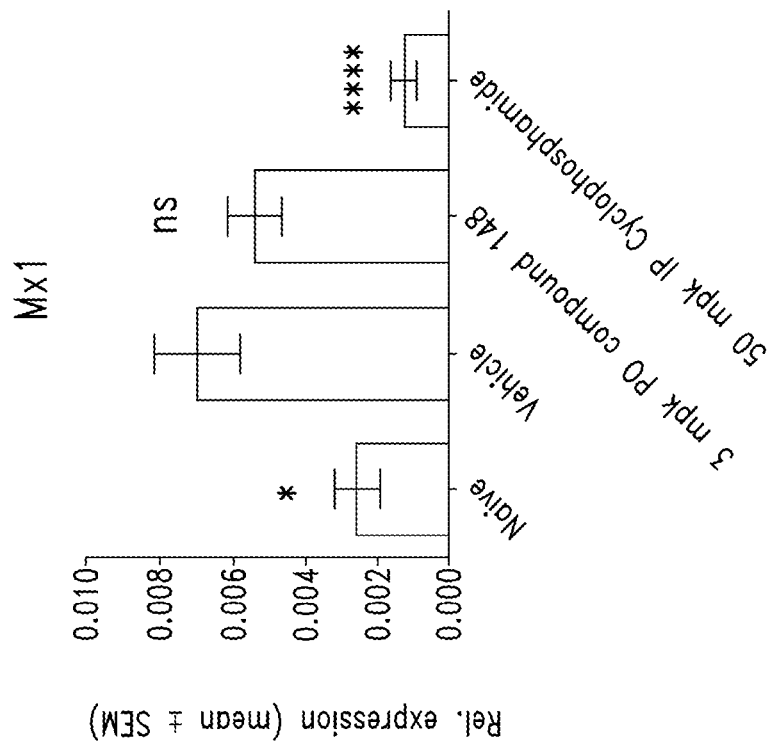
Figure 23A:
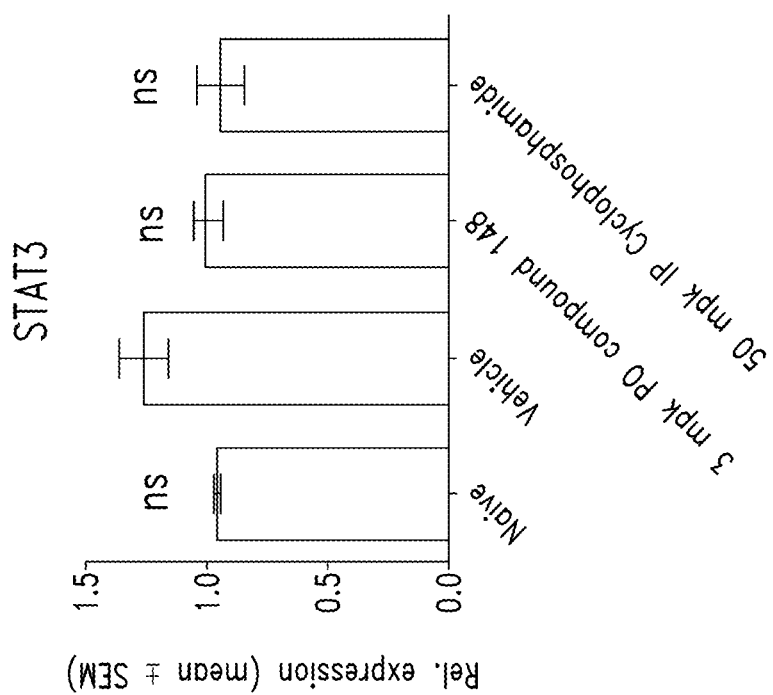
Figure 24:
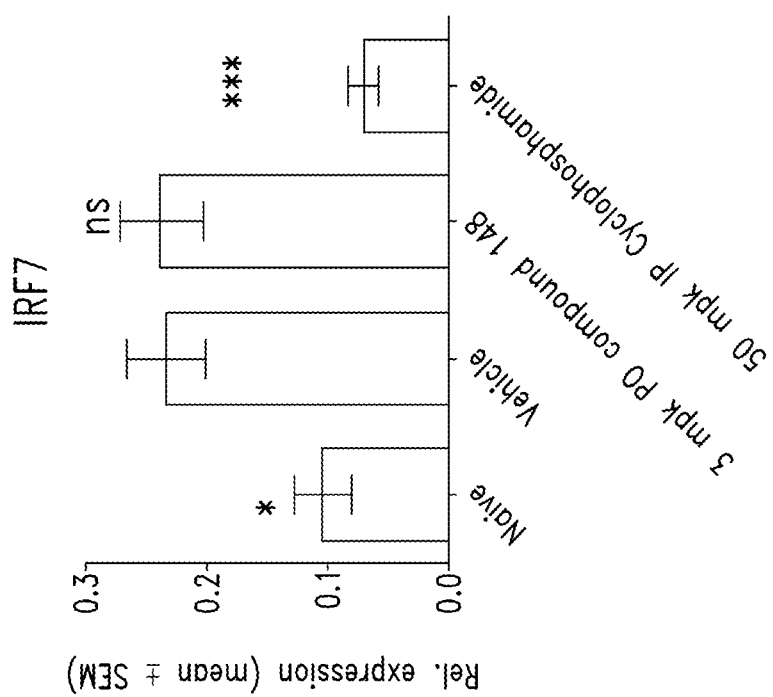
Figure 25B:
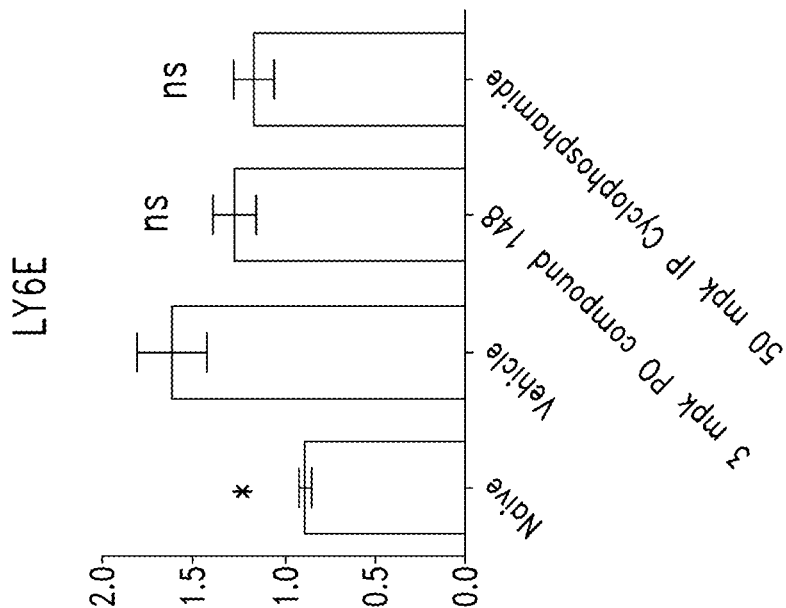
Figure 25A:
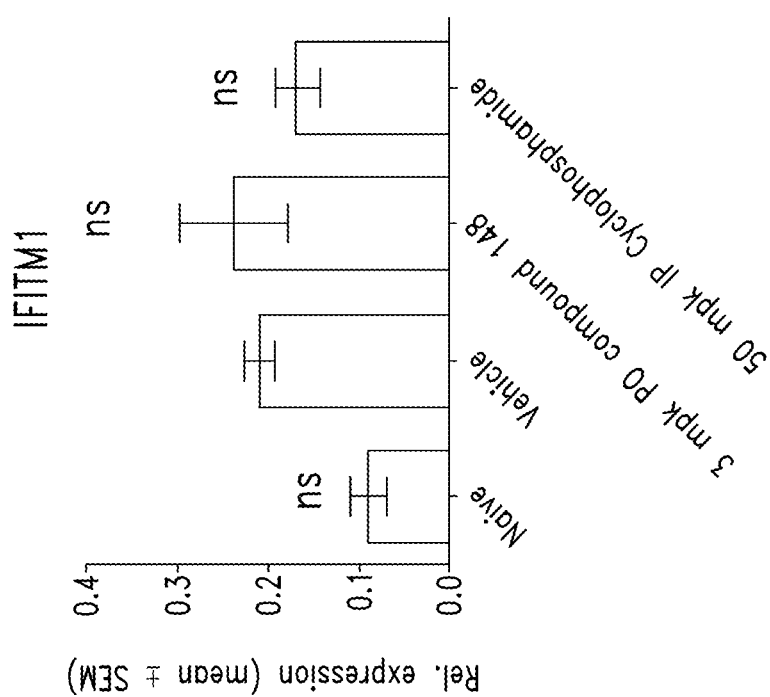
Figure 26B:
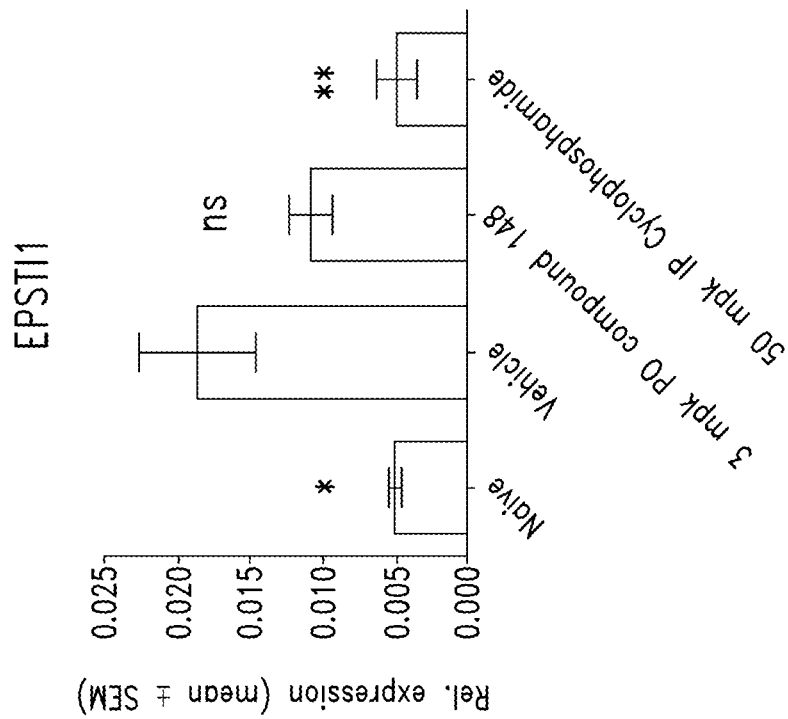
Figure 26A:
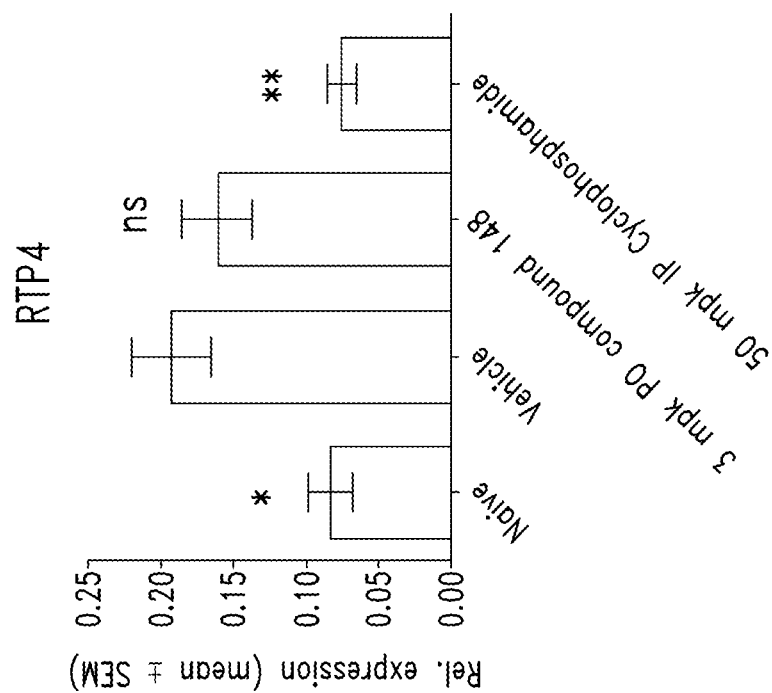
Figure 27B:
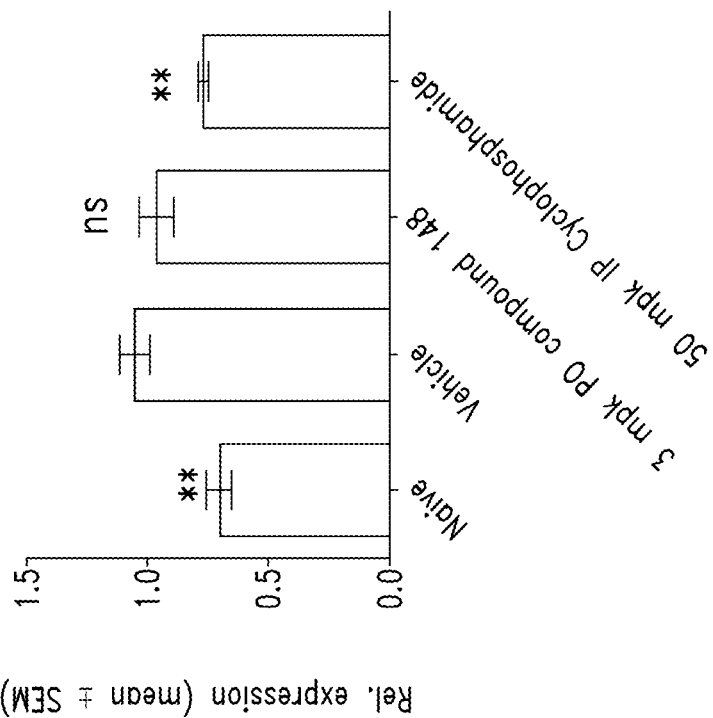
Figure 27A:
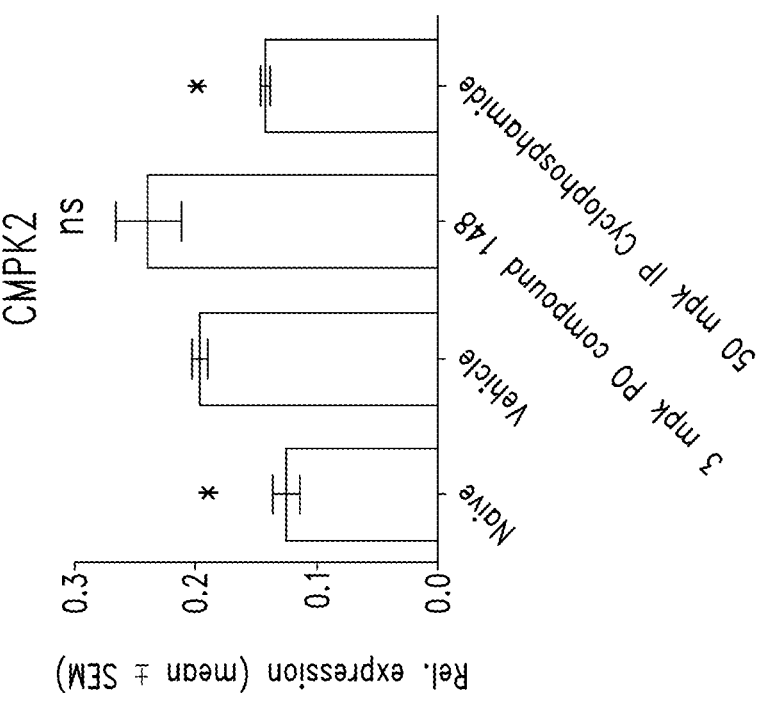
Figure 28:
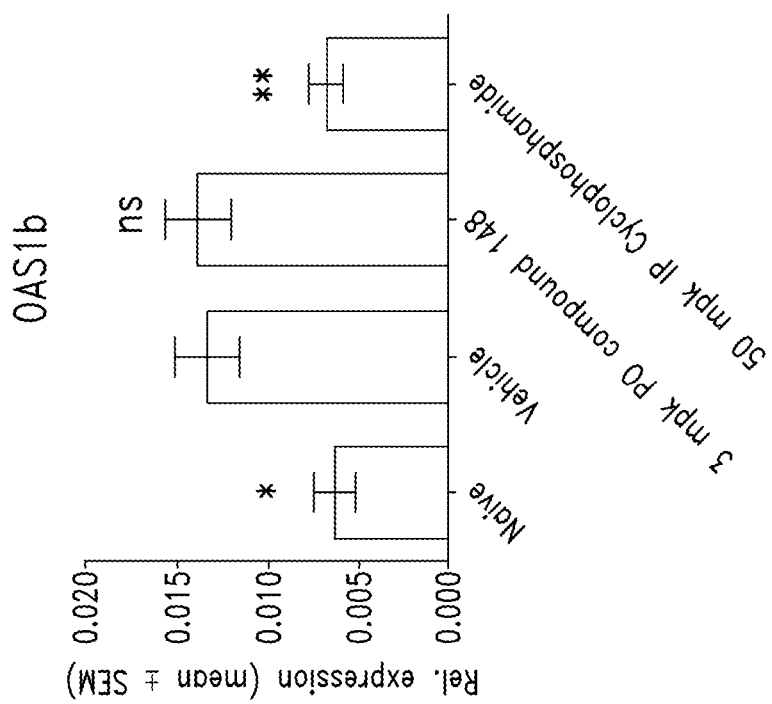
Figure 29B:
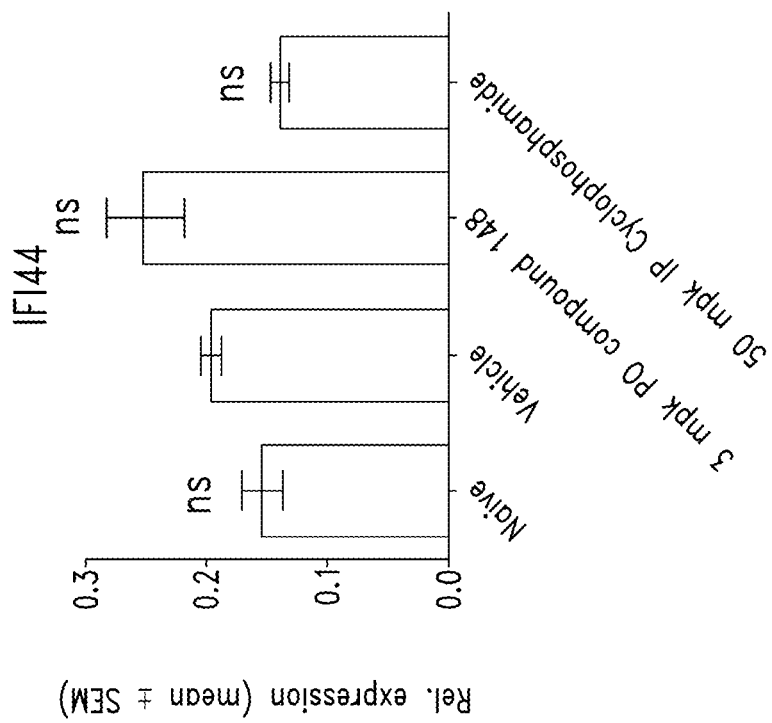
Figure 29A:
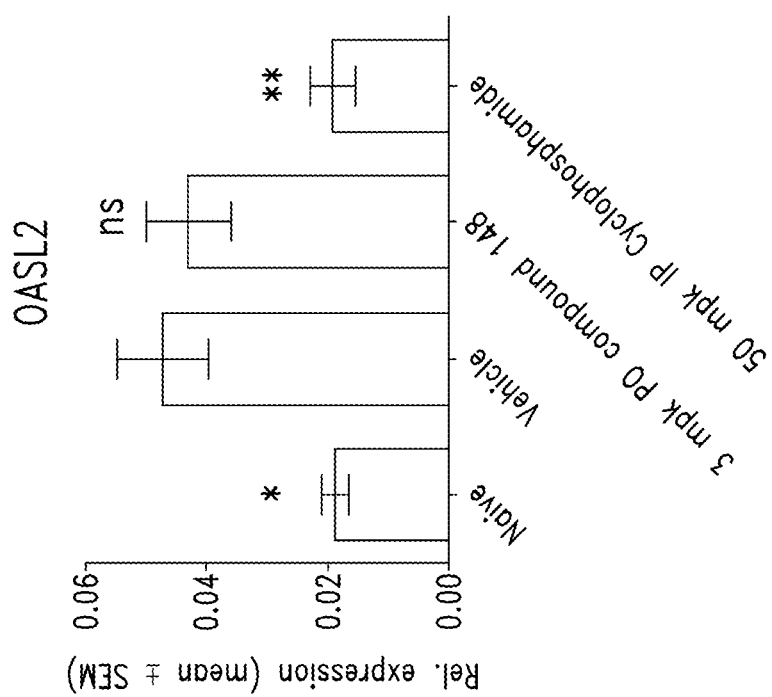
Figure 30B:
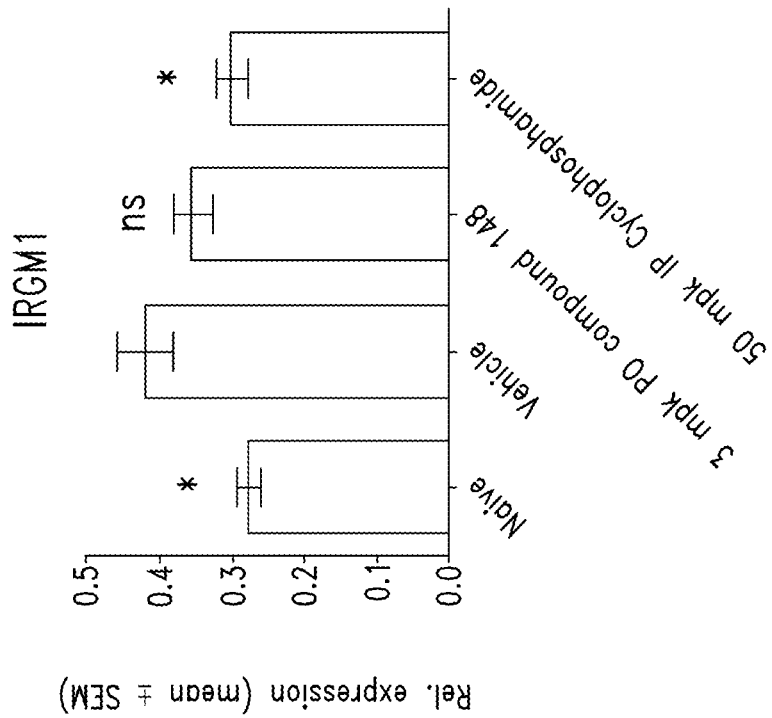
Figure 30A:
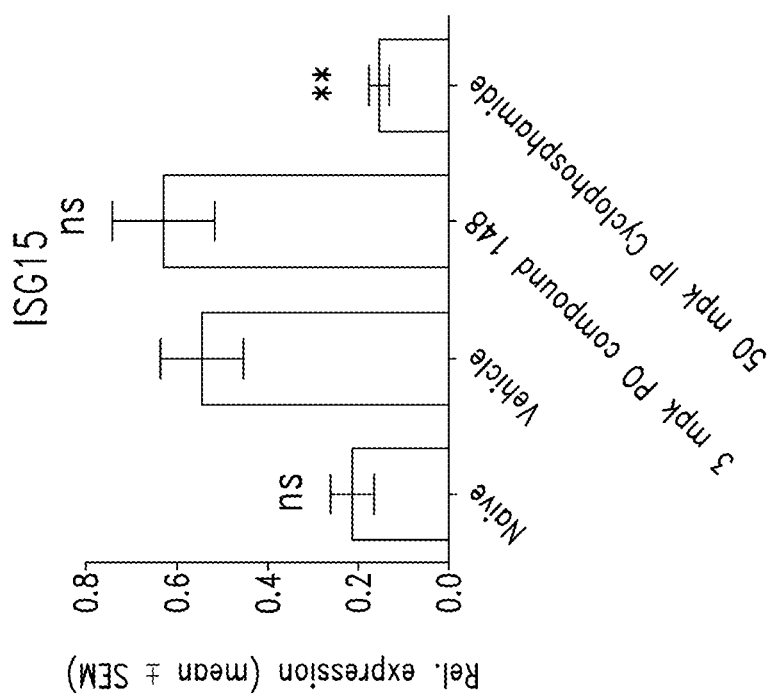
Figure 31B:
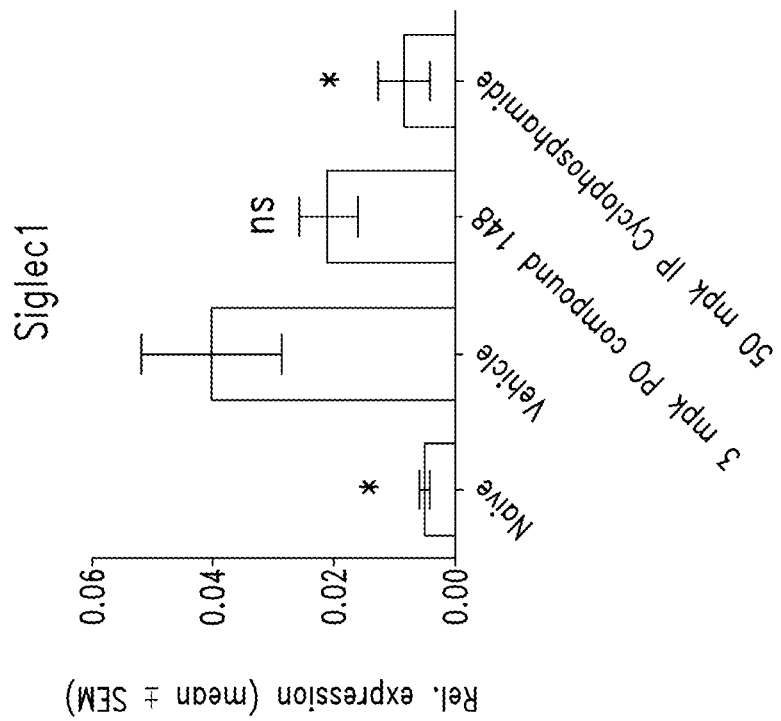
Figure 31A:
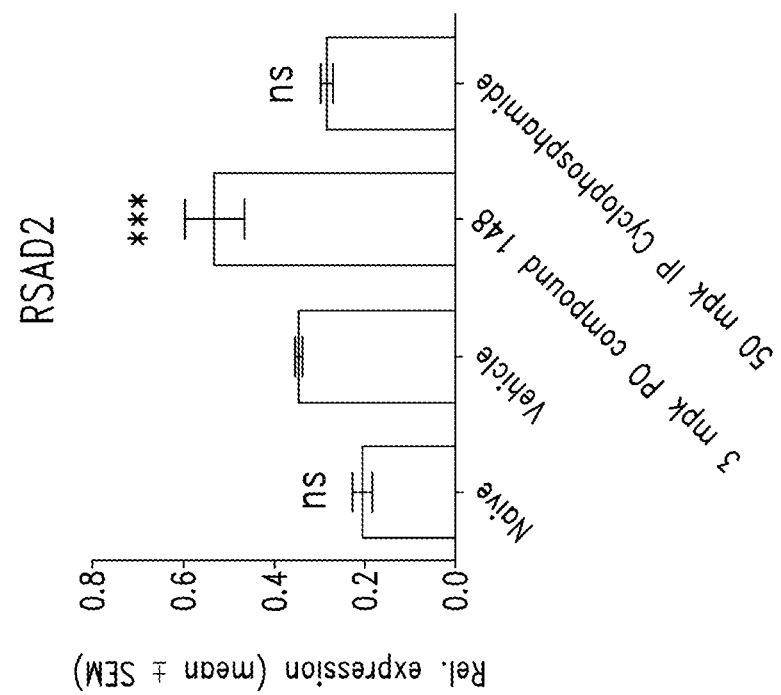
Figure 32:
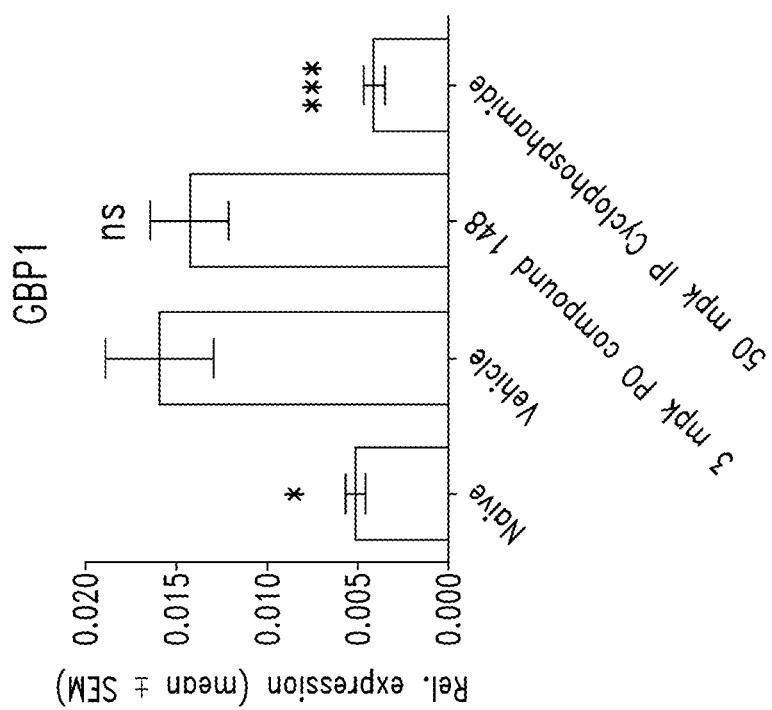
Figure 33:
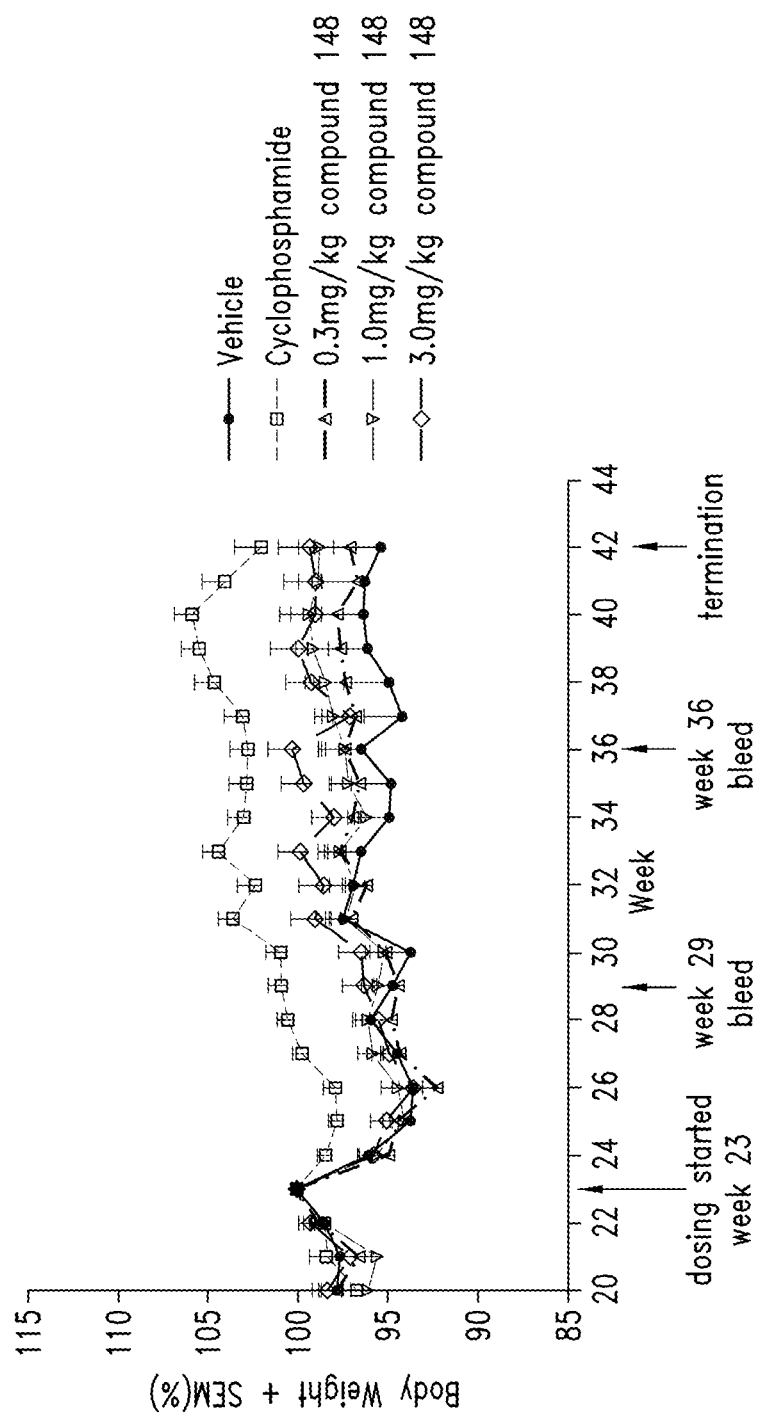
FIG. 33 shows mean body weights from the various treatment groups, taken over the course of the study.

As discussed above, IFNAR1 (Interferon alpha receptor 1) and its ligand IFNα are important modulators of lupus-associated autoimmune response in humans. Serum IFNα was measured by ELISA (eBioscience kit) at 23, 29, 36, and 42 weeks (FIG. 17). Assay sensitivity was 7.48 pg/ml (dotted line). All treatment groups receiving compound 148 showed lower serum IFNα levels compared to vehicle over the course of treatment. However, several samples at multiple time points were below the sensitivity of the assay (data not shown), consistent with reports that the NZBWF1 model has a weak IFNα signature. To determine whether compound 148 affected IFNAR1 expression, percent surface expression and MFI expression were measured in pDC cells at termination (FIGS. 18A and 18B, respectively). After five months of treatment, there was very little difference between the groups for either measurement.

Example 12

Expression of Genes Responsive to Type-1 Interferon Signaling

Expression profiles were also determined for a number of genes reported to be upregulated by type-1 interferon signaling (FIGS. 19A-32). While treatment with 3 mpk PO compound 148 slightly decreased mRNA expression levels of some IFN-inducible genes and increased expression of other genes, the majority of these changes did not reach statistical significance. Overall, treatment with compound 148 had no significant effect on the expression levels of IFN-inducible genes. However, these data are consistent with reports indicating that this mouse model has low endogenous IFNα expression (see, e.g., Mathian et al., *J. Immunol.* 174:5, 2499-2509 (2005) (adenoviral-mediated introduction of IFNα induces early lethal lupus in NZBWF1 mice). Thus, IFNα is likely not a disease driver in this mouse model.

Example 13

Synthesis of Compound 5

(R)-tert-butyl 2-(tert-butyldimethylsilyloxy)ethyl(4-cyano-2,3-dihydro-1H-inden-1-yl)-carbamate (INT-14)

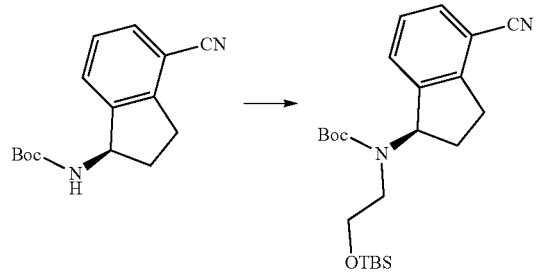 [SMILES: CC(C)(C)OC(=O)N[C@@H]1CCc2c(C#N)cccc21 ; CC(C)(C)OC(=O)N(CCO[Si](C)(C)C(C)(C)C)[C@@H]1CCc2c(C#N)cccc21]

To a flame-dried flask under $N_2$ was added (R)-tert-butyl 4-cyano-2,3-dihydro-1H-inden-1-ylcarbamate INT-8 (8.3 g, 32.1 mmol) in anhydrous DMF (240 mL). The reaction mixture was cooled to 0° C. and sodium hydride (3.8 g, 60% in oil, 160.6 mmol) was added portionwise. After stirring at 0° C. for 2.75 h, (2-bromoethoxy)(tert-butyl)dimethylsilane (16.9 mL, 70.7 mmol) was added. The ice bath was removed after 5 mins and the reaction mixture was allowed to warm to room temperature. After 1.5 h, the reaction mixture was quenched by the slow addition of sat. $NaHCO_3$ at 0° C. Once gas evolution was complete the reaction was extracted with EA. The organic layers were washed with water and brine, dried over $MgSO_4$ and concentrated. The product was purified by chromatography (EA/hexanes) to provide 10.76 g (80%) of (R)-tert-butyl 2-(tert-butyldimethylsilyloxy)ethyl (4-cyano-2,3-dihydro-1H-inden-1-yl)carbamate INT-14 as a colorless oil. LCMS-ESI (m/z) calculated for $C_{23}H_{36}N_2O_3Si$: 416.6; found 317.2 [M-Boc]$^+$ and 439.0 [M+Na]$^+$, $t_R$=4.04 min (Method 1). $^1$H NMR (400 MHz, $CDCl_3$) δ 7.46 (d, J=7.6, 1H), 7.38-7.32 (m, 1H), 7.33-7.18 (m, 1H), 5.69 (s, 0.5H), 5.19 (s, 0.5H), 3.70 (ddd, J=48.8, 26.6, 22.9, 1.5H), 3.50-3.37 (m, 1H), 3.17 (ddd, J=16.7, 9.4, 2.2, 2H), 2.93 (m, 1.5H), 2.45 (s, 1H), 2.21 (dd, J=24.5, 14.5, 1H), 1.56-1.37 (bs, 4.5H), 1.22 (bs, 4.5H), 0.87-0.74 (m, 9H), −0.04 (dd, J=26.6, 8.2, 6H). $^{13}$C NMR (101 MHz, $CDCl_3$) δ 155.03, 146.55, 145.54, 131.16, 130.76, [128.11, 127.03], 117.58, 109.20, 79.88, [63.93, 61.88], [61.44, 60.34], [49.73, 46.76], 30.30, 29.70, 28.44, 28.12, [25.87, 25.62], −5.43. (S)-tert-butyl 2-(tert-butyldimethylsilyloxy)ethyl(4-cyano-2,3-dihydro-1H-inden-1-yl)carbamate INT-15 is prepared in an analogous fashion using INT-9.

(R)-tert-butyl 2-(tert-butyldimethylsilyloxy)ethyl (4-(N-hydroxycarbamimidoyl)-2,3-dihydro-1H-inden-1-yl)carbamate (INT-16)

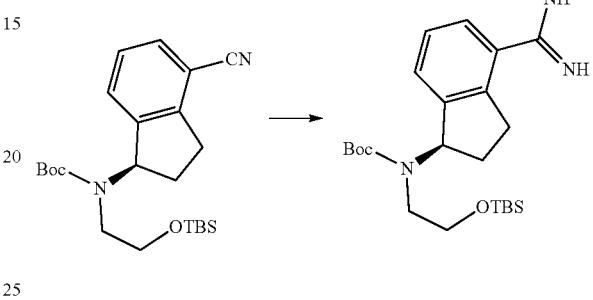

Prepared using General Procedure 3. To a solution of (R)-tert-butyl 2-(tert-butyldimethylsilyloxy)ethyl(4-cyano-2,3-dihydro-H-inden-1-yl)carbamate INT-14 (12.0 g, 28.9 mmol) in EtOH (120 mL), under an atmosphere of $N_2$ was added hydroxylamine-HCl (6.0 g, 86.5 mmol) and triethylamine (13.4 mL, 9.7 g, 86.5 mmol). The reaction mixture was refluxed at 80° C. for 4 h. The reaction mixture was cooled to room temperature and concentrated to dryness and then diluted with DCM (500 mL). The organic layer was washed with $NaHCO_3$, water, and brine. The combined organic layers were dried over $MgSO_4$ and concentrated to produce 11.8 g of (R)-tert-butyl 2-(tert-butyldimethylsilyloxy) ethyl (4-(N-hydroxycarbamimidoyl)-2,3-dihydro-1H-inden-1-yl)carbamate INT-16 as a white foamy solid, which was used without purification in the next experiment. LCMS-ESI (m/z) calculated for $C_{23}H_{39}N_3O_4Si$: 449.7; found 350.2 [M-Boc]$^+$ and 472.2 [M+Na]$^+$, $t_R$=1.79 min (Method 1). $^1$H NMR (400 MHz, CDCl3) δ 7.32 (t, J=7.3 Hz, 1H), 7.21-7.07 (m, 2H), 5.69 (s, 0.5H), 5.19 (s, 0.5H), 4.89 (s, 2H), 3.85-3.50 (m, 2H), 3.31 (ddd, J=12.2, 9.2, 2.5 Hz, 2H), 3.28-3.03 (m, 2H), 3.03-2.70 (m, 1H), 2.29 (t, J=23.6 Hz, 1H), 1.43 (bs, 4.5H), 1.28 (bs, 4.5H), 1.16-1.04 (m, 1H), 0.90-0.71 (m, 9H), 0.08-0.14 (m, 6H). $^{13}$C NMR (101 MHz, $CDCl_3$) δ 170.99, [156.20, 155.62], 152.38, [144.53, 143.57], [141.82, 141.21], 129.61, 126.78, [126.59, 126.25], [125.02, 124.77], [79.91, 79.68], 64.04, 61.88, [61.57, 61.23], [46.03, 45.76], 30.76, 30.21, [28.53, 28.28], 25.95, [25.66, 25.29], 25.13, [18.28, 17.94], 3.72, −5.34. (S)-tert-butyl 2-(tert-butyldimethylsilyloxy)ethyl (4-(N-hydroxycarbamimidoyl)-2,3-dihydro-1H-inden-1-yl)carbamate INT-17 is prepared in an analogous fashion using INT-15.

(R)-tert-butyl 2-(tert-butyldimethylsilyloxy)ethyl(4-(5-(3-cyano-4-isopropoxyphenyl)-1,2,4-oxadiazol-3-yl)-2,3-dihydro-1H-inden-1-yl)carbamate and (R)-tert-butyl 4-(5-(3-cyano-4-isopropoxyphenyl)-1,2,4-oxadiazol-3-yl)-2,3-dihydro-1H-inden-1-yl) (2-hydroxethyl) carbamate

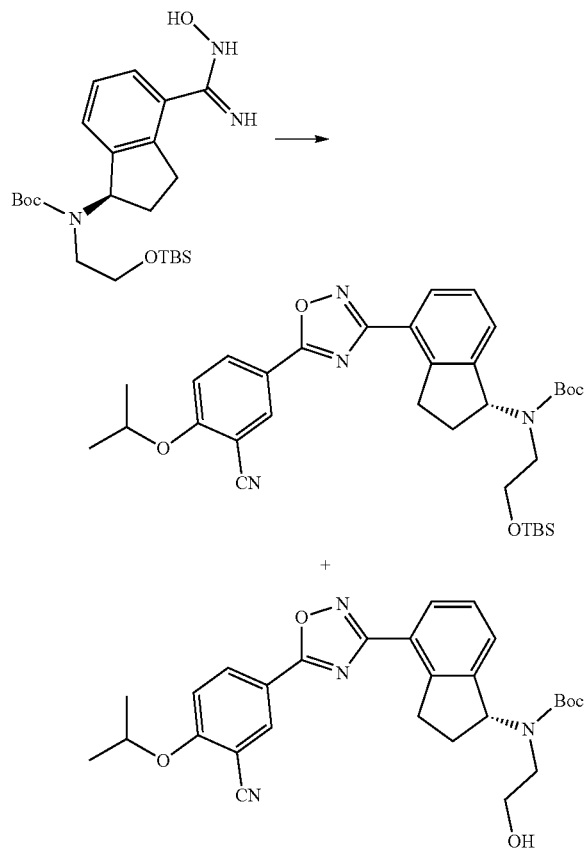

Prepared using General Procedure 4. To a solution of 3-cyano-4-isopropoxybenzoic acid (4.5 g, 21.9 mmol) in anhydrous DMF (100 mL) was added HOBt (5.4 g, 40.0 mmol) and EDC (5.6 g, 29.6 mmol). After 1 h, (R)-tert-butyl 2-(tert-butyldimethylsilyloxy)ethyl (4-(N-hydroxycarbamimidoyl)-2,3-dihydro-1H-inden-1-yl)carbamate INT-16 (11.8 g, 26.3 mmol) was added and the reaction mixture was stirred at room temperature for 2 h. LCMS analysis showed complete conversion to the intermediate, (R)-tert-butyl 2-(tert-butyldimethylsilyloxy) ethyl (4-(N-(3-cyano-4-isopropoxybenzoyloxy) carbamimidoyl)-2,3-dihydro-1H-inden-1-yl)carbamate INT-18. The reaction mixture was then heated to 80° C. for 12 h. The reaction mixture was cooled to room temperature and diluted with EA (250 mL). NaHCO₃ (250 mL) and water (350 mL) were added until all the solids dissolved. The mixture was extracted with EA and the organic layers washed successively with water and brine. The organic layers were dried over MgSO₄ and concentrated to produce 15.3 g of a mixture of (R)-tert-butyl 2-(tert-butyldimethylsilyloxy)ethyl(4-(5-(3-cyano-4-isopropoxyphenyl)-1,2,4-oxadiazol-3-yl)-2,3-dihydro-1H-inden-1-yl) carbamate INT-19, and the corresponding material without the TBS protecting group, (R)-tert-butyl 4-(5-(3-cyano-4-isopropoxyphenyl)-1,2,4-oxadiazol-3-yl)-2,3-dihydro-1H-inden-1-yl) (2-hydroxyethyl) carbamate INT-20. The mixture was a brown oil, which could be used directly without further purification or purified by chromatography (EA/hexane). INT-19: LCMS-ESI (m/z) calculated for $C_{34}H_{46}N_4O_5Si$: 618.8; found 519.2 [M-Boc]⁺ and 641.3 [M+Na]⁺, $t_R$=7.30 min (Method 1). ¹H NMR (400 MHz, CDCl₃) δ 8.43 (d, J=2.1, 1H), 8.34 (dd, J=8.9, 2.2, 1H), 8.07 (d, J=8.1, 1H), 7.46-7.26 (m, 2H), 7.12 (d, J=9.0, 1H), 5.85 (s, 0.5H), 5.37 (s, 0.5H), 4.80 (dt, J=12.2, 6.1, 1H), 3.92-3.32 (m, 3.5H), 3.17 (s, 2H), 2.95 (s, 0.5H), 2.62-2.39 (m, 1H), 2.38-2.05 (m, 1H), 1.53 (s, 4.5H), 1.48 (d, J=6.1, 6H), 1.33-1.27 (m, 4.5H), 0.94-0.77 (m, 9H), 0.01 (d, J=20.9, 6H). ¹³C NMR (101 MHz, DMSO) δ 173.02, 169.00, 162.75, [156.22, 155.52], [145.18, 144.12], [143.39, 142.76], 134.16, 133.89, 128.20, [128.01, 127.85], [127.04, 126.90], 126.43, 123.31, 116.93, 115.30, 113.55, 103.96, [79.95, 79.68], 72.73, 67.61, 63.42, [61.91, 61.77], 60.99, 46.11, 31.78, [30.47, 29.87], [28.55, 28.26], 25.93, 21.75, 18.30, 0.00, -5.37. INT-20: LCMS-ESI calculated for $C_{28}H_{32}N_4O_5$: 504.6; found 527.2 [M+Na]⁺, $t_R$=2.65 min (Method 1). ¹H NMR (400 MHz, CDCl₃) δ 8.36 (d, J=2.1, 1H), 8.27 (dd, J=8.9, 2.2, 1H), 8.03 (d, J=7.2, 1H), 7.35-7.26 (m, 2H), 7.06 (d, J=9.0, 1H), 5.44 (s, 1H), 4.73 (dt, J=12.2, 6.1, 1H), 3.64 (s, 2H), 3.44 (ddd, J=17.5, 9.5, 3.2, 2H), 3.11 (dt, J=17.4, 8.6, 3H), 2.54-2.38 (m, 1H), 2.04 (td, J=17.6, 8.8, 1H), 1.50-1.24 (m, 15H). (S)-tert-butyl 2-(tert-butyldimethylsilyloxy)ethyl(4-(5-(3-cyano-4-isopropoxyphenyl)-1,2,4-oxadiazol-3-yl)-2,3-dihydro-1H-inden-1-yl)carbamate INT-21 and (S)-tert-butyl 4-(5-(3-cyano-4-isopropoxyphenyl)-1,2,4-oxadiazol-3-yl)-2,3-dihydro-1H-inden-1-yl) (2-hydroxyethyl) carbamate INT-22 were made in an analogous fashion.

(R)-5-(3-(1-(2-hydroxyethylamino)-2,3-dihydro-1H-inden-4-yl)-1,2,4-oxadiazol-5-yl)-2-isopropoxybenzonitrile (Compound 2)

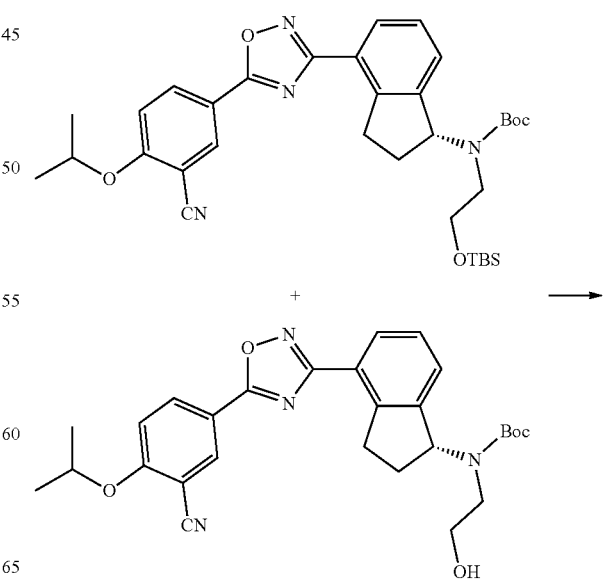

-continued

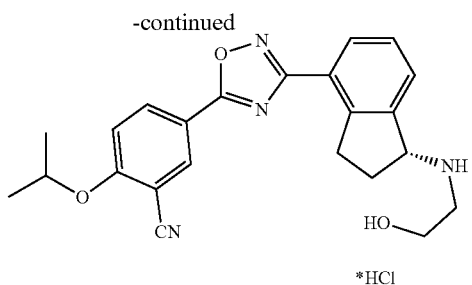

*HCl

To a solution of (R)-tert-butyl 2-(tert-butyldimethylsilyloxy)ethyl(4-(5-(3-cyano-4-isopropoxyphenyl)-1,2,4-oxadiazol-3-yl)-2,3-dihydro-1H-inden-1-yl)carbamate INT-19 and (R)-tert-butyl 4-(5-(3-cyano-4-isopropoxyphenyl)-1,2,4-oxadiazol-3-yl)-2,3-dihydro-1H-inden-1-yl) (2-hydroxethyl) carbamate INT-20 (13.9 g, 27.5 mmol) in dioxane (70 mL) at 0° C. was added 4N HCl in dioxane (68.8 g, 275.4 mmol). The reaction mixture was warmed to room temperature and then heated to 50° C. for 1 h. The resulting suspension was cooled to room temperature and $Et_2O$ (75 mL) was added. The precipitate was collected by filtration, washed with $Et_2O$ and dried to produce 10.5 g of an off-white solid. The HCl salt was recrystallized from MeOH (165 mL) to produce 5.98 g (56% overall yield from (R)-tert-butyl 2-(tert-butyldimethylsilyloxy)ethyl(4-cyano-2,3-dihydro-1H-inden-1-yl) carbamate) of (R)-5-(3-(1-(2-hydroxyethylamino)-2,3-dihydro-1H-inden-4-yl)-1,2,4-oxadiazol-5-yl)-2-isopropoxybenzonitrile 2 as a white solid. LCMS-ESI (m/z) calculated for $C_{23}H_{24}N_4O_3$: 404.5; found 405.4 [M+H]$^+$, $t_R$=2.44 min. $^1$H NMR (400 MHz, DMSO) δ 9.25 (s, 2H), 8.53 (d, J=2.3, 1H), 8.42 (dd, J=9.0, 2.3, 1H), 8.17 (d, J=7.7, 1H), 7.97 (d, J=7.6, 1H), 7.63-7.50 (m, 2H), 5.28 (t, J=5.0, 1H), 4.99 (hept, J=6.1, 1H), 4.92 (s, 1H), 3.72 (q, J=5.2, 2H), 3.57-3.43 (m, 1H), 3.27 (ddd, J=17.6, 9.1, 5.0, 1H), 3.15-2.85 (m, J=24.2, 2H), 2.53 (dtd, J=9.0, 5.5, 5.3, 3.6, 1H), 2.30 (ddd, J=13.4, 8.9, 4.6, 1H), 1.39 (d, J=6.0, 6H). $^{13}$C NMR (101 MHz, DMSO) δ 173.25, 167.86, 162.47, 144.56, 139.13, 134.53, 133.77, 129.30, 128.93, 127.45, 122.83, 115.79, 115.15, 114.84, 102.40, 72.46, 61.04, 56.51, 46.38, 31.53, 27.74, 21.37. Elemental analysis for $C_{23}H_{25}N_4O_3Cl$: C calc.=62.65%; found=62.73%; H calc.=5.71%; found=5.60%; N calc.=12.71%; found=12.64%; Cl calc.=8.04%; found=8.16%. Chiral HPLC of the free base: (R)-5-(3-(1-(2-hydroxyethylamino)-2,3-dihydro-1H-inden-4-yl)-1,2,4-oxadiazol-5-yl)-2-isopropoxy-benzo-nitrile was eluted using 10% i-PrOH in hexanes plus 0.3% DEA: >99.9% ee, $t_R$=37.72 min. (S)-5-(3-(1-(2-hydroxyethylamino)-2,3-dihydro-1H-inden-4-yl)-1,2,4-oxadiazol-5-yl)-2-isopropoxy benzonitrile (compound 5) was obtained in analogous fashion from (S)-tert-butyl 2-(tert-butyldimethyl silyloxy)ethyl(4-(5-(3-cyano-4-isopropoxyphenyl)-1,2,4-oxadiazol-3-yl)-2, 3-dihydro-1H-inden-1-yl)carbamate INT-21 and (S)-tert-butyl 4-(5-(3-cyano-4-isopropoxyphenyl)-1,2,4-oxadiazol-3-yl)-2,3-dihydro-1H-inden-1-yl) (2-hydroxyethyl) carbamate INT-22: >99.9% ee, $t_R$ for (S)-enantiomer=35.86 min.

Example 14

Treatment of SLE in a Murine Model

As in Example 2, compound 5 was tested for efficacy in the same NZBxNZW F1 ("NZBWF1") mouse model for SLE as compound 148. Six groups of NZBWF1 mice (Jackson Laboratories, stock #100008) were used in the study and were acclimated to the research facility for 6 weeks prior to the start of the study. Weekly measurements of proteinuria (excess serum proteins present in the urine) and body weight began at 20 weeks of age. At 22 weeks of age, the mice were assigned to groups in a balanced manner in order to achieve average body weight and average proteinuria measurements across the groups. One "naive" group consisting of 10 mice was euthanized at the start of treatment and used as a source of tissue for analysis. Treatment began at 22 weeks of age.

Figure 39:
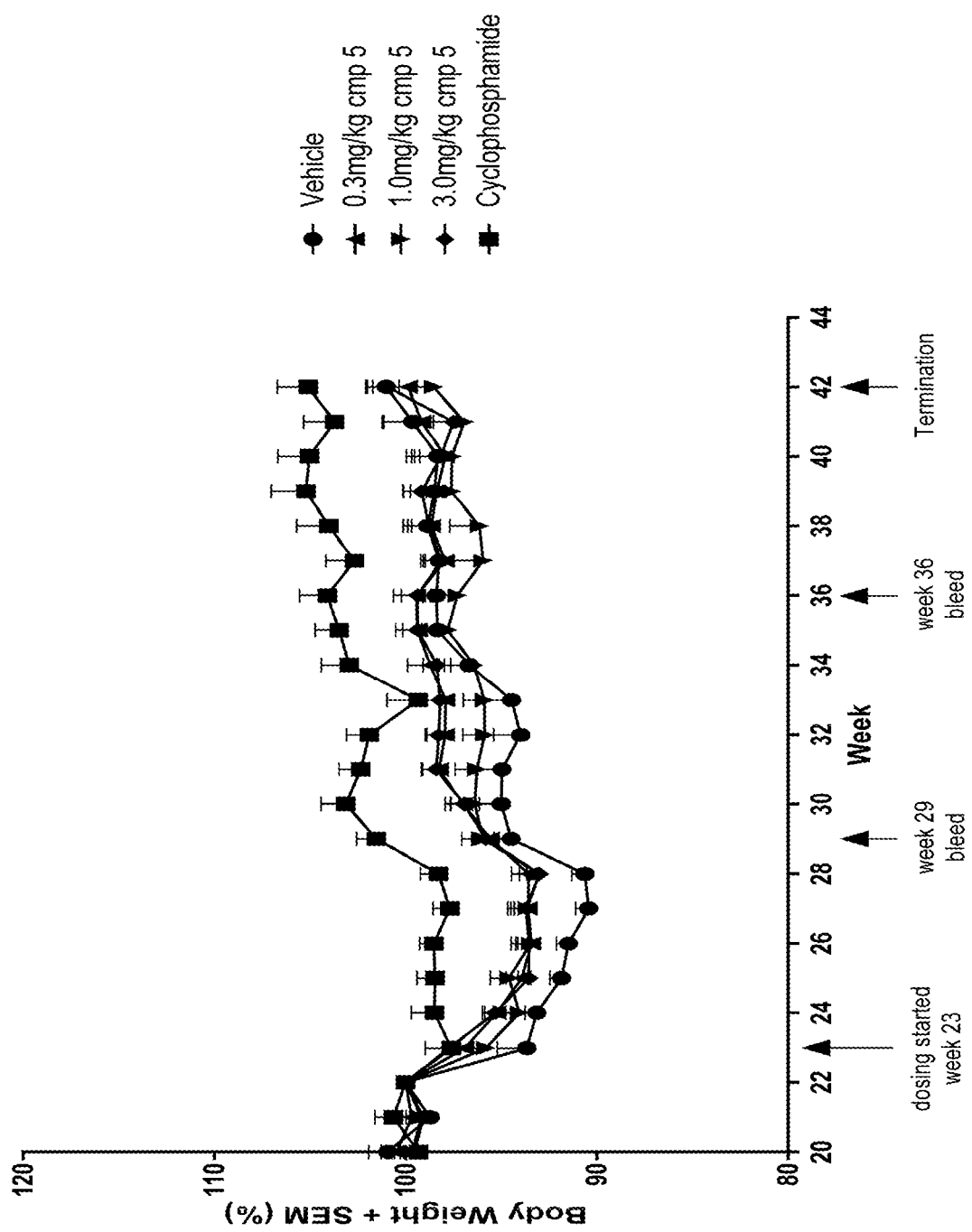
FIG. 39 shows mean body weights from the various treatment groups, taken over the course of the study.
Figure 40A:
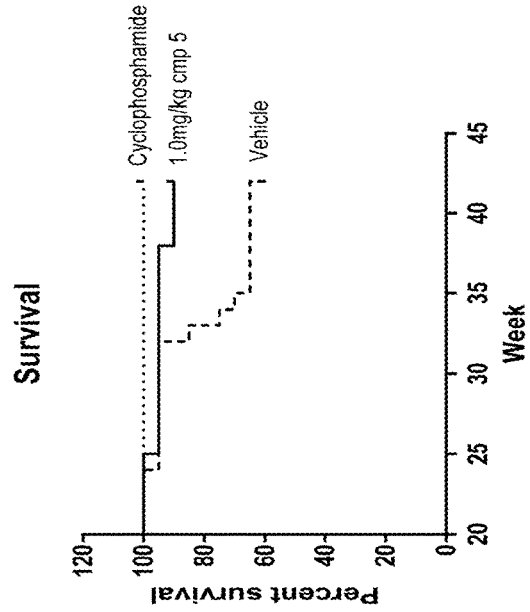
FIGS. 40A-C shows survival rates of mice from the various treatment groups, taken over the course of the study.
Figure 40B:
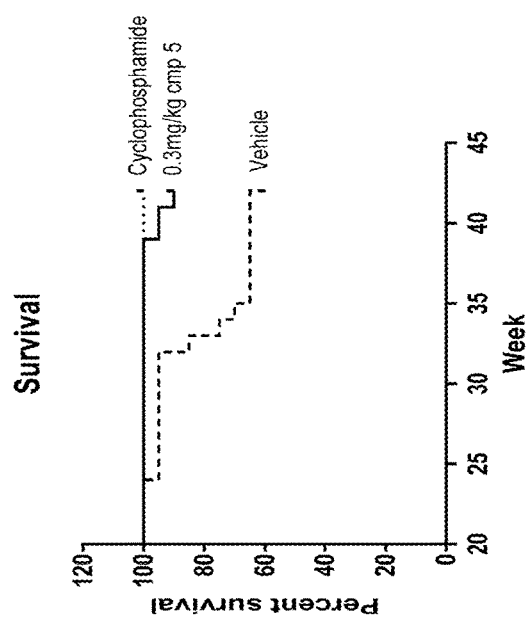
Figure 40C:
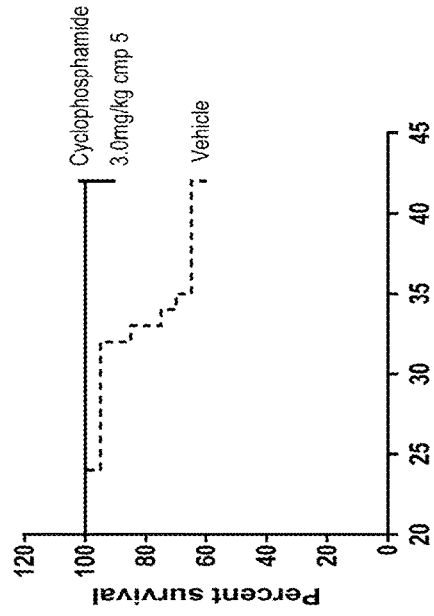

The five treatment groups were administered cyclophosphamide (positive control, 20 mice; introduced gradually to reduce toxicity (IP, once a week, 10 mg/kg at Weeks 22 and 23 and 50 mg/kg from Week 24 to the end of the study)), vehicle (negative control, 20 mice), or compound 5 (three groups of 20 mice), beginning at 22 weeks of age and observed over the course of 20 weeks. The three groups dosed with compound 5 received 0.3, 1.0, and 3.0 mg/kg PO QD, respectively (20 mice per dosage). Surviving animals were sacrificed at 42 weeks. Treatment with cyclophosphamide increased body weights while vehicle- and treatment with compound 5-treated mice had similar body weights and minimal overall weight loss. See FIG. 39. Treatment with cyclophosphamide and treatment with compound 5 both improved survival compared to vehicle treated animals (Logrank: 0.3 mg/kg: p=0.0229. 1.0 mg/kg: p=0.0308. 3.0 mg/kg: p=0.0201. Cyclophosphamide: p=0.0017). See FIGS. 40A-C. Disease development was evaluated as disclosed in the following examples.

Example 15

Reduction of Proteinuria Scores

Figure 41B:
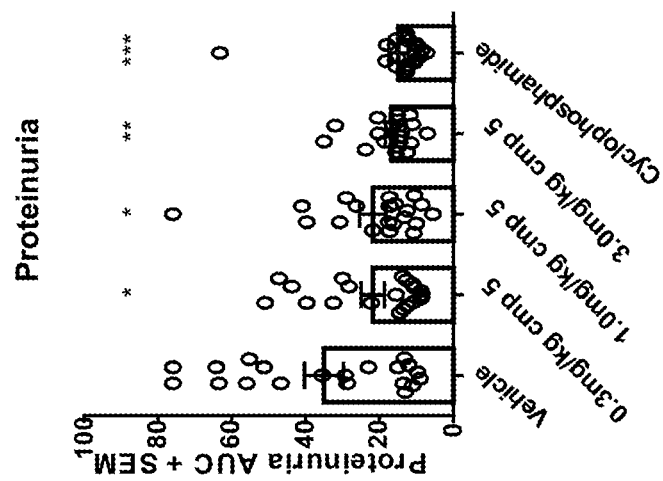
FIG. 41B shows mice receiving test compound demonstrated lower proteinuria scores in a dose-dependent fashion.
Figure 41A:
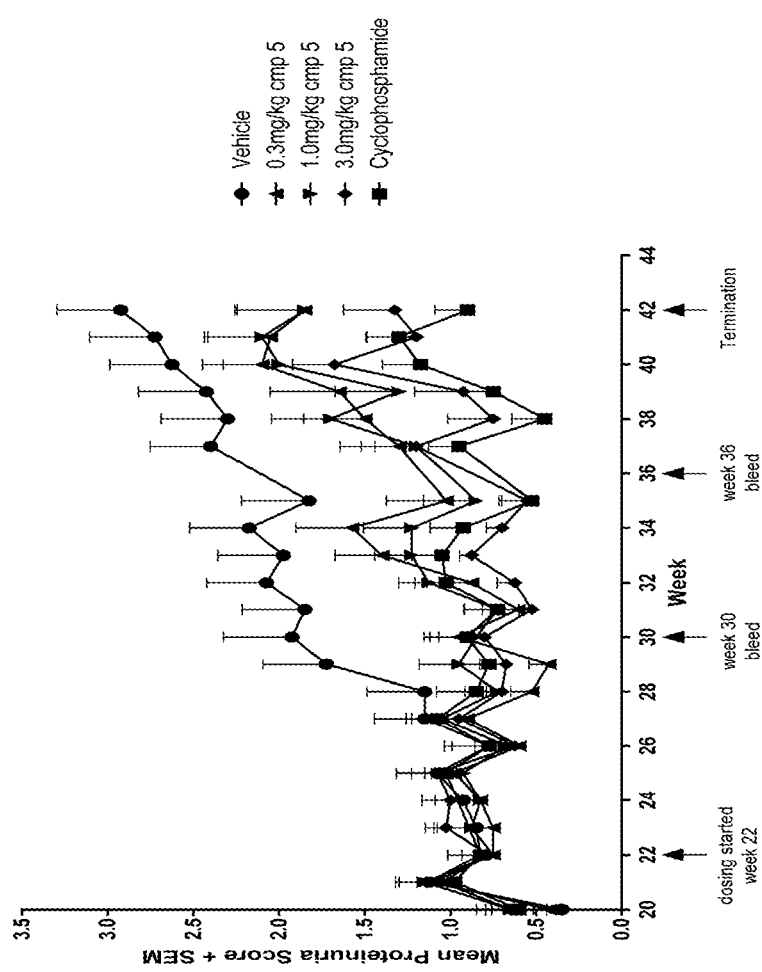

As in Example 3, proteinuria was measured weekly beginning at 20 weeks using urine dip sticks (Roche Diagnostics Chemstrip 2GP, cat. no. 11895397160, per manufacturer's protocol). Proteinuria was expressed as a score from 0 to 4 (0=no protein; 1=traces of protein (<30 mg/dL); 2=30-100 mg/dL; 3=100-500 mg/dL; 4=>500 mg/dL). Mean proteinuria scores over the course of the study are shown in FIG. 41A. As expected, mice treated with the vehicle developed proteinuria compared to the naïve group at the onset of treatment. Mice receiving compound 5 demonstrated lower proteinuria scores in a dose-dependent fashion compared to vehicle mice, and both the group receiving 3.0 mg/kg compound 5 and the group receiving cyclophosphamide showed significant improvement relative to vehicle. See FIG. 41B. (In this and the following experiments, the number of mice per group was approximately 20, and statistics were determined by one-way ANOVA with Dunnett's comparison.)

Example 16

Serum BUN Levels

Figure 42:
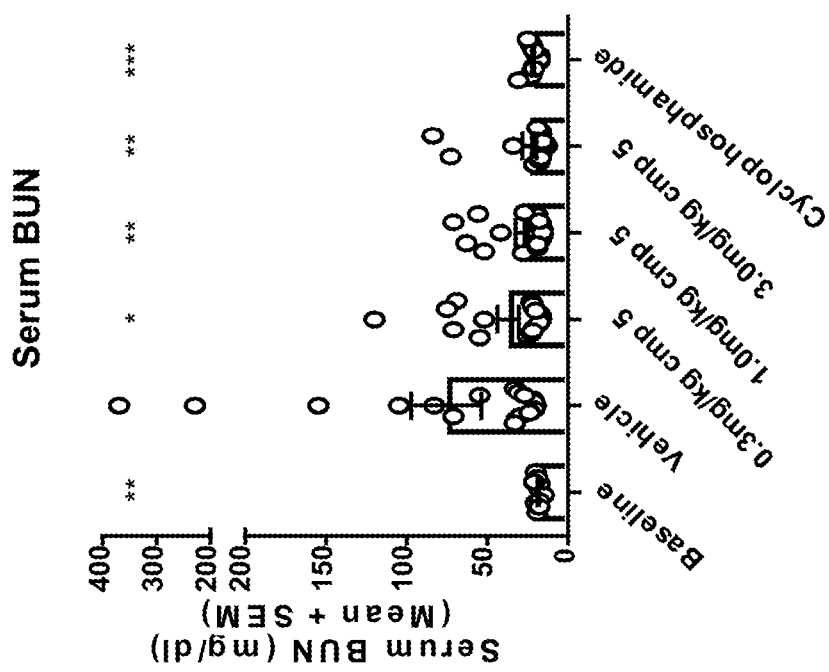
FIG. 42 shows increased levels of serum blood urea nitrogen (BUN) in vehicle treated mice, with a significant reduction in serum BUN for mice treatment with the test compound.

As in Example 4, serum blood urea nitrogen (BUN) was measured at termination to assess kidney function. As shown in FIG. 42, serum BUN was elevated in vehicle treated mice relative to expected serum levels (normal BUN range=8-33 mg/dl), and was decreased in all other treated groups. A significant reduction in serum BUN was observed for treatment with compound 5 at all doses or with cyclophosphamide.

Example 17

Figure 43:
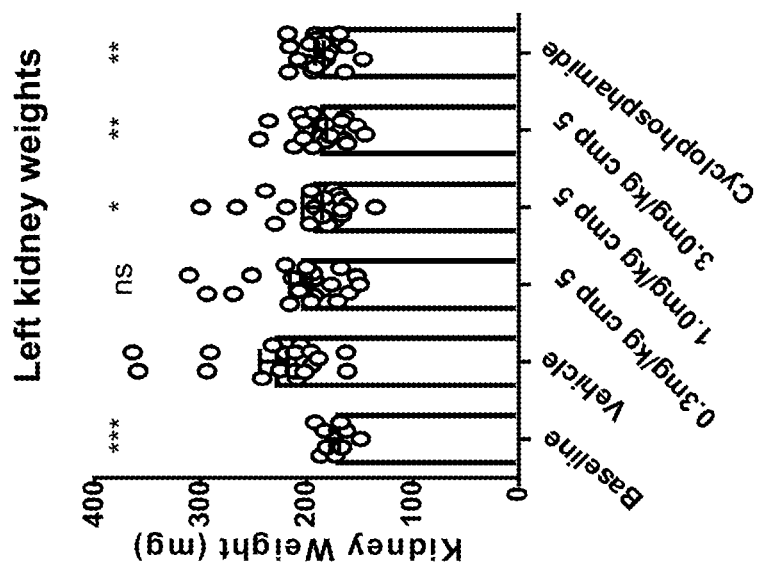
FIG. 43 shows left kidney weights for the various treatment groups at termination of the study (42 weeks).
Figures 44A, 44B:
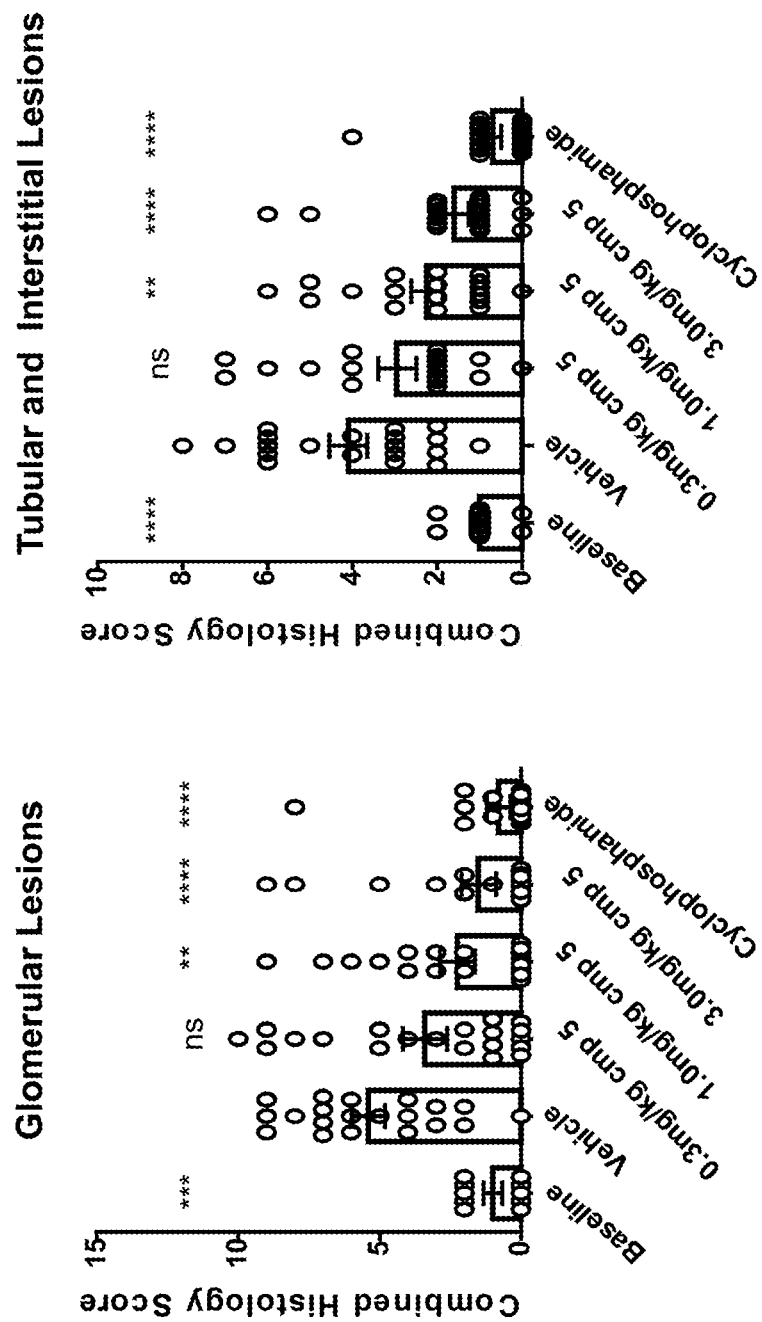

Reduction of Kidney Weight, Tertiary Lymphatic Tissue, and Nephritic Lesions As in Example 5, left kidneys were weighed (FIG. 43) following termination at 42 weeks. Treatment with compound 5 at the 1.0 and 3.0 mg/kg doses or with cyclophosphamide significantly reduced kidney weight relative to vehicle, indicating that disease progression was significantly slowed in these mice. Treatment with 1.0 mg/kg and with 3.0 mg/kg of compound 5 resulted in a dose-independent decrease in the severity of glomerular lesions, while animals treated with 0.3 mg/kg had a glomerular lesion score less than to that of the vehicle control, but not significant (FIG. 44A). The minimal score for untreated animals was attributed to biologic variation in the normal cellularity of the glomeruli. Treatment with compound 5 resulted in a dose-dependent decrease in tubular and interstitial lesions and this effect was significant at 1.0 and 3.0 mg/kg. The 3.0 mg/kg dose was not statistically different from treatment with cyclophosphamide (FIG. 44B).

Example 18

Reduction of Spleen Weight and Splenocyte Count

Figure 45:
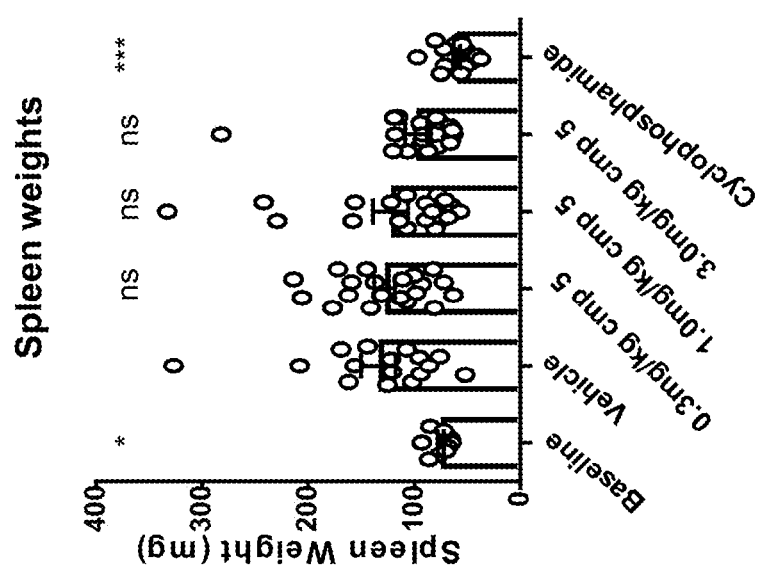
FIG. 45 shows spleen weights for the various treatment groups at termination of the study (42 weeks).

To determine the effects of compound 5 on inflammatory infiltrate in the spleen, spleens were weighed at 42 weeks. As shown in FIG. 45, spleen weights were lower, but not significant relative to vehicle for compound 5 at any dose. The 3 mg/kg dose of compound 5 trended lower indicating fewer inflammatory infiltrates in this organ. Splenocyte suspensions were prepared for all three doses. RBCs were lysed and splenocytes were counted. As shown in Table 2, total splenocyte counts were reduced in all groups treated with compound 5 relative to vehicle.

TABLE 2

Immunophenotyping of B cells, T cells, pDC Monocytes, Tfh and Treg Cells in Spleens from NZBWF1 Mice
Percent Reduction vs Vehicle in Cells Treated with:

|  | Cyclophosphamide | 0.3 mg/kg Cmp 5 | 1.0 mg/kg Cmp 5 | 3.0 mg/kg Cmp 5 |
|---|---|---|---|---|
| Total splenocytes | 73 | 35 | 50 | 60 |
| CD19 + B cells | 91 | 43 | 69 | 74 |
| Marginal Zone B cells | 57 | 20 | 63 | 54 |
| Marginal Zone Progenitor B cells | 78 | 75 | 88 | 85 |
| Germinal Center B cells | 99 | 46 | 57 | 64 |
| Follicular B cells | 93 | 43 | 66 | 72 |
| Plasma cells | 90 | 50 | 66 | 70 |
| CD4 + T cells | 77 | 51 | 75 | 81 |
| CD8 + T cells | 48 | 46 | 77 | 75 |
| Activated CD4 + T cells | 89 | 46 | 72 | 80 |
| Naive CD4 + T cells | 45 | 73 | 91 | 88 |
| pDC | 64 | 49 | 72 | 68 |
| CD11b + Ly6C$^{hi}$ monocytes | 25 | −17 | 34 | 28 |
| Tfh cells | 97 | 35 | 51 | 68 |
| Treg cells | 80 | 37 | 58 | 81 |

Cell counts of splenocyte subtypes are also shown in Table 2, which demonstrates that treatment with 3.0 mg/kg of compound 5 in particular resulted in significant cell subtype reductions: a 74% reduction in CD19$^+$ B cell population; compare to 91% reduction with cyclophosphamide; a 54% reduction in Marginal Zone ("MZ") B cell population; compare to 57% reduction with cyclophosphamide; an 85% reduction in Marginal Zone Progenitor B cells; compared to a 78% reduction with cyclophosphamide; a 64% reduction in Germinal Center ("GC") B cell population treatment; compare to 99% reduction with cyclophosphamide; a 72% decrease in Follicular ("FO") B cells; compare to 93% reduction with cyclophosphamide; a 70% reduction in plasma cell population; compare to 90% reduction with cyclophosphamide; a 81% decrease in CD4$^+$ T cell population; compare to 77% reduction with cyclophosphamide; a 75% reduction in CD8$^+$ T cell population; compare to 48% reduction with cyclophosphamide; a 80% reduction in activated CD4$^+$ T cell population; compare to 89% reduction with cyclophosphamide; an 88% reduction in naïve CD4$^+$ T cells; compare to 45% reduction with cyclophosphamide; a 68% reduction in pDC counts; compared to 64% reduction with cyclophosphamide; a 28% reduction in CD11b+Ly6C$^{hi}$ monocytes; compared to 25% reduction with cyclophosphamide; a 68% reduction in Tfh cells; compared to a 97% reduction with cyclophosphamide; and an 81% reduction in Treg cells; compared to 80% reduction with cyclophosphamide.

Example 19

Reduction of Anti-dsDNA Antibody Titers

Figure 46:
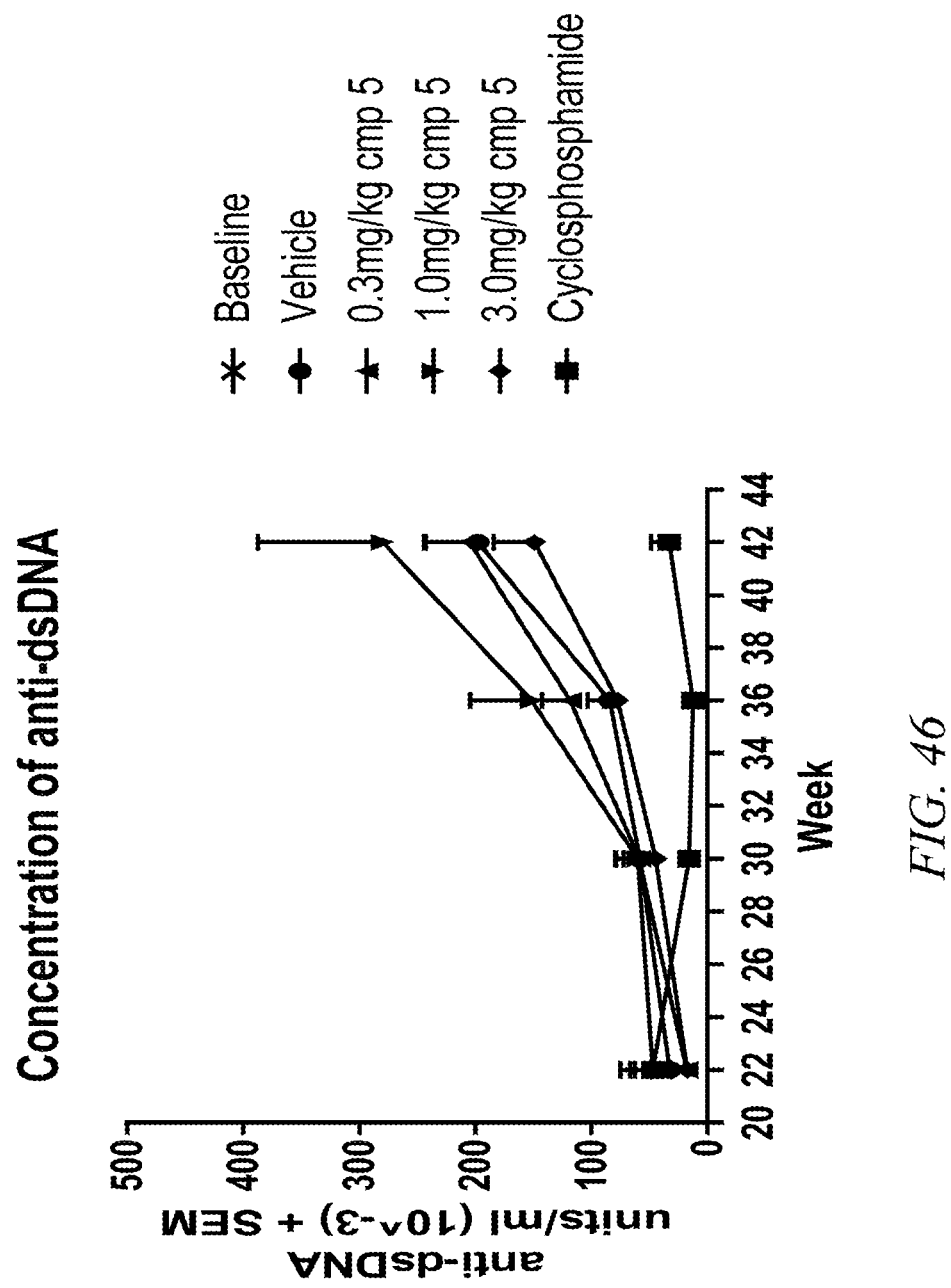
FIG. 46 shows the concentration of serum anti-dsDNA antibody titers for the various treatment groups at different points in the study (i.e., at 22, 30, 36, and 42 weeks).

As in Example 8, serum anti-dsDNA antibody titers were measured at 22, 30, 36, and 42 weeks. ELISA was performed using an anti-dsDNA ELISA kit. As shown in FIG. 46, 3 mg/kg dosages of compound 5 resulted in decreased antibody titers at week 42, but less than that for mice receiving cyclophosphamide.

Example 20

S1P1R Expression on CD4+ T Cells

Figures 47A, 47B:
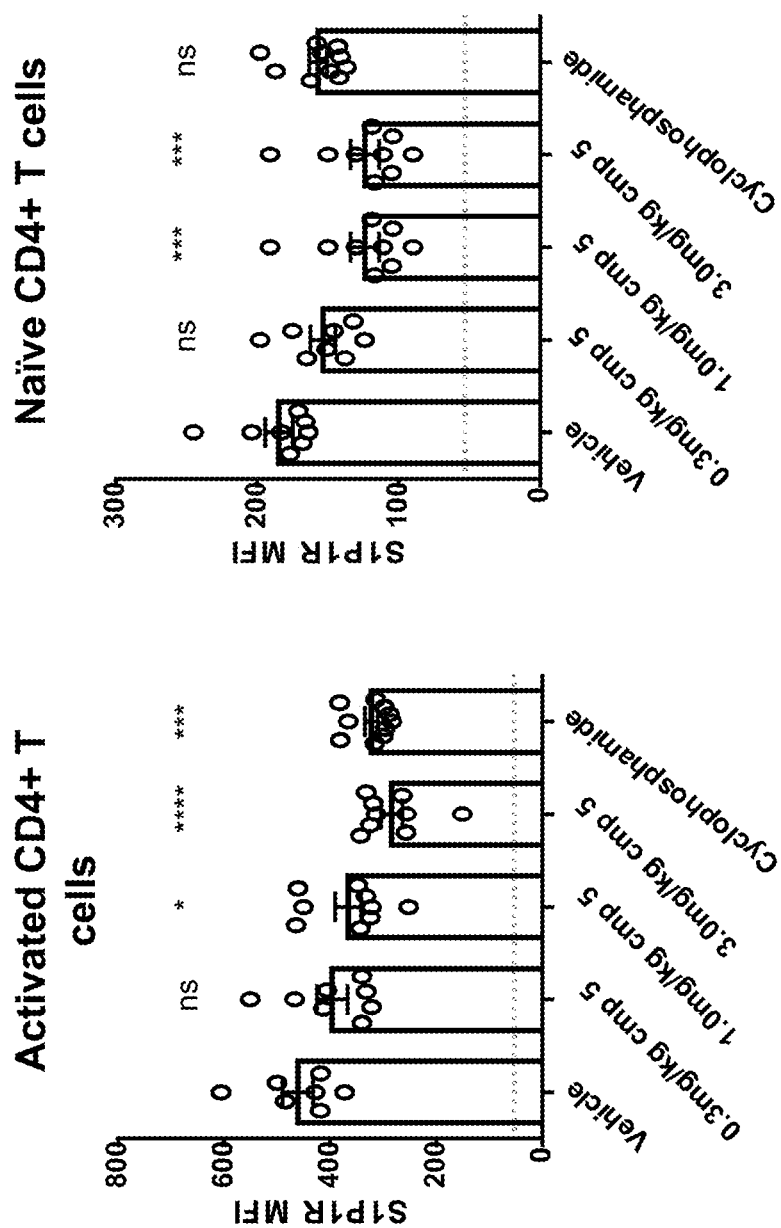

S1P1R is expressed on T and B lymphocytes and is the target for modulation by compound 5. Following agonism of the receptor by compound 5, the receptor is internalized and degraded. To determine whether internalization is occurring in T cells following compound dosing in vivo, both naïve and activated CD4+ T cells were examined for cell surface expression of S1P1R. At termination, spleens were harvested and splenocytes isolated and analyzed for immune cell populations by antibody staining and flow cytometry. S1P1R expression was measured on both activated CD4+ T cells (CD3+CD4+CD44+CD62L−) and naïve T cells (CD3+CD4+CD44−CD62L+). As shown in FIGS. 47A and 47B, S1P1R expression was reduced in a dose-dependent manner in mice treated with compound 5 in both activated and naïve CD4+ T cells.

U.S. Provisional Patent Application No. 62/401,762, filed Sep. 29, 2016, to which the present application claims priority, is hereby incorporated herein by reference in its entirety.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

We claim:

1. A method for treating systemic lupus erythematosus in a subject in need thereof, the method comprising administering to the subject an effective amount of a compound having the following structure, or a pharmaceutically acceptable salt, homolog, hydrate or solvate thereof:

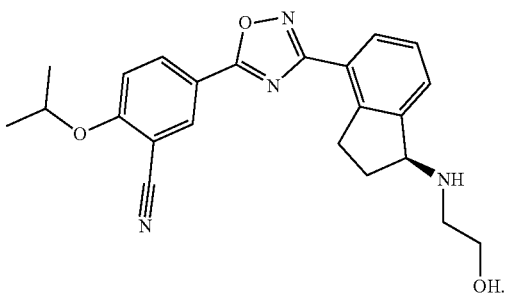 [SMILES: CC(C)Oc1ccc(-c2nc(-c3cccc4c3CC[C@@H]4NCCO)no2)cc1C#N]

2. The method of claim 1, wherein the compound is in the form of a racemic mixture.

3. The method of claim 1, wherein the compound is in the form of an isolated optical isomer.